(12) United States Patent
O'Toole et al.

(10) Patent No.: US 10,881,766 B2
(45) Date of Patent: Jan. 5, 2021

(54) BREAST PUMP SYSTEM

(71) Applicant: CHIARO TECHNOLOGY LIMITED, London (GB)

(72) Inventors: Jonathan O'Toole, London (GB); Adam Rollo, London (GB); Andrew Carr, London (GB); Benjamin Levy, Longon (GB); Jack Coggins, London (GB); Clare Ross, London (GB); Rebecca Poole, London (GB); Nestor Pestana, London (GB)

(73) Assignee: CHIARO TECHNOLOGY LIMITED, London (GB)

( * ) Notice: Subject to any disclaimer, the term of this patent is extended or adjusted under 35 U.S.C. 154(b) by 0 days.

(21) Appl. No.: 16/713,099

(22) Filed: Dec. 13, 2019

(65) Prior Publication Data

US 2020/0139026 A1 May 7, 2020

Related U.S. Application Data

(63) Continuation of application No. 16/009,547, filed on Jun. 15, 2018.

(30) Foreign Application Priority Data

Jun. 15, 2017 (GB) .................................. 1709561.3
Jun. 15, 2017 (GB) .................................. 1709564.7

(Continued)

(51) Int. Cl.
*A61M 1/06* (2006.01)
*G16H 40/63* (2018.01)
(Continued)

(52) U.S. Cl.
CPC .............. *A61M 1/062* (2014.02); *A61M 1/06* (2013.01); *A61M 1/066* (2014.02); *G16H 40/63* (2018.01);
(Continued)

(58) Field of Classification Search
CPC ........ A61M 1/062; A61M 1/066; A61M 1/06; A61M 1/068
See application file for complete search history.

(56) References Cited

U.S. PATENT DOCUMENTS 2,849,881 A 9/1958 Anderson
4,390,024 A 6/1983 Williams
(Continued)

FOREIGN PATENT DOCUMENTS

CN 105288759 A 2/2016
DE 3311982 C2 10/1983
(Continued)

OTHER PUBLICATIONS

GB Search Report, dated Nov. 15, 2017, issued in priority GB Application No. GB1709561.3.
(Continued)

*Primary Examiner* — Nathan R Price
*Assistant Examiner* — Courtney B Fredrickson
(74) *Attorney, Agent, or Firm* — Saul Ewing Arnstein & Lehr LLP

(57) ABSTRACT

The invention is a wearable breast pump system including a housing shaped at least in part to fit inside a bra and a piezo air-pump. The piezo air-pump is fitted in the housing and forms part of a closed loop system that drives a separate, deformable diaphragm to generate negative air pressure. The diaphragm is removably mounted on a breast shield.

28 Claims, 44 Drawing Sheets

(30) Foreign Application Priority Data

Jun. 15, 2017 (GB) .................... 1709566.2
Jun. 1, 2018 (GB) .................... 1809036.5

(51) Int. Cl.

| | |
|---|---|
| A41C 3/04 | (2006.01) |
| A61J 9/00 | (2006.01) |
| A61M 39/22 | (2006.01) |
| A61M 39/24 | (2006.01) |

(52) U.S. Cl.

CPC . *A41C 3/04* (2013.01); *A61J 9/00* (2013.01); *A61M 39/223* (2013.01); *A61M 39/24* (2013.01); *A61M 2205/07* (2013.01); *A61M 2205/10* (2013.01); *A61M 2205/3313* (2013.01); *A61M 2205/3327* (2013.01); *A61M 2205/3334* (2013.01); *A61M 2205/3344* (2013.01); *A61M 2205/3389* (2013.01); *A61M 2205/3553* (2013.01); *A61M 2205/3584* (2013.01); *A61M 2205/3606* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/584* (2013.01); *A61M 2205/587* (2013.01); *A61M 2205/6054* (2013.01); *A61M 2205/702* (2013.01); *A61M 2205/7536* (2013.01); *A61M 2205/80* (2013.01); *A61M 2205/8206* (2013.01); *A61M 2209/082* (2013.01); *A61M 2209/088* (2013.01)

(56) References Cited

U.S. PATENT DOCUMENTS

| | | | |
|---|---|---|---|
| 4,535,627 A | 8/1985 | Prost | |
| 5,474,683 A | 12/1995 | Bryant et al. | |
| 5,941,847 A | 8/1999 | Huber et al. | |
| 5,973,770 A | 10/1999 | Carter et al. | |
| 6,045,529 A | 4/2000 | Nuesch | |
| 6,090,065 A | 7/2000 | Giles | |
| 6,227,936 B1 * | 5/2001 | Mendoza | A41C 3/04 2/104 |
| 6,328,709 B1 * | 12/2001 | Hung | A61B 5/4312 604/514 |
| 6,358,226 B1 | 3/2002 | Ryan | |
| 6,383,163 B1 | 5/2002 | Kelly et al. | |
| 6,440,100 B1 | 8/2002 | Prentiss | |
| 6,461,324 B1 | 10/2002 | Schlensog | |
| 6,547,756 B1 | 4/2003 | Greter et al. | |
| 6,579,258 B1 | 6/2003 | Atkin et al. | |
| 6,663,587 B2 | 12/2003 | Silver et al. | |
| 6,749,582 B2 | 6/2004 | Britto et al. | |
| 7,048,519 B2 | 5/2006 | Fong et al. | |
| 7,201,735 B2 | 4/2007 | Atkin et al. | |
| D548,831 S | 8/2007 | Charlez | |
| 7,312,554 B2 | 12/2007 | Vogeley | |
| 7,314,400 B2 | 1/2008 | Fildan et al. | |
| 7,662,018 B1 * | 2/2010 | Thompson | A61J 13/00 215/306 |
| 7,776,008 B2 | 8/2010 | Renz et al. | |
| 8,057,425 B1 | 11/2011 | Myers et al. | |
| 8,118,772 B2 | 2/2012 | Dao et al. | |
| 8,187,227 B2 | 5/2012 | Luzbetak et al. | |
| 8,262,606 B2 | 9/2012 | Greter et al. | |
| 8,282,596 B2 | 10/2012 | Greter et al. | |
| 8,376,986 B2 | 2/2013 | Van Schijndel et al. | |
| 8,702,646 B2 | 4/2014 | Garbez et al. | |
| 8,801,495 B1 | 8/2014 | Guindon | |
| 8,876,760 B2 | 11/2014 | Bosman et al. | |
| 8,926,556 B2 | 1/2015 | Van Eijkelenborg et al. | |
| 9,033,913 B2 | 5/2015 | Khalil et al. | |
| 9,173,587 B2 | 11/2015 | Van Schijndel et al. | |
| 9,345,274 B1 | 5/2016 | Prill | |
| 9,539,377 B2 | 1/2017 | Makower et al. | |
| 10,039,871 B2 | 8/2018 | Pollen | |
| 2002/0193731 A1 | 12/2002 | Myers et al. | |
| 2004/0056641 A1 | 3/2004 | Myers et al. | |
| 2004/0074281 A1 | 4/2004 | Lobdell et al. | |
| 2004/0267215 A1 | 12/2004 | Charlez et al. | |
| 2005/0219302 A1 | 10/2005 | Vogeley | |
| 2006/0122575 A1 | 6/2006 | Wakabayashi | |
| 2007/0051172 A1 | 3/2007 | Perinet et al. | |
| 2007/0051727 A1 | 3/2007 | Holley, Jr. | |
| 2008/0177224 A1 | 7/2008 | Kelly | |
| 2008/0262420 A1 | 10/2008 | Dao et al. | |
| 2008/0275386 A1 * | 11/2008 | Myers | A61M 1/0068 604/74 |
| 2011/0004154 A1 * | 1/2011 | Van Schijndel | A61M 1/06 604/74 |
| 2011/0196291 A1 * | 8/2011 | Vischer | A61M 1/0066 604/74 |
| 2011/0274566 A1 | 11/2011 | Amirouche | |
| 2012/0277636 A1 | 11/2012 | Blondheim et al. | |
| 2013/0023821 A1 * | 1/2013 | Khalil | A61M 1/064 604/74 |
| 2014/0031744 A1 | 1/2014 | Chen | |
| 2014/0052056 A1 | 2/2014 | Garbez et al. | |
| 2014/0275857 A1 * | 9/2014 | Toth | A61M 16/021 600/301 |
| 2014/0323962 A1 | 10/2014 | Kooijker | |
| 2014/0378895 A1 * | 12/2014 | Barack | A61M 1/064 604/74 |
| 2015/0217036 A1 | 8/2015 | Pollen et al. | |
| 2015/0217037 A1 | 8/2015 | Pollen et al. | |
| 2015/0283311 A1 * | 10/2015 | Alvarez | A61M 1/0031 604/514 |
| 2016/0000980 A1 | 1/2016 | Alvarez et al. | |
| 2016/0058928 A1 | 3/2016 | Nowroozi | |
| 2016/0058929 A1 | 3/2016 | Nowroozi et al. | |
| 2016/0082165 A1 | 3/2016 | Alvarez et al. | |
| 2016/0082166 A1 | 3/2016 | Guthrie et al. | |
| 2016/0151551 A1 | 6/2016 | Felber | |
| 2016/0158424 A1 | 6/2016 | Chen et al. | |
| 2016/0166745 A1 | 6/2016 | Aalders | |
| 2016/0206794 A1 * | 7/2016 | Makower | A61M 1/066 |
| 2016/0220743 A1 * | 8/2016 | Guthrie | G16H 50/30 |
| 2016/0220745 A1 * | 8/2016 | Guthrie | A61M 1/06 |
| 2016/0256617 A1 | 9/2016 | Hansen | |
| 2016/0287767 A1 | 10/2016 | Simmons et al. | |
| 2016/0296681 A1 | 10/2016 | Gaskin et al. | |
| 2016/0310650 A1 | 10/2016 | Makower et al. | |
| 2017/0021068 A1 | 1/2017 | Gaskin et al. | |
| 2017/0035951 A1 | 2/2017 | Tanaka | |
| 2017/0043065 A1 * | 2/2017 | Takeuchi | A61M 1/0003 |
| 2017/0072117 A1 * | 3/2017 | Kurihara | A61G 12/00 |
| 2017/0072118 A1 * | 3/2017 | Makower | A61M 1/06 |
| 2017/0143879 A1 | 5/2017 | Okaguchi | |
| 2017/0220753 A1 | 8/2017 | Guthrie et al. | |
| 2018/0021490 A1 | 1/2018 | Chang et al. | |
| 2018/0110900 A1 | 4/2018 | Barack | |
| 2018/0110906 A1 * | 4/2018 | Barack | F04B 35/04 |

FOREIGN PATENT DOCUMENTS

| | | |
|---|---|---|
| DE | 197 50 620 A1 | 6/1999 |
| EP | 0 503 280 A2 | 2/1992 |
| EP | 9 503 280 A2 | 2/1992 |
| EP | 1 586 340 A2 | 10/2005 |
| EP | 1 430 918 B1 | 5/2008 |
| EP | 2 436 277 A1 | 4/2012 |
| EP | 2 210 628 B1 | 2/2013 |
| EP | 1 404 393 B1 | 12/2014 |
| EP | 2 077 868 B1 | 7/2016 |
| EP | 1 263 487 B2 | 11/2016 |
| GB | 2473022 B | 12/2011 |
| GB | 2499248 B | 4/2014 |
| JP | 2016-10524 A | 1/2016 |
| JP | 2016010524 A | 1/2016 |
| RU | 2 344 380 C1 | 1/2009 |

(56) References Cited

FOREIGN PATENT DOCUMENTS

| | | |
|---|---|---|
| RU | 2344380 C1 | 1/2009 |
| RU | 2441367 C2 | 1/2010 |
| RU | 2 441 367 C2 | 2/2012 |
| WO | 94/20158 A1 | 9/1994 |
| WO | 2005/114113 A3 | 12/2005 |
| WO | 2005/114116 A1 | 12/2005 |
| WO | 2009/134271 A1 | 11/2009 |
| WO | 2015/081459 A1 | 6/2015 |
| WO | 2015/120321 A1 | 8/2015 |
| WO | 2015150225 A1 | 10/2015 |
| WO | 2015/116749 A1 | 11/2015 |
| WO | 2015/174330 A1 | 11/2015 |
| WO | 2016/002606 A1 | 1/2016 |
| WO | 2016/006494 A1 | 1/2016 |
| WO | 2016/006496 A1 | 1/2016 |
| WO | 2016/007560 A1 | 1/2016 |
| WO | 2016/014469 A1 | 1/2016 |
| WO | 2016/014488 A1 | 1/2016 |
| WO | 2016/024558 A1 | 2/2016 |
| WO | 2016/039083 A1 | 3/2016 |
| WO | 2016104673 A1 | 6/2016 |
| WO | 2016/164853 A1 | 10/2016 |
| WO | 2017/061349 A1 | 4/2017 |
| WO | 2017108555 A1 | 6/2017 |
| WO | 2017/139480 A1 | 8/2017 |

OTHER PUBLICATIONS

GB Search Report, dated Nov. 28, 2017, issued in priority GB Application No. GB1709566.2.

GB Search Report, dated Nov. 29, 2017, issued in priority GB Application No. GB1709564.7.

Whisper Wear Hands-Free Breast Pump, Model: WWPMP01, User Guide, pp. 1-20, Distributed with product at least early as 2007 (see https://web.archive.org/web/20070621162539/http://www.whisperwear.com/pump_single.html).

Whisper Wear Hands-Free Breast Pump, Model: WWPMP01, User Guide, pp. 1-20, Distributedwith product at least as early as 2007 (see https://web.archive.org/web/20070621162539/http://www.whisperwear.com/pump_single.html).

* cited by examiner

FIGURE 24

BREAST PUMP SYSTEM

CROSS-REFERENCE TO RELATED APPLICATIONS

This application is a continuation of U.S. application Ser. No. 16/009,547, filed on Jun. 15, 2018, which is based on, and claims priority to, GB Application No. 1709561.3, filed Jun. 15, 2017; GB Application No. 1709564.7, filed on Jun. 15, 2017; GB Application No. 1709566.2, filed on Jun. 15, 2017; and GB Application No. 1809036.5, filed on Jun. 1, 2018, the entire contents of each of which being fully incorporated herein by reference.

BACKGROUND OF THE INVENTION

1. Field of the Invention

The field of the invention relates to a breast pump system; one implementation of the system is a wearable, electrically powered breast pump system for extracting milk from a mother.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Description of the Prior Art

The specification of the present disclosure is broad and deep. We will now describe the prior art in relation to key aspects of the present disclosure.

Prior Art Related to Breast Pump Systems

A breast pump system is a mechanical or electro-mechanical device that extracts milk from the breasts of a lactating woman.

A typical breast pump design is as shown in WO 96/25187 A1. A large suction generating device is provided, which is freestanding. This is attached by air lines to one or two breast shields which engage with the user's breasts. A pressure cycle is applied from the suction generating device, via the air lines, to the breast shields. This generates a pressure cycle on the user's breasts to simulate the suction generated by a feeding child.

The suction generating device is a large component that connects to mains power to operate the pumps therein. Milk collection bottles are provided to store the expressed breast milk. In the system of WO 96/36298 A1 separate bottles are provided attached to each breast shield. A single bottle with tubing connecting to each breast shield may also be used. But for a mother to use this discretely, such as in an office environment, specialised bras must be used. In particular, breast-pumping bras which have a central slit, for the nipple tunnel of the breast shield to extend through, are typically used. The breast shield is held within the bra, with the suction generating device and milk bottle outside the bra.

The fundamental breast pump system has not significantly evolved from this approach, only minor technical improvements have been made.

However, these systems present a number of significant disadvantages. As the suction generating device is a large freestanding unit connected to mains power, the user may feel tethered to the wall. The known devices typically also require a specific user posture and undressing to function normally. This is obviously difficult for a user to do discretely, such as in an office setting. The known devices are also typically noisy, uncomfortable, and hard to clean.

Fully integrated wearable breast pump systems have begun to enter the market, such as described in US 2016 0206794 A1. In such pump systems, the suction source, power supply and milk container are contained in a single, wearable device; there is no need for bulky external components or connections. Such devices can be provided with a substantially breast shaped convex profile so as to fit within a user's bra for discrete pumping, as well as pumping on-the-go without any tethers to electrical sockets or collection stations. The internal breast shield is naturally convex to fit over a breast.

In US 2016 0206794 A1, when viewed from the front, the breast pump device has a 'tear-drop' rounded shape, fuller at its base than at its top. But it uses collapsible bags as milk collection devices. As the collection bag systems are collapsible, it can be difficult for a user to extract all of their milk from the bag, due to the small cut opening that is needed and the capillary action between the bonded plastic sheets that form the bag. This waste can be disheartening for the user, as this is food for their child. The bags are also not re-usable, so the user is required to purchase and maintain a stock of these. As well as presenting a recurring cost, if the user runs out of stock they are unable to use the product until more bags are purchased.

Furthermore, as a result of the collapsible bags, a complex and somewhat noisy pumping arrangement is necessary. In particular, the breast shield connects to a tube which is provided with compression units which "step" the expressed milk through the tube to the collection bag. This uses the breast milk as a hydraulic fluid to generate suction on the breast. In order to carry this out, a complex sequenced pulsing arrangement must be implemented.

In addition to these systems being particularly complex and wasteful, only a relatively small bag can be used. In US 2016 206794, approximately 110 ml (4 fluid ounces) of milk can be collected before the bag must be changed. While this may be sufficient for some users, others may produce much more milk in a session.

A further integrated wearable breast pump system is shown in US 2013 0023821 A1. In the third embodiment in this document, the breast pump system includes a motor driven vacuum pump and power source. An annular (or punctured disc) membrane is provided, with the flow path of the milk going through the centre of the annulus. The membrane is housed in separate housing and is sealed at its inner and outer edges. The breast shield has a small protrusion to engage with these housing components. However, the design of this breast pump system results in a number of problems. The use of an annular membrane, with the fluid flow path running through the opening of the annulus is undesirable as it results in a large and bulky device. There is therefore a need for improved integrated breast pump systems.

Prior Art Related to Liquid Measurement Systems

In the context of breast pump systems, it is useful to measure the quantity of expressed milk. One way to do this is to have a clear container for the breast pump, through which the level of expressed milk inside the container can be seen. However, viewing the milk bottle is not always possible, for example in a breast pump that collects milk while being worn inside a maternity bra.

An existing apparatus for detecting the level of liquid inside a container of a breast pump is that disclosed in US 2016/296681. In this apparatus, a sensing mechanism is provided at the top of a container, which detects droplets of liquid, specifically breast milk, entering the container. By detecting these droplets entering the container, the apparatus can determine the quantity of liquid which enters the container. In this apparatus, an accurate indication of the level of liquid in the container is reliant on the sensing mechanism being able to accurately record every droplet entering the container.

Particularly at times when liquid enters the container at a high flow rate, this accuracy cannot be guaranteed, leading to significant cumulative errors. An accurate indication of the level of liquid in the container in this apparatus is also reliant on the sensing mechanism always being on during the pumping process, so that power consumption of the sensing mechanism is correspondingly high.

In view of the above, there is the need for an improved way to determine the level of liquid inside a container connected to a breast pump.

Prior Art Related to Bra Clips

Many specialised bras (or brassieres) exist for maternity use and that facilitate nursing and/or breast pumping for milk collection, without the need to remove the bra itself. In a traditional nursing bra, this is achieved with the use of an at least partially detachable cup, which can be unhooked for feeding and/or pumping.

Further specialised bras are known which are provided with cut-out portions or slits which substantially align with the wearer's areola and nipple. Traditional breast pump systems comprise an elongate breast shield which extends away from the breast towards an external bottle and source of suction. The breast shield is arranged to extend through the cut-out portion or slit, with the collection bottle and pumping apparatus placed outside of the bra. These systems require the user to remove or unbutton any over-garments, and are uncomfortable when not pumping.

Integrated, wearable breast pump systems have begun to enter the market, such as previously noted US 2016 0206794 A1. In such pumps, the suction source, power supply and milk container are all in a single, wearable device, as noted above, without the need for bulky external components or connections. Such devices can be provided with a substantially breast shaped profile so as to fit within a user's bra for discrete pumping, as well as pumping on-the-go without any tethers to electrical sockets or collection stations.

Maternity (or nursing) bras such as disclosed in U.S. Pat. No. 4,390,024 A have partially detachable cups, with several hooks provided along the bra strap for attaching the cups to the strap. The cups can then be attached to different hooks in order to adjust the bra strap length. However, these attachment points are fixed. Additionally, this bra has been designed to accommodate the change in breast size before and after the feeding/pumping process. It is not designed to accommodate a breast pump. Accordingly, there is a need for a better system to accommodate integrated wearable breast pumps.

SUMMARY OF THE INVENTION

The invention is a wearable breast pump system including: a housing shaped at least in part to fit inside a bra; a piezo air-pump fitted in the housing and forming part of a closed loop system that drives a separate, deformable diaphragm to generate negative air pressure, that diaphragm being removably mounted on a breast shield.

BRIEF DESCRIPTION OF THE FIGURES

Aspects of the invention will now be described, by way of example(s), with reference to the following Figures, which each show features of various implementations of the invention including optional features that may be utilised:

FIG. 24 shows a screenshot of an application running on a connected device.

DETAILED DESCRIPTION

We will now describe an implementation of the invention, called the Elvie™ pump, in the following sections:
Section A: The Elvie™ Breast Pump System
Section B: An IR System
Section C: A Bra Clip
Section D: Piezo Pumps and Wearable Devices
Section A: The Elvie™ Breast Pump System
1. Elvie™ Breast Pump System Overview An implementation of the invention, called the Elvie™ pump, is a breast pump system that is, at least in part, wearable inside a bra. The breast pump system comprises a breast shield for engagement with the user's breast, a housing for receiving at least a portion of the breast shield and a detachable rigid milk collection container attachable, in use, to a lower face of the housing and connected to the breast shield for collecting milk expressed by the user, with a milk-flow pathway defined from an opening in the breast shield to the milk collection container. The housing inside also includes a pump for generating a negative pressure in the breast shield, as well as battery and control electronics Unlike other wearable breast pumps, the only parts of the system that come into contact with milk in normal use are the breast shield and the milk container; milk only flows through the breast shield and then directly into the milk container. Milk does not flow through any parts of the housing at all, for maximum hygiene and ease of cleaning.

Figure 1:
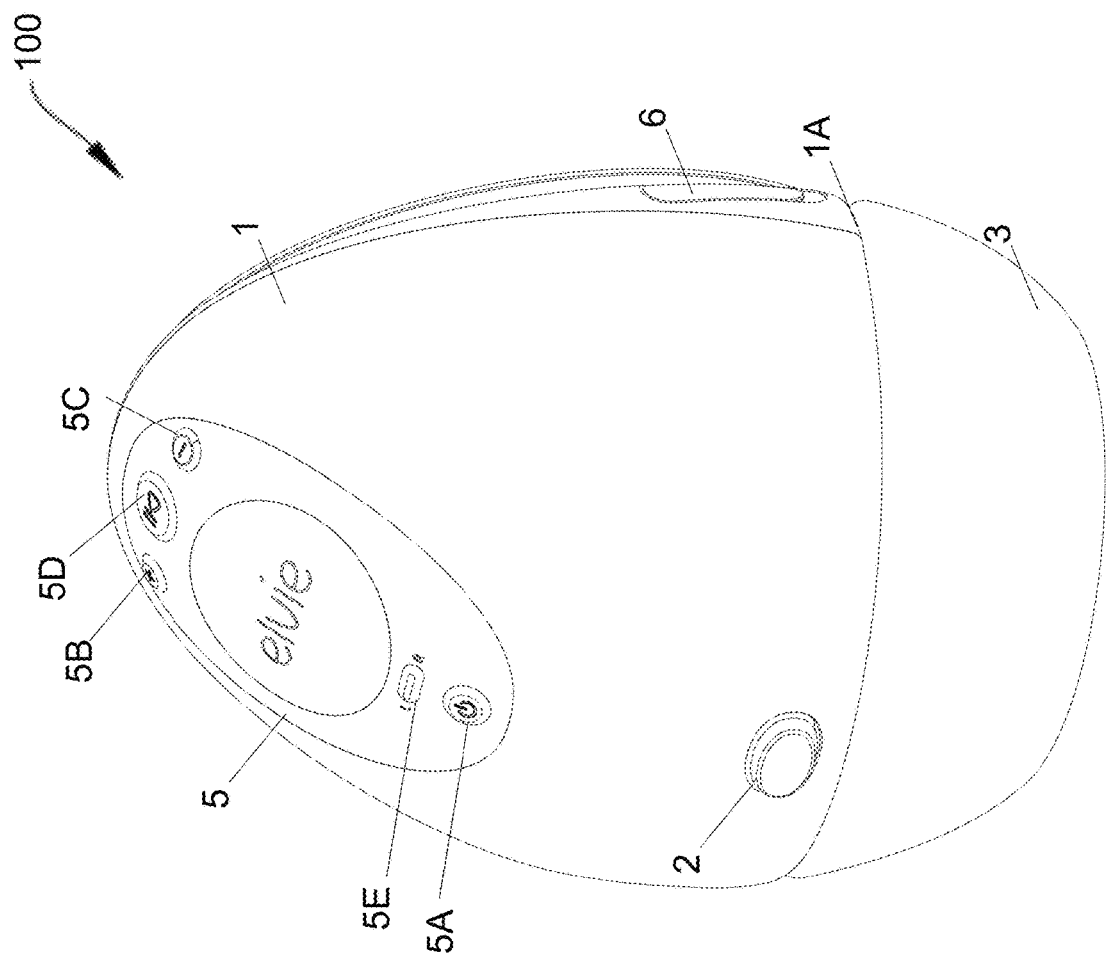
FIG. 1 is a front view of an assembled breast pump system.
Figure 2:
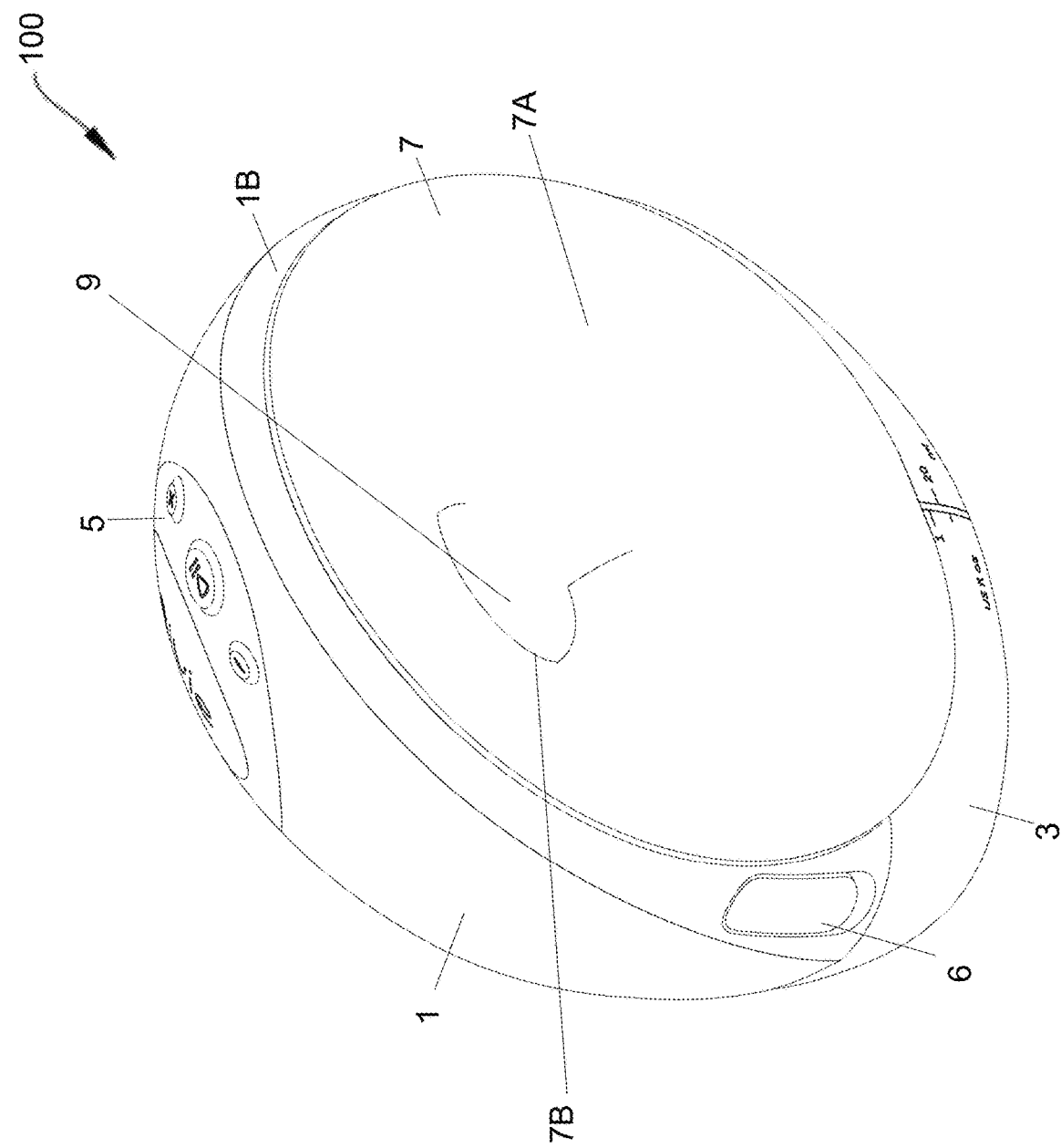
FIG. 2 is a rear view of the assembled breast pump system of FIG. 1.

With reference to FIG. 1 and FIG. 2, the assembled breast pump system 100 includes a housing 1 shaped to substantially fit inside a bra. The housing 1 includes one or more pumps and a rechargeable battery. The breast pump system includes two parts that are directly connected to the housing 1: the breast shield 7 and a milk container 3. The breast shield 7 and the milk container 3 are directly removable or attachable from the housing 1 in normal use or during normal dis-assembly (most clearly shown in FIG. 5). All other parts that are user-removable in normal use or during normal dis-assembly are attached to either the breast shield 7 or the milk container 3. The breast shield 7 and milk container 3 may be removed or attached for example using a one click or one press action or a push button or any other release mechanism. Audible and/or haptic feedbacks confirm that the pump is properly assembled.

The modularity of the breast pump allows for easy assembly, disassembly and replacement of different parts such as the breast shield and milk collection container. This also allows for different parts of the pump to be easily washed and/or sterilised. The breast shield and bottle assembly, both of which are in contact with milk during pumping, may therefore be efficiently and easily cleaned; these are the only two items that need to be cleaned; in particular, the housing does not need to be cleaned.

The housing 1, breast shield 7 that is holding a flexible diaphragm, and milk container 3 attach together to provide a closed-loop pneumatic system powered by piezoelectric pumps located in the housing 1. This system then applies negative pressure directly to the nipple, forms an airtight seal around the areola, and provides a short path for expressed milk to collect in an ergonomically shaped milk container 3.

The different parts of the breast shield system are also configured to automatically self-seal under negative pressure for convenience of assembly and disassembly and to reduce the risk of milk spillage. Self-sealing refers to the ability of sealing itself automatically or without the application of adhesive, glue, or moisture (such as for example a self-sealing automobile tire or self-sealing envelopes). Hence once the breast pump system is assembled it self-seals under its assembled condition without the need to force seals into interference fits to create sealed chambers. A degree of interference fitting is usual however, but is not the predominating attachment mechanism. Self-sealing enables simple components to be assembled together with a light push: for example, the diaphragm just needs to be placed lightly against the diaphragm housing; it will self-seal properly and sufficiently when the air-pump applies sufficient negative air-pressure. The diaphragm itself self-seals against the housing when the breast shield is pushed into the housing. Likewise, the breast shield self-seals against the milk container when the milk container is pushed up to engage the housing. This leads to simple and fast assembly and dis-assembly, making it quick and easy to set the device up for use, and to clean the device after a session.

Self-sealing has a broad meaning and may also relate to any, wholly or partly self-energising seals. It may also cover any interference seals, such as a press seal or a friction seal, which are achieved by friction after two parts are pushed together.

Whilst one particular embodiment of the invention's design and a specific form of each of the parts of the breast pump system is detailed below, it can be appreciated that the overall description is not restrictive, but an illustration of topology and function that the design will embody, whilst not necessary employing this exact form or number of discrete parts.

The breast pump system 100 comprises a housing 1 and a milk collection container (or bottle) 3. The housing 1 (including the one or more pumps and a battery) and the container 3 are provided as a unit with a convex outer surface contoured to fit inside a bra. The milk collection container 3 is attached to a lower face 1A of the housing 1 and forms an integral part of the housing when connected, such that it can be held comfortably inside a bra. While the breast pump 100 may be arranged to be used with just the right or the left breast specifically, the breast pump 100 is preferably used with both breasts, without modification. To this end, the outer surfaces of the breast pump 100 are preferably substantially symmetrical.

Preferably, the width of the complete breast pump device (housing 1 and milk container 3) is less than 110 mm and the height of the complete breast pump device is less than 180 mm.

Overall, the breast pump system 100 gives discrete and comfortable wear and use. The system weighs about 224 grams when the milk container is empty, making it relatively lighter as compared to current solutions; lightness has been a key design goal from the start, and has been achieved through a lightweight piezo pump system and engineering design focussed on minimising the number of components.

The breast pump system 100 is small enough to be at least in part held within any bra without the need to use a specialized bra, such as a maternity bra or a sports bra. The rear surface of the breast pump is also concave so that it may sit comfortably against the breast. The weight of the system has also been distributed to ensure that the breast pump is not top heavy, ensuring comfort and reliable suction against the breast. The centre of gravity of the pump system is, when the container is empty, substantially at or below the horizontal line that passes through the filling point on the breast shield, so that the device does not feel top-heavy to a person while using the pump.

Preferably, when the container is empty, the centre of gravity is substantially at or below the half-way height line of the housing so that the device does not feel top-heavy to a user using the pump.

The centre of gravity of the breast pump, as depicted by FIG. 1, is at around 60 mm high on the centreline from the base of the breast pump when the milk container is empty. During normal use, and as the milk container gradually receives milk, the centre of gravity lowers, which increases the stability of the pump inside the bra. It reduces to around 40 mm high on the centreline from the base of the breast pump when the milk container is full.

The centre of gravity of the breast pump is at about 5.85 mm below the centre of the nipple tunnel when the milk container is empty, and reduced to about 23.60 mm below the centre of the nipple tunnel when the milk container is full. Generalising, the centre of gravity should be at least 2 mm below the centre of the nipple tunnel when the container is empty.

The breast pump 100 is further provided with a user interface 5. This may take the form of a touchscreen and/or physical buttons. In particular, this may include buttons, sliders, any form of display, lights, or any other componentry necessary to control and indicate use of the breast pump 100. Such functions might include turning the breast pump 100 on or off, specifying which breast is being pumped, increasing or decreasing the peak pump pressure. Alternatively, the information provided through the user interface 5 might also be conveyed through haptic feedback, such as device vibration, driven from a miniature vibration motor within the pump housing 1.

In the particular embodiment of the Figures, the user interface 5 comprises power button 5A for turning the pump on and off. The user interface 5 further comprises pump up button 5B and pump down button 5C. These buttons adjust the pressure generated by the pump and hence the vacuum pressure applied to the user's breast. In preferable embodiments, the pump up button 5B could be physically larger than the pump down button 5C. A play/pause button 5D is provided for the user to interrupt the pumping process without turning the device off.

The user interface 5 further comprises a breast toggle button 5E for the user to toggle a display of which breast is being pumped. This may be used for data collection, e.g. via an application running on a connected smartphone; the app sends data to a remote server, where data analysis is undertaken (as discussed in more detail later), or for the user to keep track of which breast has most recently been pumped. In particular, there may be a pair of LEDs, one to the left of the toggle button 5E and one to the right. When the user is pumping the left breast, the LED to the right of the toggle button 5E will illuminate, so that when the user looks down at the toggle it is the rightmost LED from their point of view that is illuminated. When the user then wishes to switch to the right breast, the toggle button can be pressed and the LED to the left of the toggle button 5E, when the user looks down will illuminate. The connected application can automatically track and allocate how much milk has been expressed, and when, by each breast.

The breast pump system also comprises an illuminated control panel, in which the level of illumination can be controlled at night or when stipulated by the user. A day time mode, and a less bright night time mode that are suitable to the user, are available. The control of the illumination level is either implemented in hardware within the breast pump system itself or in software within a connected device application used in combination with the breast pump system.

As depicted in FIG. 1, the housing 1 and milk collection container 3 form a substantially continuous outer surface, with a generally convex shape. This shape roughly conforms with the shape of a 'tear-drop' shaped breast. This allows the breast pump 100 to substantially fit within the cup of a user's bra. The milk collection container 3 is retained in attachment with the housing 1 by means of a latch system, which is released by a one-click release mechanism such as a push button 2 or any other one-handed release mechanism. An audible and/or haptic feedback may also be used to confirm that the milk collection container 3 has been properly assembled.

The European standard EN 13402 for Cup Sizing defines cup sizes based upon the bust girth and the underbust girth of the wearer and ranges from AA to Z, with each letter increment denoting an additional 2 cm difference. Some manufacturers do vary from these conventions in denomination, and some maternity bras are measured in sizes of S, M, L, XL, etc. In preferred embodiments, the breast pump 100 of the present invention corresponds to an increase of between 3 or 4 cup sizes of the user according to EN 13402.

A plane-to-plane depth of the breast pump can also be defined. This is defined as the distance between two parallel planes, the first of which is aligned with the innermost point of the breast pump 100, and the second of which is aligned with the outermost point of the breast pump 100. This distance is preferably less than 100 mm.

FIG. 2 is a rear view of the breast pump 100 of FIG. 1. The inner surface of the housing 1 and milk collection container 3 are shown, along with a breast shield 7. The housing 1, milk collection container 3 and breast shield 7 form the three major subcomponents of the breast pump system 100. In use, these sub-components clip together to provide the functioning breast pump system 100. The breast shield 7 is designed to engage with the user's breast, and comprises a concave inner flange 7A which contacts the breast. To allow the breast pump 100 to be used on either of the user's breasts, the breast shield 7 is preferably substantially symmetrical on its inner flange 7A.

The inner flange 7A is substantially oval-shaped. While the inner flange 7A is concave, it is relatively shallow such that it substantially fits the body form of the user's breast. In particular, when measured side-on the inner-most point of the flange 7A and the outer-most point may be separated by less than 25 mm. By having a relatively shallow concave surface, the forces applied can be spread out over more surface area of the breast. The flatter form also allows easier and more accurate location of the user's nipple. In particular, the flange 7A of the breast shield 7 may extend over the majority of the inner surface of the housing 1 and milk collection container 3. Preferably, it may extend over 80% of this surface. By covering the majority of the inner surface, the breast shield is the only component which contact's the wearer's breast. This leaves fewer surfaces which require thorough cleaning as it reduces the risk of milk contacting a part of the device which cannot be easily sterilized. Additionally, this also helps to disperse the pressure applied to the user's breast across a larger area.

The breast shield 7 substantially aligns with the outer edge 1B of the housing 1. The milk collection container 3 may be provided with an arcuate groove for receiving a lower part of the breast shield 7. This is best shown in later Figures. In the assembled arrangement of FIGS. 1 and 2, the inner surface of the breast pump 100 is substantially continuous.

The breast shield 7 comprises a shield flange for engaging the user's breast, and an elongate nipple tunnel 9) aligned with the opening and extending away from the user's breast. Breast shield nipple tunnel 9 extends from a curved section 7B in the breast shield 7. In preferable embodiments the nipple tunnel 9 is integral with the breast shield 7. However, it is appreciated that separate removable/interchangeable nipple tunnels may be used. Curved section 7B is positioned over the user's nipple and areola in use. The breast shield 7 forms an at least partial seal with the rest of the user's breast around this portion, under the negative air pressure created by an air-pressure pump.

This breast shield nipple tunnel 9 defines a milk-flow path from the inner surface of the breast shield 7A, through the breast shield nipple tunnel 9 and into the milk collection container 3. The breast shield nipple tunnel 9 is preferably quite short in order to minimise the length of the milk-flow path in order to minimise losses. By reducing the distance covered by the milk, the device is also reduced in size and complexity of small intermediate portions. In particular, the breast shield nipple tunnel 9 may extend less than 70 mm from its start to end, more preferably less than 50 mm. In use, the nipple tunnel 9 is substantially aligned with the user's nipple and areolae. The nipple tunnel comprises a first opening 9A for depositing milk into the collection container and a second opening 19A for transferring negative air pressure generated by the pump to the user's nipple.

The shield flange 7A and nipple tunnel 9 may be detachable from the housing 1 together. The shield flange 7A and nipple tunnel 9 being detachable together helps further simplify the design, and reduce the number of components which must be removed for cleaning and sterilization. However, preferably, the nipple tunnel 9 will be integral with the breast shield 7, in order to simplify the design and reduce the number of components which must be removed for cleaning and sterilisation.

Figure 3:
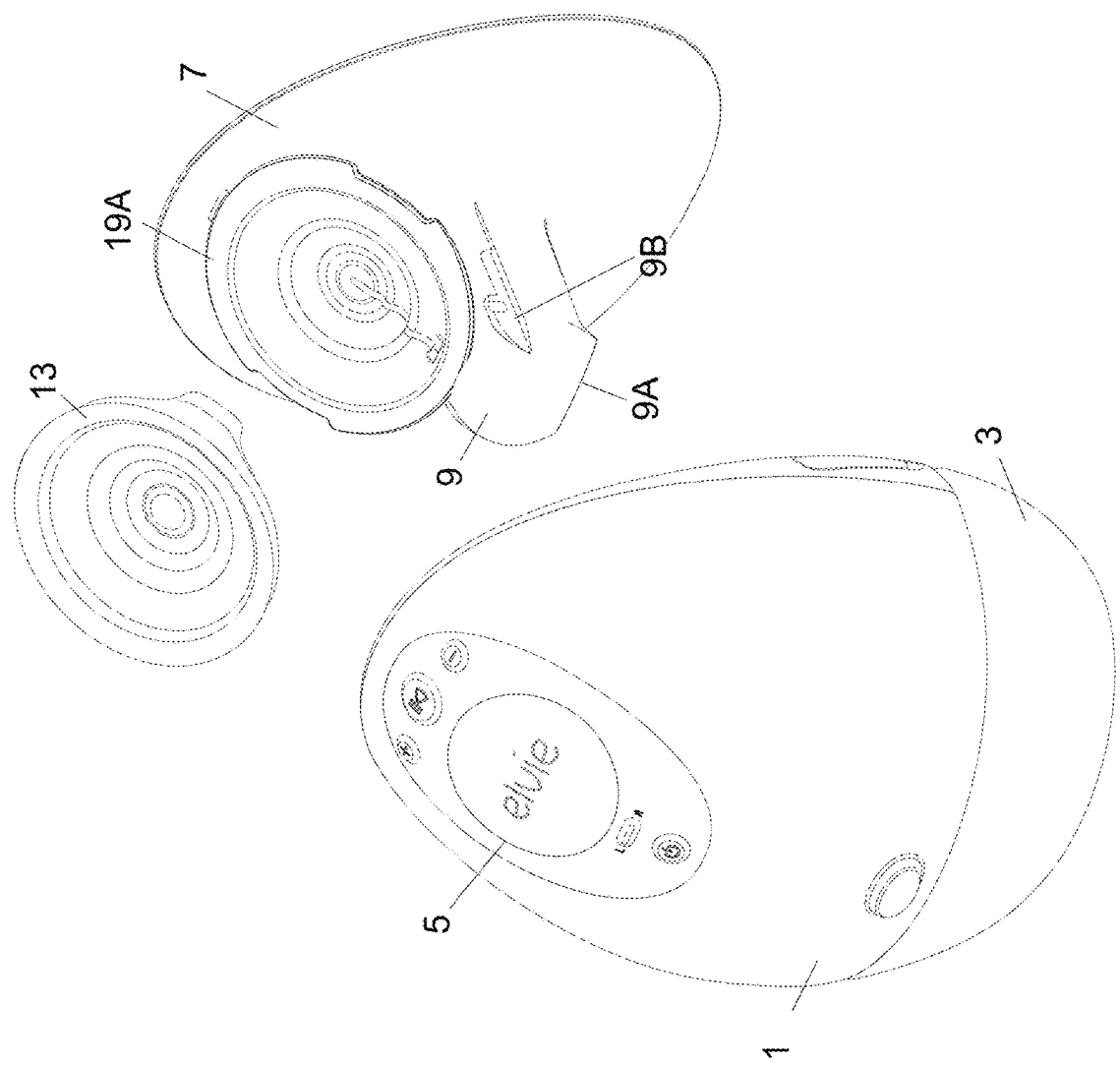
FIG. 3 is a front view of a partially disassembled breast pump system.
Figure 4:
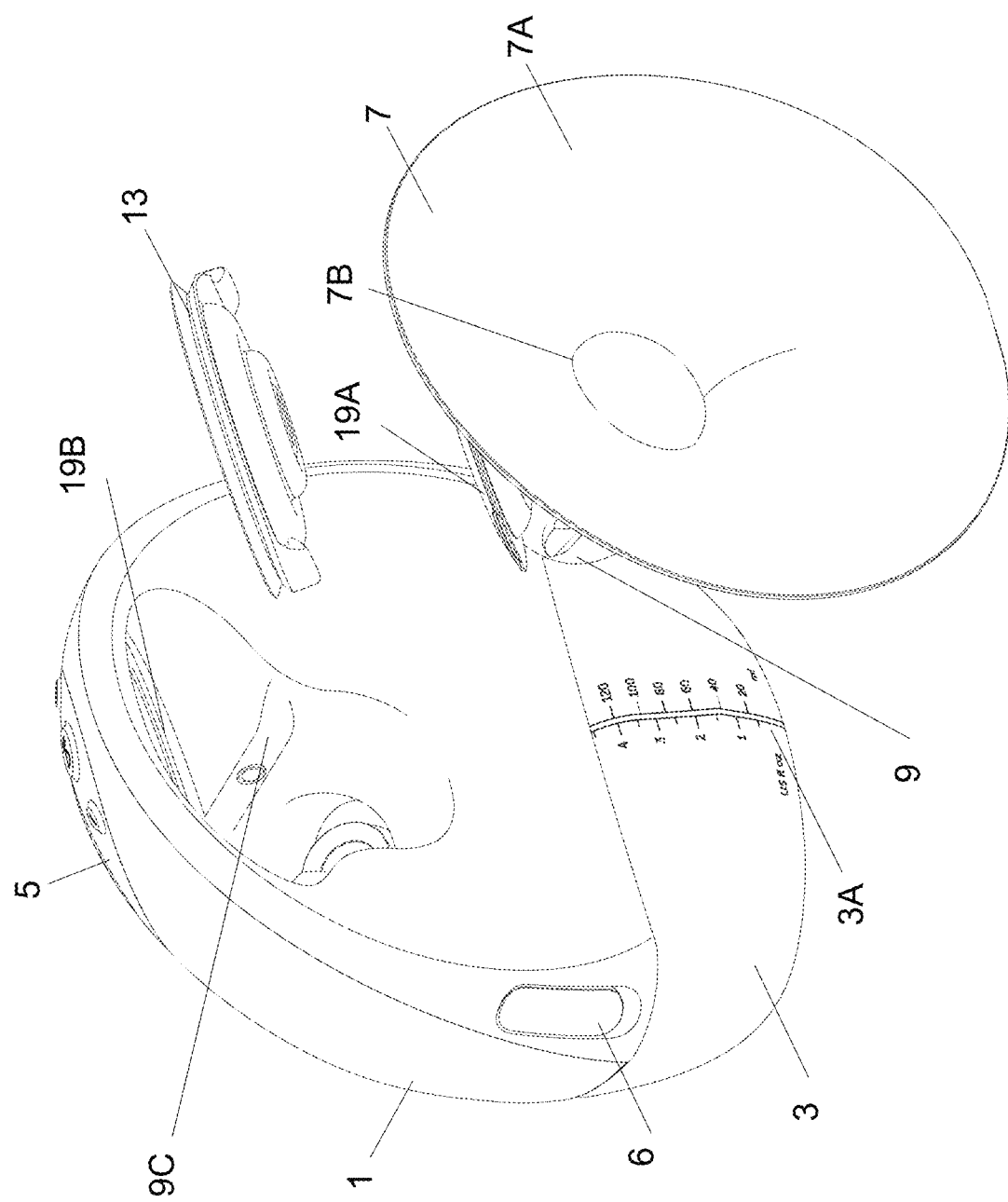
FIG. 4 is a rear view of the partially disassembled breast pump system of FIG. 3.

FIGS. 3 and 4 are of a partially disassembled breast pump 100 of the present invention. In these Figures, the breast shield 7 has been disengaged from the housing 1 and milk collection bottle 3. As shown in FIG. 4, the housing 1 comprises a region or slot 11 for receiving the breast shield nipple tunnel 9 of the breast shield 7. The breast shield is held in place thanks to a pair of channels (9B) included in the nipple tunnel 9, each channel including a small indent. When pushing the housing 1 onto the breast shield 7, which has been placed over the breast, ridges in the housing (9C) engage with the channels, guiding the housing into position; a small, spring plunger, such as ball bearing in each ridge facilitates movement of the housing on to the nipple tunnel 9. The ball bearings locate into the indent to secure the housing on to the nipple tunnel with a light clicking sound. In this way, the user can with one hand place and position the breast shield 7 onto her breast and with her other hand, position and secure the housing 1 on to the breast shield 7. The breast shield 7 can be readily separated from the housing 1 since the ball bearing latch only lightly secures the breast shield 7 to the housing 1.

Alternatively, the breast shield 7 may also be held in place by means of a clip engaging with a slot located on the housing. The clip may be placed at any suitable point on the shield 7, with the slot in a corresponding location.

The breast shield nipple tunnel 9 of the breast shield 7 is provided with an opening 9A on its lower surface through which expressed milk flows. This opening 9A is configured to engage with the milk collection bottle 3.

The breast pump 100 further comprises a barrier or diaphragm for transferring the pressure from the pump to the milk-collection side of the system. In the depicted example, this includes flexible rubber diaphragm 13 seated into diaphragm housing 19A. The barrier could be any other suitable component such as a filter or an air transmissive material. Diaphragm housing 19A includes a small air hole into the nipple tunnel 9 to transfer negative air pressure into nipple tunnel 9 and hence to impose a sucking action on the nipple placed in the nipple tunnel 9.

Hence, the air pump acts on one side of the barrier or diaphragm 13 to generate a negative air pressure on the opposite, milk-flow side of the barrier. The barrier has an outer periphery or surface, i.e. the surface of diaphragm housing 19A that faces towards the breast, and the milk-flow pathway extends underneath the outer periphery or surface of the barrier or diaphragm housing 19A. The milk-flow path extending under the outer periphery or surface of the barrier 19A allows for a simpler and more robust design, without the milk-flow pathway extending through the barrier. This provides increased interior space and functionality for the device.

As noted, the milk-flow pathway extends beneath or under the barrier 13 or surface of diaphragm housing 19A. This provides an added benefit of having gravity move the milk down and away from the barrier.

Preferably the milk-flow pathway does not pass through the barrier 32. This results in a simpler and smaller barrier design.

As noted, the diaphragm 13 is mounted on diaphragm housing 19A that is integral to the breast shield. This further helps increase the ease of cleaning and sterilisation as all of the components on the "milk" flow side can be removed.

The barrier 13 may also provide a seal to isolate the air pump from the milk-flow side of the barrier. This helps to avoid the milk becoming contaminated from the airflow or pumping side (i.e. the non-milk-flow side).

Alternatively, the only seal is around an outer edge of the barrier 13. This is a simple design as only a single seal needs to be formed and maintained. Having multiple seals, such as for an annular membrane, introduces additional complexity and potential failure points.

As illustrated in FIGS. 3 and 4, the barrier may include a flexible diaphragm 13 formed by a continuous circular disc shaped membrane which is devoid of any openings or holes. This provides a larger effective "working" area of the diaphragm (i.e. the area of the surface in contact with the pneumatic gasses) than an annular membrane and hence the membrane may be smaller in diameter to have the same working area.

The diaphragm 13 is arranged so that the milk-flow pathway extends below and past the outer surface or periphery of the diaphragm 13. This means that the milk-flow pathway does not extend through the diaphragm 13. In particular, the milk-flow pathway is beneath the diaphragm 13. However, the diaphragm 13 may be offset in any direction with respect to the milk-flow pathway, provided that the milk-flow pathway does not extend through the diaphragm 13.

Preferably, the diaphragm 13 is a continuous membrane, devoid of any openings. The diaphragm 13 is held in a diaphragm housing 19, which is formed in two parts. The first half 19A of the diaphragm housing 19 is provided on the outer surface of the breast shield 7, above the breast shield nipple tunnel 9 and hence the milk-flow pathway. In preferred embodiments, the first half 19A of the diaphragm housing 19 is integral with the breast shield. The second half 19B of the diaphragm housing is provided in a recessed portion of the housing 1. The diaphragm 13 self-seals in this diaphragm housing 19 around its outer edge, to form a watertight and airtight seal. Preferably, the self-seal around the outer edge of the diaphragm 13 is the only seal of the diaphragm 13. This is beneficial over systems with annular diaphragms which must seal at an inner edge as well. Having the diaphragm 13 mounted in the breast pump 100 in this manner ensures that it is easily accessible for cleaning and replacement. It also ensures that the breast shield 7 and diaphragm 13 are the only components which need to be removed from the pump 100 for cleaning. Because the diaphragm 13 self-seals under vacuum pressure, it is easily removed for cleaning when the device is turned off.

Figure 5:
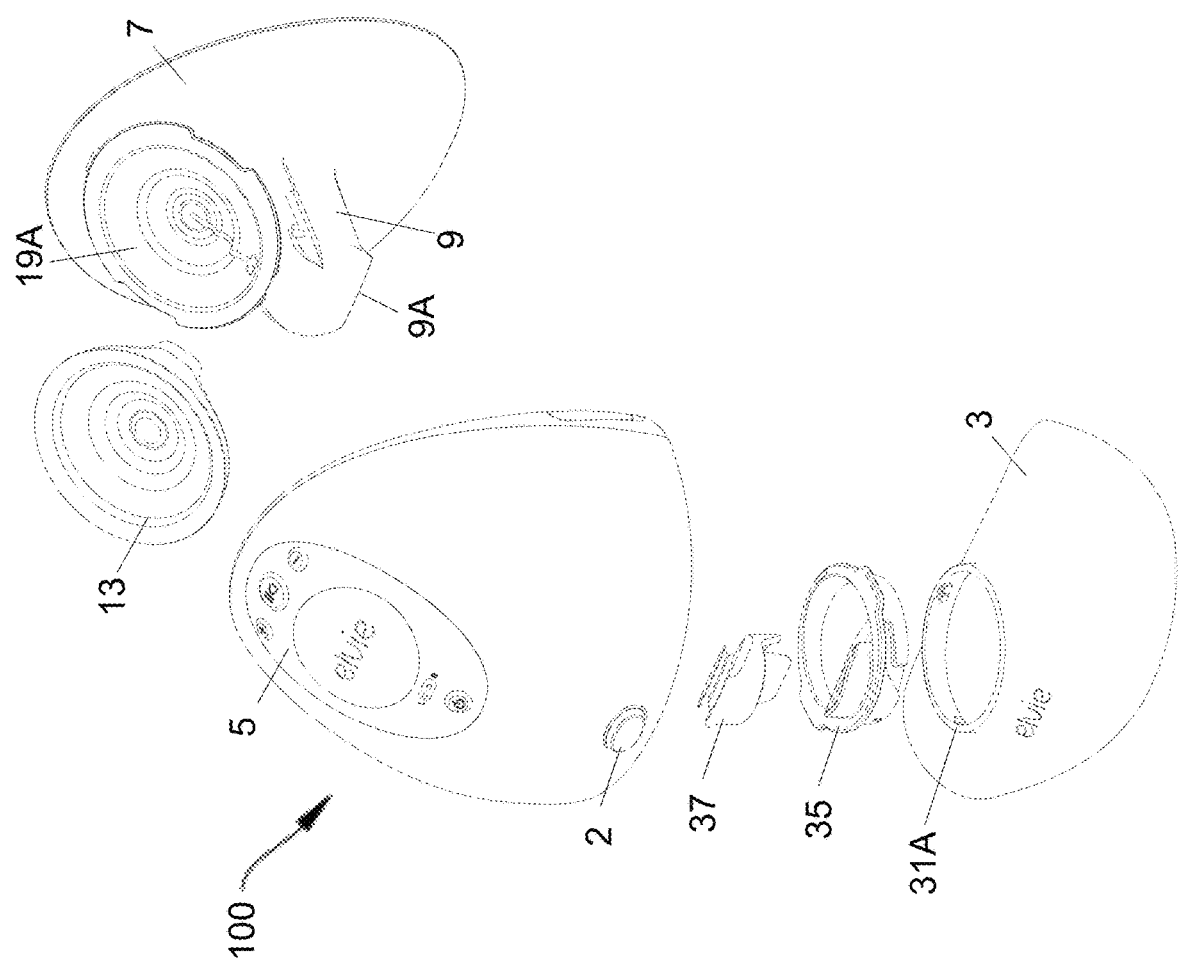
FIG. 5 is a front view of a further partially disassembled breast pump system.
Figure 6:
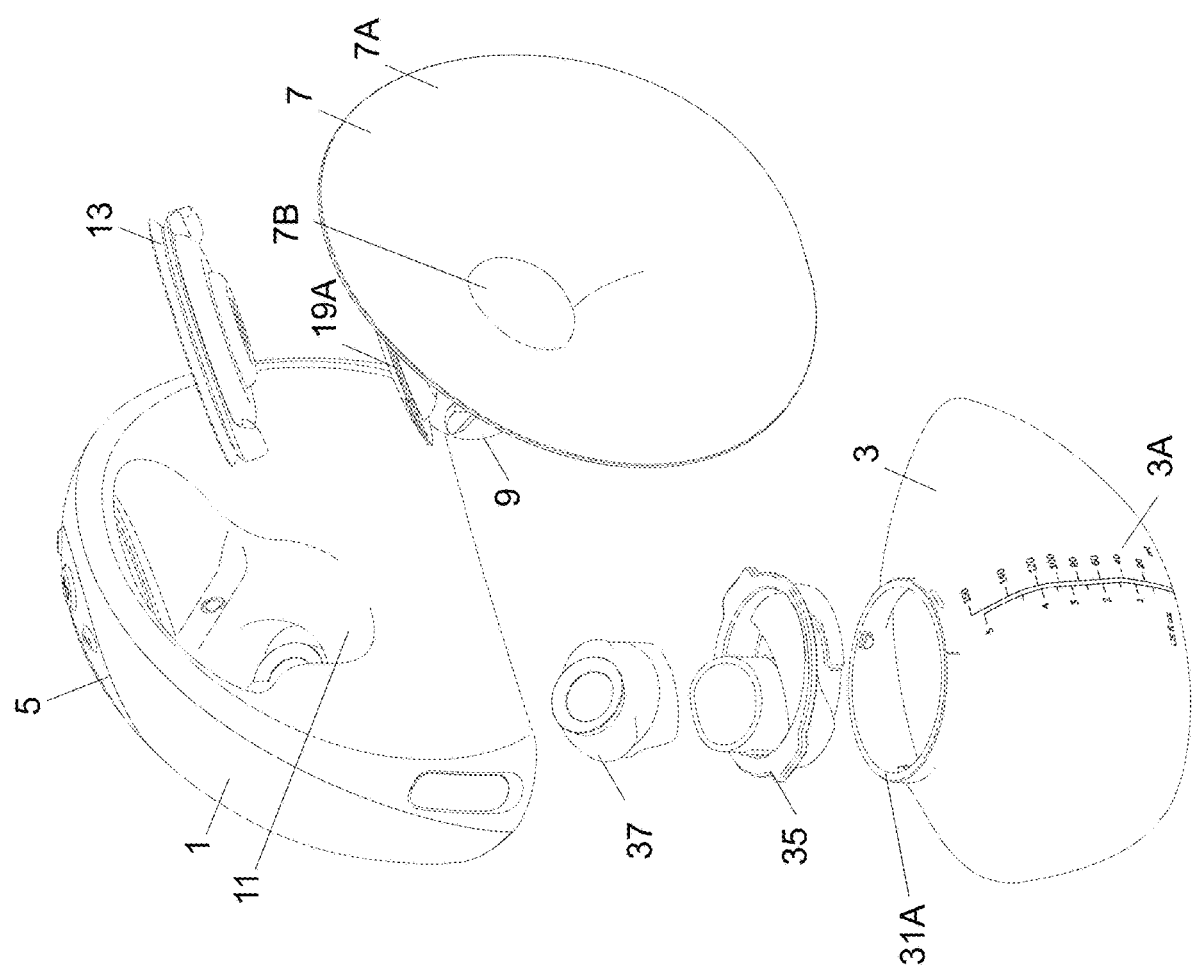
FIG. 6 is a rear view of the further partially disassembled breast pump system of FIG. 5.

FIGS. 5 and 6 show a breast pump 100 according to the present invention in a further disassembled state. In addition to the breast shield 7 and diaphragm 13 being removed, the milk collection container 3 has been unclipped. Preferably, the milk collection container 3 is a substantially rigid component. This ensures that expressed milk does not get wasted, while also enhancing re-usability. In some embodiments, the milk collection container 3 may be formed of three sections: a front bottle potion, a rear bottle potion, and a cap. These three sections may clip together to form the milk collection container 3. This three-part system is easy to empty, easily cleanable since it can be dis-assembled, and easily re-usable. The milk collection container or milk bottle may be formed of at least two rigid sections which are connectable. This allows simple cleaning of the container for re-use. Alternatively, the container may be a single container made using a blow moulding construction, with a large opening to facilitate cleaning. This large opening is then closed with a cap with an integral spout 35 or 'sealing plate' (which is bayonet-mounted and hence more easily cleaned than a threaded mount spout). A flexible rubber valve 37 (or 'sealing plate seal') is mounted onto the cap or spout 35 and includes a rubber duck-bill valve that stays sealed when there is negative air-pressure being applied by the air pump; this ensures that negative air-pressure does not need to be applied to the milk container and hence adds to the efficiency of the system. The flexible valve 37 self-seals against opening 9A in nipple tunnel 9. Because it self-seals under vacuum pressure, it automatically releases when the system is off, making it easy to remove the milk container.

Preferably, the milk collection container resides entirely below the milk flow path defined by the breast shield when the breast pump system 100 is positioned for normal use, hence ensuring fast and reliable milk collection.

The milk collection container 3 has a capacity of approximately 5 fluid ounces (148 ml). Preferably, the milk collection container has a volume of greater than 120 ml. More preferably, the milk collection container has a volume of greater than 140 ml. To achieve this, the milk collection container 3 preferably has a depth in a direction extending away from the breast in use, of between 50 to 80 mm, more preferably between 60 mm to 70 mm, and most preferably between 65 mm to 68 mm.

The milk collection container 3 further preferably has a height, extending in the direction from the bottom of the container 3 in use to the cap or spout or sealing plate 35, of between 40 mm to 60 mm, more preferably between 45 mm to 55 mm, and most preferably between 48 mm to 52 mm. The cap 35 may screw into the milk collection bottle 3. In particular, it may be provided with a threaded connection or a bayonet and slot arrangement.

Further preferably, the milk collection container has a length, extending from the leftmost point to the rightmost point of the container 3 in use, of between 100 mm to 120 30 mm, more preferably between 105 mm to 115 mm, and most preferably between 107 mm to 110 mm.

This cap 35 is provided with a one-way valve 37, through which milk can flow only into the bottle. This valve 37 prevents milk from spilling from the bottle once it has been collected. In addition, the valve 37 automatically seals completely unless engaged to the breast shield 7. This ensures that when the pump 100 is dismantled immediately after pumping, no milk is lost from the collection bottle 3. It can be appreciated that this one-way valve 37 might also be placed on the breast shield 7 rather than in this bottle cap 35.

Alternatively, the milk bottle 3 may form a single integral part with a cap 35. Cap 35 may include an integral milk pouring spout.

In certain embodiments, a teat may be provided to attach to the annular protrusion 31A or attach to the spout that is integral with cap 35, to allow the container 3 to be used directly as a bottle. This allows the milk container to be used directly as a drinking vessel for a child. The milk collection container may also be shaped with broad shoulders such that it can be adapted as a drinking bottle that a baby can easily hold.

Alternatively, or in addition, a spout may be provided to attach to the protrusion 31A for ease of pouring. A cap may also be provided to attach to the protrusion 31A in order to seal the milk collection bottle 3 for easy storage.

The pouring spout, drinking spout, teat or cap may also be integral to the milk collection container.

Further, the removable milk collection container or bottle includes a clear or transparent wall or section to show the amount of milk collected. Additionally, measurement markings (3A) may also be present on the surface of the container. This allows the level of milk within the container to be easily observed, even while pumping. The milk collection container or bottle may for example be made using an optically clear, dishwasher safe polycarbonate material such as Tritan™.

The milk collection container or bottle may include a memory or a removable tag, such as a tag including an NFC chip, that is programmed to store the date and time it was filled with milk, using data from the breast pump system or a connected device such as a smartphone. The container therefore includes wireless connectivity and connects to a companion app. The companion app then tracks the status of multiple milk collection containers or bottles to select an appropriate container or bottle for feeding. The tag of the bottle may also be programmed to store the expiry date of the milk as well as the quantity of the milk stored.

Figure 7:
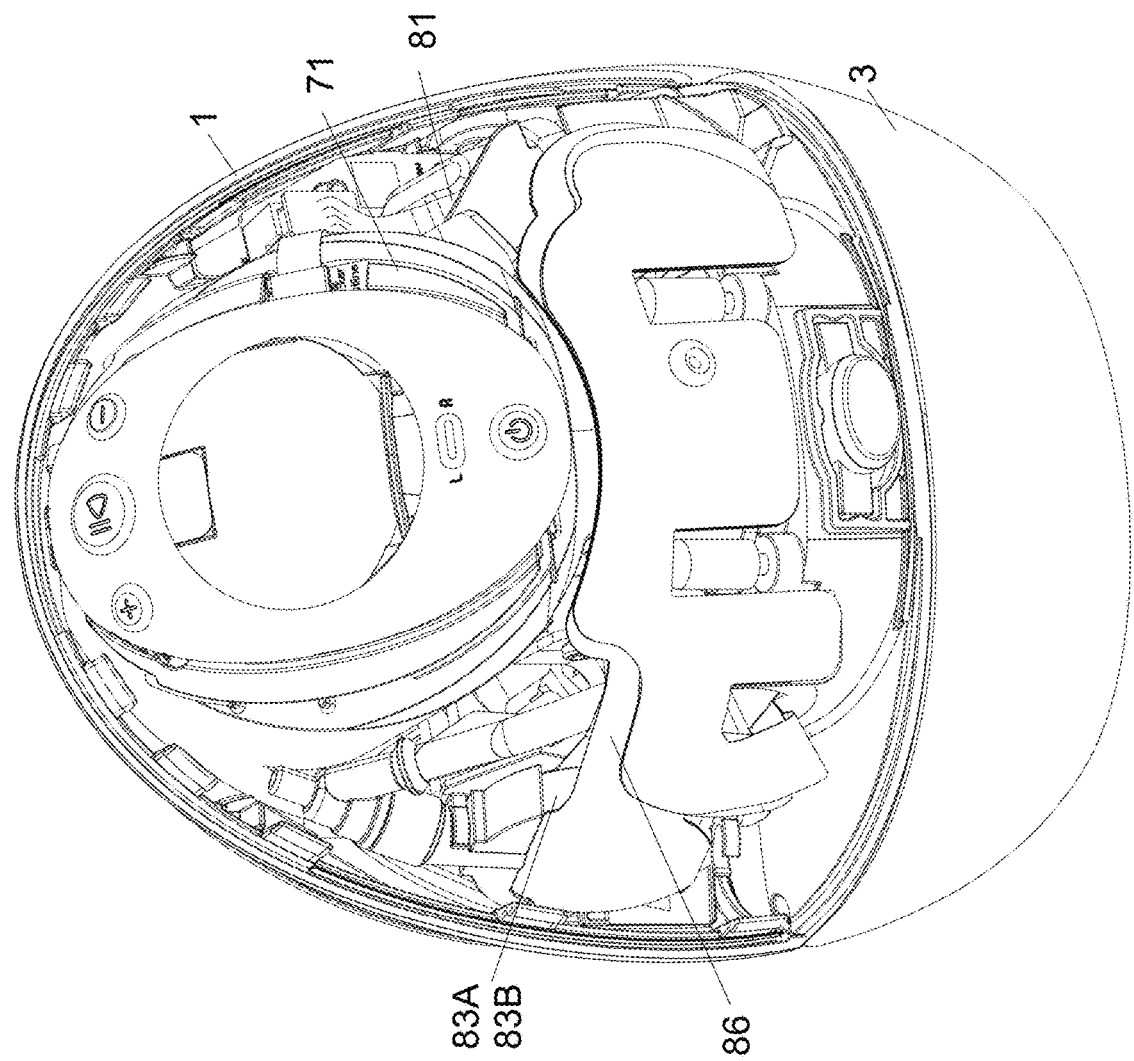
FIG. 7 is a front view of the breast pump system of FIG. 1, with the outer shell translucent for ease of explanation.
Figure 8:
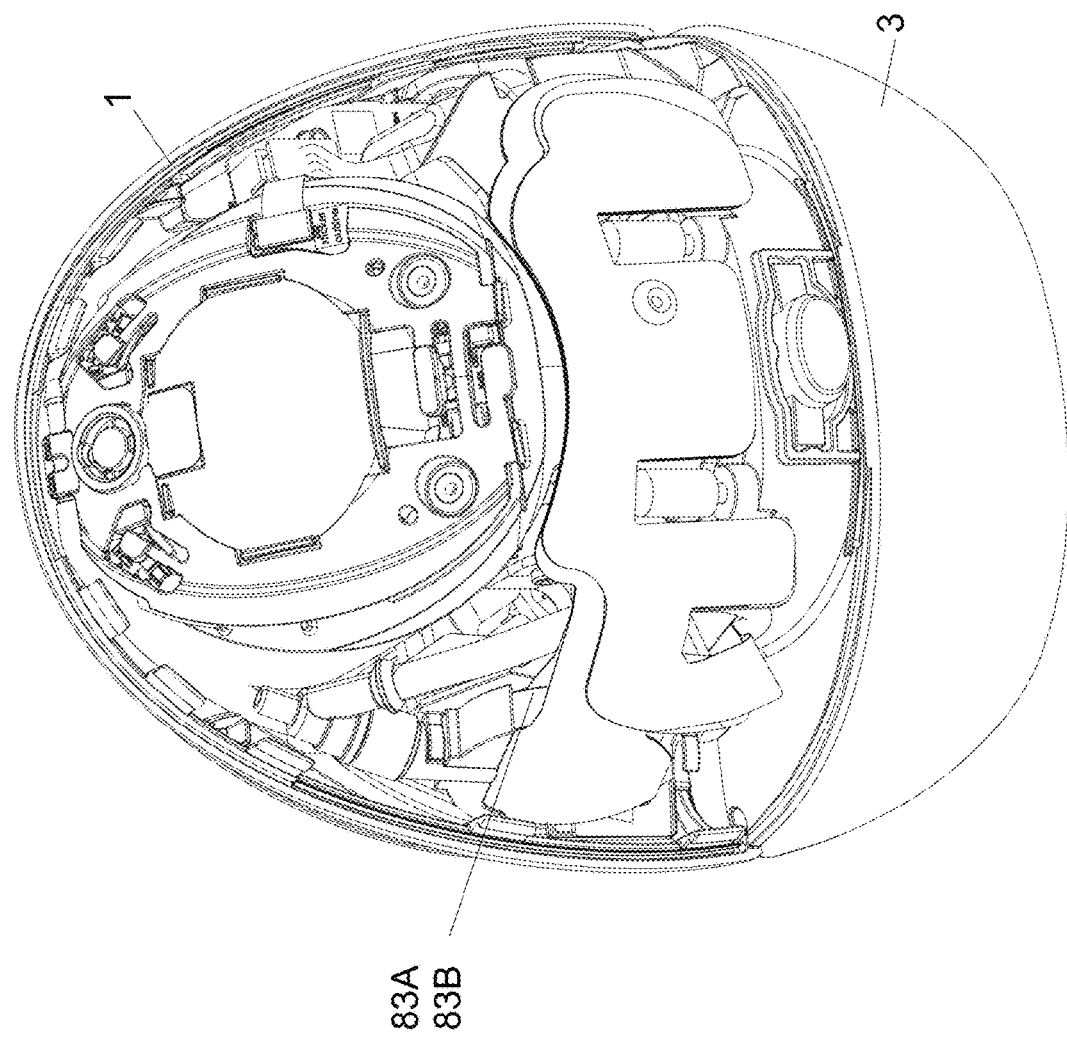
FIG. 8 is a further front view of the breast pump system of FIG. 1, with the front of the outer shell removed for ease of explanation.

FIGS. 7 and 8 show front views of a breast pump system 100. The outer-surface of the housing 1 has been drawn translucent to show the components inside. The control circuitry 71 for the breast pump 100 is shown in these figures. The control circuitry in the present embodiment comprises four separate printed circuit boards, but it is appreciated that any other suitable arrangement may be used.

The control circuitry may include sensing apparatus for determining the level of milk in the container 3. The control circuitry may further comprise a wireless transmission device for communicating over a wireless protocol (such as Bluetooth) with an external device. This may be the user's phone, and information about the pumping may be sent to this device. In embodiments where the user interface comprises a breast toggle button 5E, information on which breast has been selected by the user may also be transmitted with the pumping information. This allows the external device to separately track and record pumping and milk expression data for the left and right breasts.

There should also be a power charging means within the control circuitry 71 for charging the battery 81. While an external socket, cable or contact point may be required for charging, a form of wireless charging may instead be used such as inductive or resonance charging. In the Figures, charging port 6 is shown for charging the battery 81. This port 6 may be located anywhere appropriate on the housing 1.

FIG. 8 shows the location of the battery 81 and the pumps 83A, 83B mounted in series inside the housing 1. While the depicted embodiment shows two pumps 83A, 83B it is appreciated that the present invention may have a single pump. Preferably, an air filter 86 is provided at the output to the pumps 83A, 83B. In preferable embodiments, the pumps 83A, 83B are piezoelectric air pumps (or piezo pumps), which operate nearly silently and with minimal vibrations. A suitable piezo pump is manufactured by TIP Ventus, which can deliver in excess of 400 mBar (40 kPa) stall pressure and 1.5 litres per minute free flow. The rear side of the second half of the diaphragm housing 19B in the housing 1 is provided with a pneumatic connection spout. The pumps 83A, 83B are pneumatically connected with this connection spout.

Operation of the breast pump 100 will now be described. Once the breast pump 100 is activated and a pumping cycle is begun, the pumps 83A, 83B generates a negative air pressure which is transmitted via an air channel to a first side of the diaphragm 13 mounted on the diaphragm housing 19A. This side of the diaphragm 13 is denoted the pumping side 13B of the diaphragm 13.

The diaphragm 13 transmits this negative air pressure to its opposite side (denoted the milk-flow side 13A). This negative pressure is transferred through a small opening in the diaphragm housing 19A to the breast shield nipple tunnel 9 and the curved opening 7B of the breast shield 7 that contacts the breast. This acts to apply the pressure cycle to the breast of the user, in order to express milk. The milk is then drawn through the nipple tunnel 9, to the one way valve 37 that remains closed whilst negative pressure is applied.

When the negative air pressure is released, the valve 37 opens and milk flows under gravity past the valve 37 and into milk container 3. Negative air pressure is periodically (e.g. cyclically, every few seconds) applied to deliver pre-set pressure profiles such as profiles that imitate the sucking of a child.

While the depicted embodiment of the breast pump 100 is provided with two pumps, the following schematics will be described with a single pump 83. It is understood that the single pump 83 could be replaced by two separate piezo air-pumps 83A, 83B as above.

Figure 9:
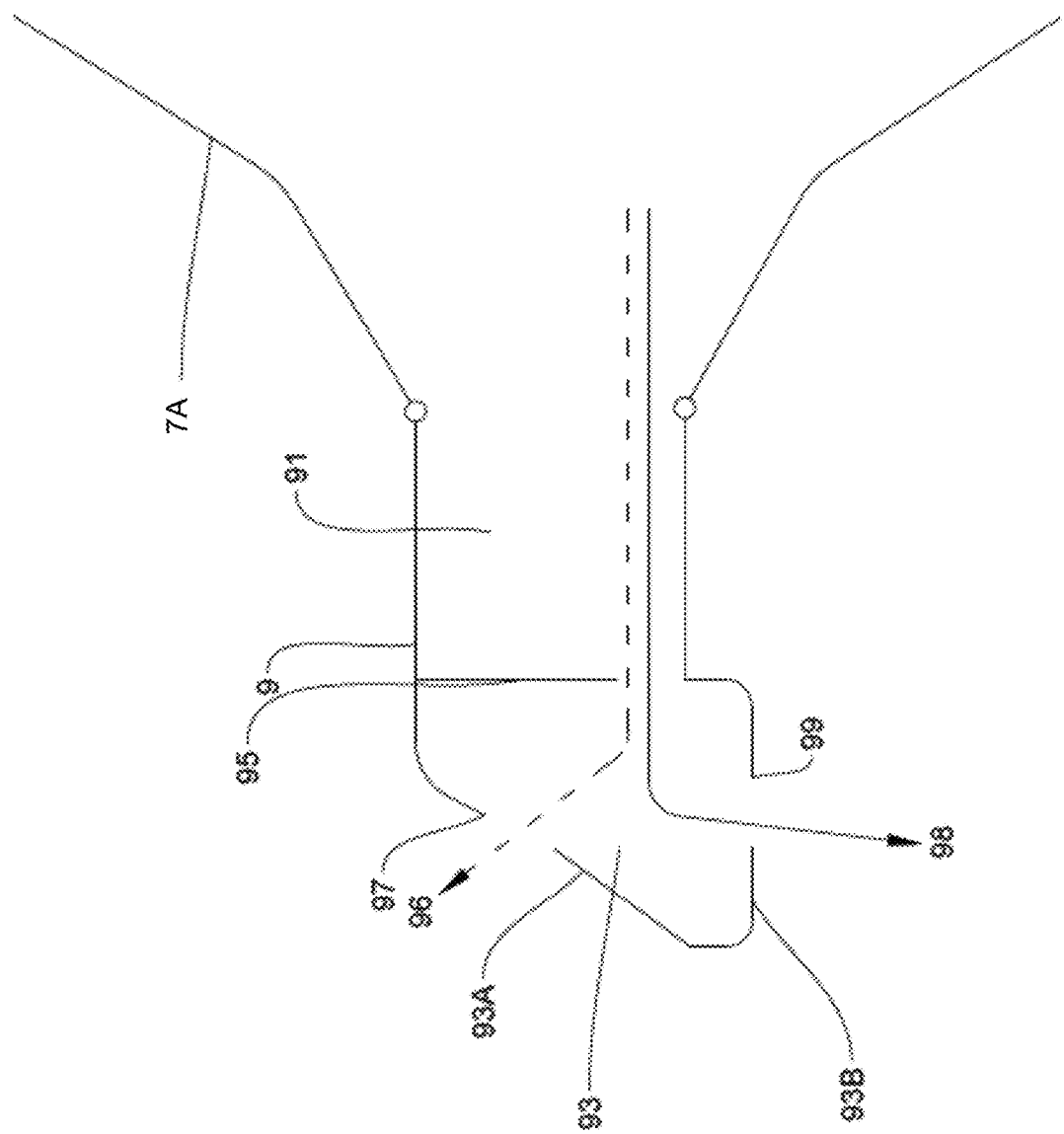
FIG. 9 is a schematic view of a nipple tunnel for a breast shield.

FIG. 9 depicts a schematic of a further embodiment of a breast shield nipple tunnel 9 for a breast pump 100. The breast shield nipple tunnel 9 is provided with an antechamber 91 and a separation chamber 93. A protrusion 95 extends from the walls of the breast shield nipple tunnel 9 to provide a tortuous air-liquid labyrinth path through the breast shield nipple tunnel 9. In the separation chamber 93 there are two opening 97, 99. An air opening 97 is provided in an upper surface 93A of the separation chamber 93. This upper surface 93 is provided transverse to the direction of the breast shield nipple tunnel 9. This opening 97 connects to the first side of the diaphragm housing 19A and is the source of the negative pressure. This airflow opening 97 also provides a route for air to flow as shown with arrow 96. It is appreciated that the tortuous pathway is not necessary and that a breast shield nipple tunnel 9 without such a pathway will work.

The other opening 99 is a milk opening 99. The milk opening 99 is provided on a lower surface 93B of the separation chamber 93 and connects in use to the container 3. After flowing through the tortuous breast shield nipple tunnel 9 pathway, the milk is encouraged to flow through this opening 99 into the container 3. This is further aided by the transverse nature of the upper surface 93A. In this manner, expressed milk is kept away from the diaphragm 13. As such, the breast pump 100 can be separated into a "air" side comprising the pump 83, the connection spout 85 and the pumping side 13B of the diaphragm 13 and a "milk-flow" side comprising the breast shield 7, the milk collection container 3 and the milk-flow side 13A of the diaphragm 13. This ensures that all of the "milk-flow" components are easily detachable for cleaning, maintenance and replacement. Additionally, the milk is kept clean by ensuring it does not contact the mechanical components. While the present embodiment discusses the generation of negative pressure with the pump 83, it will be appreciated that positive pressure may instead be generated.

While the embodiments described herein use a diaphragm 13, any suitable structure to transmit air pressure while isolating either side of the system may be used.

The breast pump may further comprise a pressure sensor in pneumatic connection with the piezo pump. This allows the output of the pump to be determined.

Figure 10:
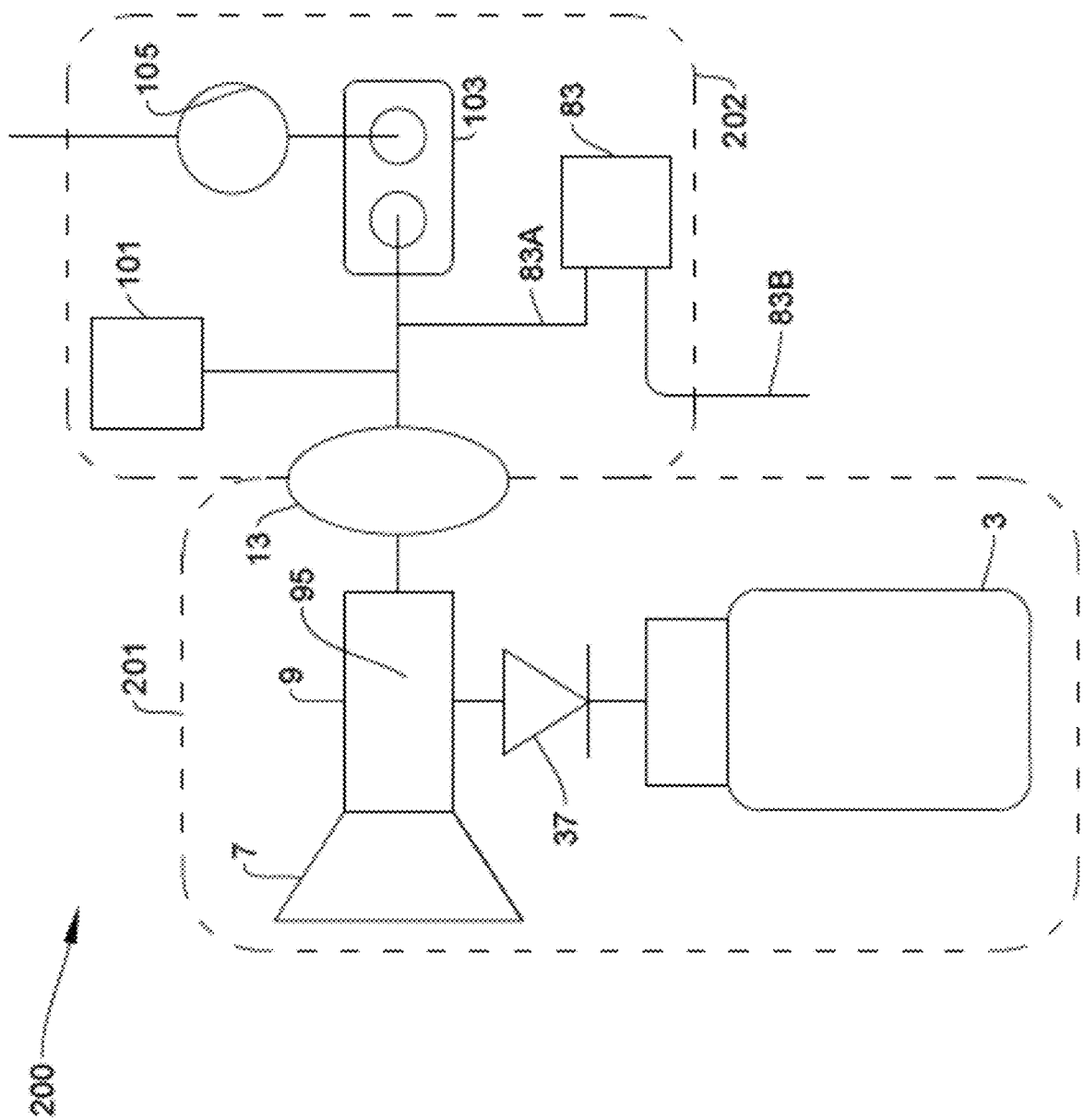
FIG. 10 is a schematic of a pneumatic system for a breast pump system.

FIG. 10 shows a schematic of a basic pneumatic system 200 for a breast pump 100. In the system 200 milk expressed into the breast shield 7 is directed through the breast shield nipple tunnel 9 through the torturous air-liquid labyrinth interface 95. The milk is directed through the non-return valve 37 to the collection container 3. This side of the system forms the "milk-flow" side 201.

The rest of the pneumatic system 200 forms the air side 202 and is separated from contact with milk. This is achieved by way of a flexible diaphragm 13 which forms a seal between the two sides of the system. The diaphragm 13 has a milk-flow side 13A and an air side or pumping side 13B.

The air side 202 of the system 200 is a closed system. This air side 202 may contain a pressure sensor 101 in pneumatic connection with the diaphragm 13 and the pump 83. Preferably, the pump 83 is a piezoelectric pump (or piezo pump). Due to their low noise, strength and compact size, piezoelectric pumps are ideally suited to the embodiment of a small, wearable breast pump. The pump 83 has an output 83A for generating pressure, and an exhaust to the atmosphere 83B. In a first phase of the expression cycle, the pump 83 gradually applies negative pressure to half of the closed system 202 behind the diaphragm 13. This causes the diaphragm 13 to extend away from the breast, and thus the diaphragm 13 conveys a decrease in pressure into the breast shield 7. The reduced pressure encourages milk expression from the breast, which is directed through the tortuous labyrinth system 95 and the one-way valve 37 to the collection bottle 3.

While in the depicted embodiment the air exhaust 83B is not used, it may be used for functions including, but not limited to, cooling of electrical components, inflation of the bottle to determine milk volume (discussed further later) or inflation of a massage bladder or liner against the breast. This massage bladder may be used to help mechanically encourage milk expression. More than one massage bladder may be inflated regularly or sequentially to massage one or more parts of the breast. Alternatively, the air pump may be used to provide warm air to one or more chambers configured to apply warmth to one or more parts of the breast to encourage let-down.

The air side 202 further comprises a two-way solenoid valve 103 connected to a filtered air inlet 105 and the pump 83. Alternatively, the filter could be fitted on the pump line 83A. If the filter is fitted here, all intake air is filtered but the performance of the pump may drop. After the negative pressure has been applied to the user's breast, air is bled into the system 202 through the valve 103 in a second phase of the expression cycle. In this embodiment, the air filter 105 is affixed to this inlet to protect the delicate components from degradation. In particular, in embodiments with piezoelectric components, these are particularly sensitive.

The second phase of the expression cycle and associated switching of valve 103 is actioned once a predefined pressure threshold has been reached. The pressure is detected by a pressure sensor 101.

Figure 11:
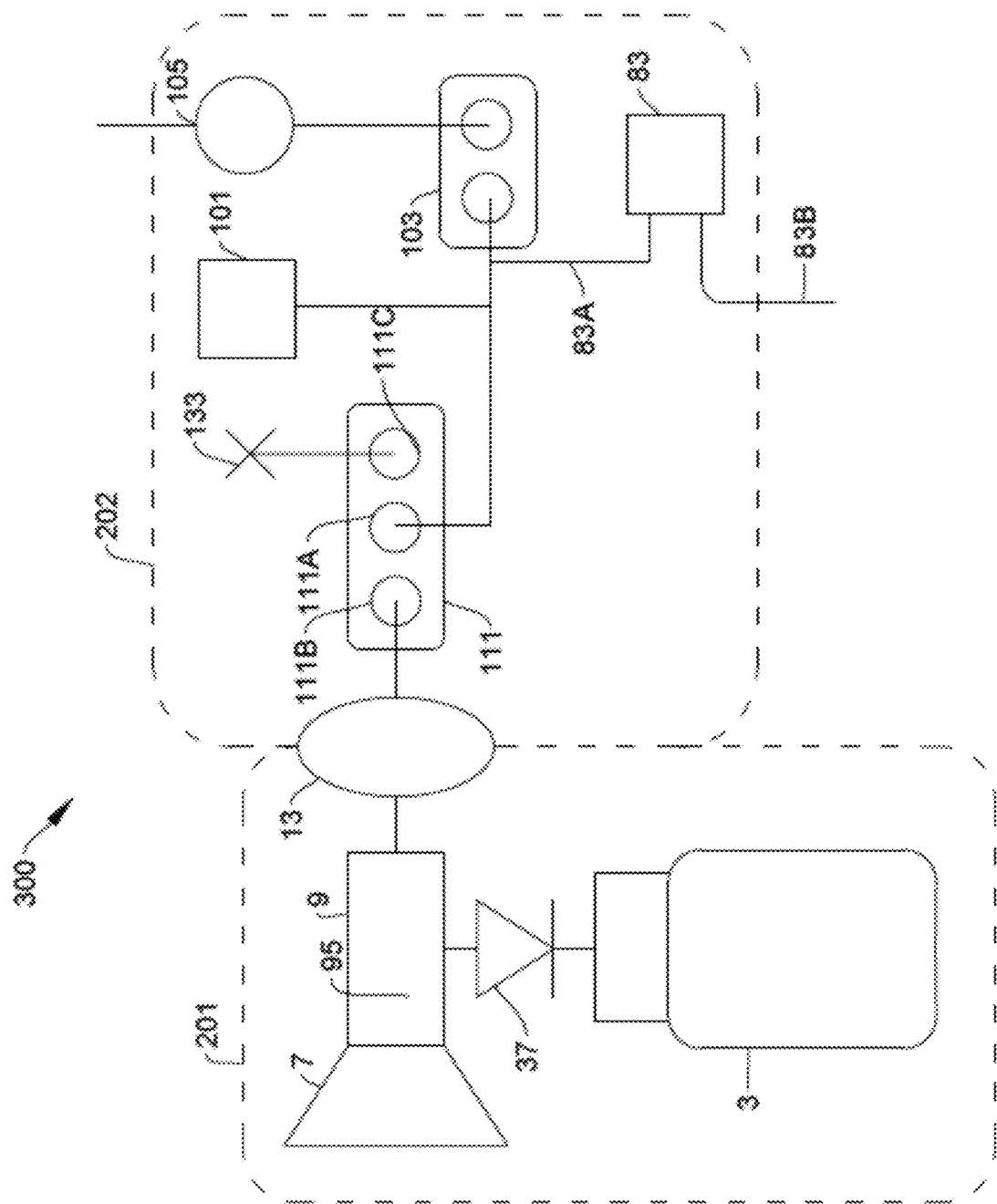
FIG. 11 is a schematic of an alternative pneumatic system for a breast pump system.

In certain embodiments, if the elasticity and extension of the diaphragm 13 may be approximated mathematically at different pressures, the pressure measured by sensor 101 can be used to infer the pressures exposed to the nipple on the opposite side of the diaphragm 13. FIG. 11 shows an alternative pneumatic system 300. The core architecture of this system is the same as the system shown in FIG. 10.

In this system 300, the closed loop 202 is restricted with an additional three way solenoid valve 111. This valve 111 allows the diaphragm 13 to be selectively isolated from the rest of the closed loop 202. This additional three way valve 111 is located between the diaphragm 13 and the pump 83. The pressure sensor 101 is on the pump 83 side of the three way valve 111. The three way valve 111 is a single pole double throw (SPDT) valve, wherein: the pole 111A is in pneumatic connection with the pump 83 and pressure sensor, one of the throws 11 is in pneumatic connection with the diaphragm 13; and the other throw 111C is in pneumatic connection with a dead-end 113. This dead-end 113 may either be a simple closed pipe, or any component(s) that does not allow the flow of air into the system 202. This could include, for example, an arrangement of one-way valves.

In this system 300, therefore, the pump 83 has the option of applying negative pressure directly to the pressure sensor 101. This allows repeated testing of the pump in order to calibrate pump systems, or to diagnose issues with the pump in what is called a dead end stop test. This is achieved by throwing the valve to connect the pump 83 to the dead end 113. The pump 83 then pulls directly against the dead end 113 and the reduction of pressure within the system can be detected by the pressure sensor 101.

The pressure sensor detects when pressure is delivered and is then able to measure the output of the pumping mechanism. The results of the pressure sensor are then sent to an external database for analysis such as a cloud database, or are fed back to an on-board microcontroller that is located inside the housing of the breast pump system.

Based on the pressure sensor measurements, the breast pump system is able to dynamically tune the operation of the pumping mechanism (i.e. the duty or pump cycle, duration of a pumping session, the voltage applied to the pumping mechanism, the peak negative air pressure) in order to ensure a consistent pressure performance across different breast pump systems.

In addition, the breast pump system, using the pressure sensor measurements, is able to determine if the pump is working correctly, within tolerance levels. Material fatigue of the pump is therefore directly assessed by the breast pump system. Hence, if the output of the pumping mechanism degrades over time, the breast pump system can tune the pumping mechanism operation accordingly. As an example, the breast pump system may increase the duration of a pumping session or the voltage applied to the pumping mechanism to ensure the expected pressures are met.

This ensures that the user experience is not altered, despite the changing output of the pump as it degrades over time. This is particularly relevant for piezo pumps where the output of the pump may vary significantly.

The microcontroller can also be programmed to deliver pre-set pressure profiles. The pressure profiles may correspond to, but not necessarily, any suction patterns that would mimic the sucking pattern of an infant. The patterns could mimic for example the sucking pattern of a breastfed infant during a post birth period or at a later period in lactation.

The profiles can also be manually adjusted by the user using a control interface on the housing of the breast pump system or on an application running on a connected device.

Additionally, the user is able to manually indicate the level of comfort that they are experiencing when they are using the system. This can be done using a touch or voice-based interface on the housing of the breast pump system itself or on an application running on a connected device.

The system stores the user-indicated comfort levels together with associated parameters of the pumping system. The pressure profiles may then be fine scaled in order to provide the optimum comfort level for a particular user.

The profiles or any of the pumping parameters may be calculated in order to correlate with maximum milk expression rate or quantity.

The pressure profiles or any of the pumping parameters may also be dynamically adjusted depending on the real time milk expression rate or quantity of milk collected.

The pressure profiles or any of the pumping parameters may also be dynamically adjusted when the start of milk let-down has been detected.

Additionally, the system is also able to learn which parameters improve the breast pump system efficiency. The system is able to calculate or identify the parameters of the pumping mechanism that correlate with the quickest start of milk let-down or the highest volume of milk collected for a certain time period. The optimum comfort level for a particular user may also be taken into account.

Figure 12:
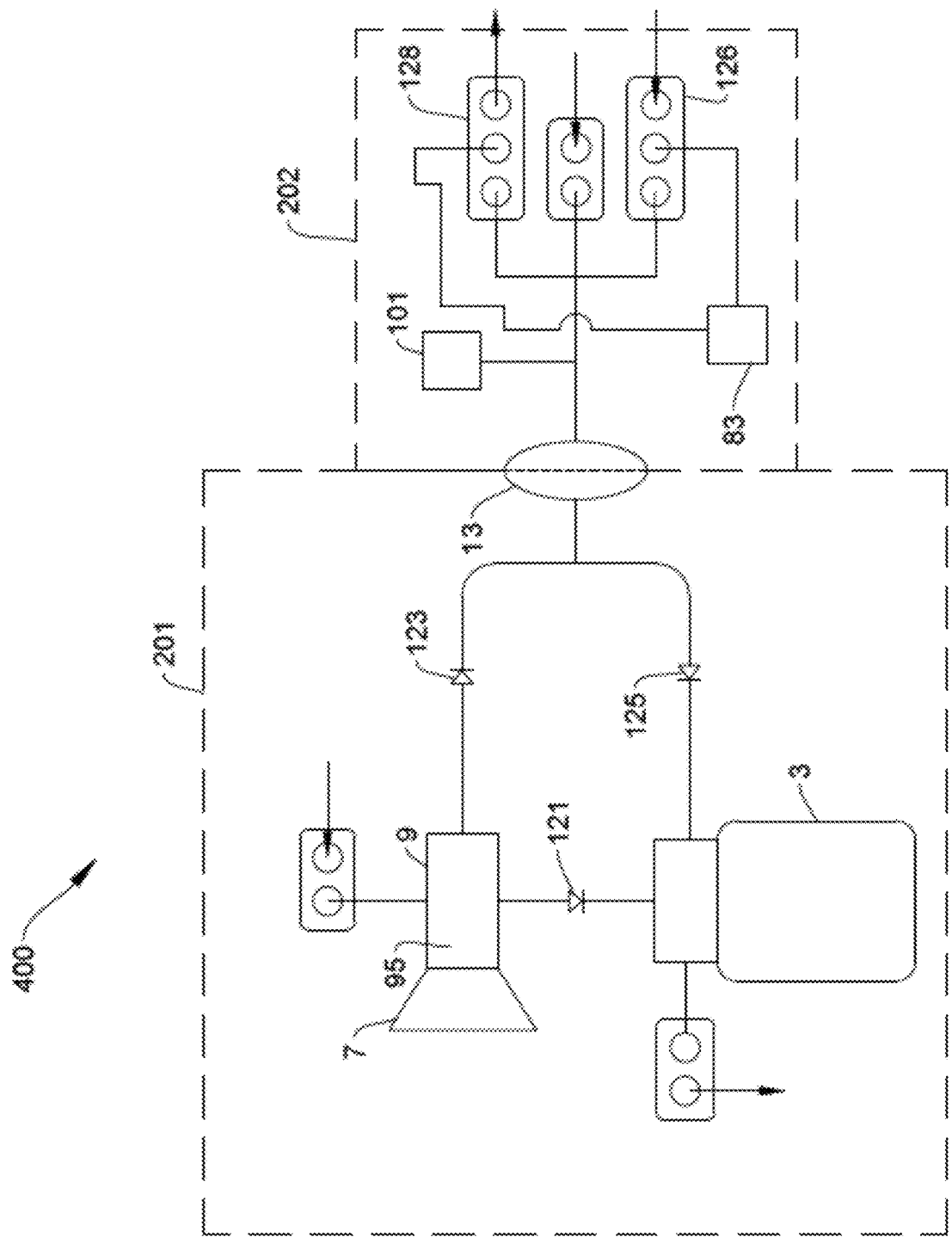
FIG. 12 is a schematic of a further alternative pneumatic system for a breast pump system.

FIG. 12 shows a schematic for a system 400 for a breast pump 100 which can estimate the volume of milk collected in the collection container 3 from data collected on the air-side part 202 of the system 400.

The pump 83 is connected to the circuit via two bleed valves 126, 128. The first bleed valve 126 is arranged to function when the pump 83 applies a negative pressure. As such, this valve 126 is connected to a "bleed in" 127, for supplying atmospheric air to the system 202.

The second bleed valve 128 is arranged to function when the pump 83 applies a positive pressure. As such, this valve 128 is connected to a "bleed out" 129 for bleeding air in the system 202 to the atmosphere.

Although Section C describes the preferred embodiment for measuring or inferring the volume of milk collected in the milk collection container using IR sensors, an alternative method for measuring or inferring the volume of milk collected in the milk collection container using pressure sensors is described also below.

During a milking pump cycle, the pump 83 applies negative pressure on the air side 13B of the diaphragm 13 which causes its extension towards the pump 83. This increases the volume of the space on the milk side 13B of the diaphragm 13. This conveys the decrease in pressure to the breast to encourage expression of milk. A set of three non-return valves 121, 123, 125 ensure that this decrease in pressure is applied only to the breast (via the breast shield 7) and not the milk collection container 3. To measure the volume of milk collected in the container 3, the pump 83 is used instead to apply positive pressure to the diaphragm 13. The diaphragm 13 is forced to extend away from the pump 83 and conveys the pressure increase to the milk side 201 of the system 400. The three non-return valves 121, 123, 125 ensure that this increase in pressure is exclusively conveyed to the milk collection container 13.

The breast pump may further comprise: a first non-return valve between the milk flow side of the diaphragm and the breast shield, configured to allow only a negative pressure to be applied to the breast shield by the pump; a second non-return valve between the milk-flow side of the diaphragm and the milk collection container configured to allow only a positive pressure to be applied to the milk collection container by the pump; and a pressure sensor in pneumatic connection with the pressure-generation side of the diaphragm.

The resulting pressure increase is monitored behind the diaphragm 13 from the air-side 202 by a pressure sensor 101. Preferably, the pressure sensor 101 is a piezoelectric pressure sensor (piezo pressure sensor). The rate at which the pump 83 (at constant strength) is able to increase the pressure in the system 400 is a function of the volume of air that remains in the milk collection container 3. As air is many times more compressible than liquid, the rate at which pressure increases in the system 400 can be expressed as an approximate function of the volume of milk held in the collection container 3.

Figure 13:
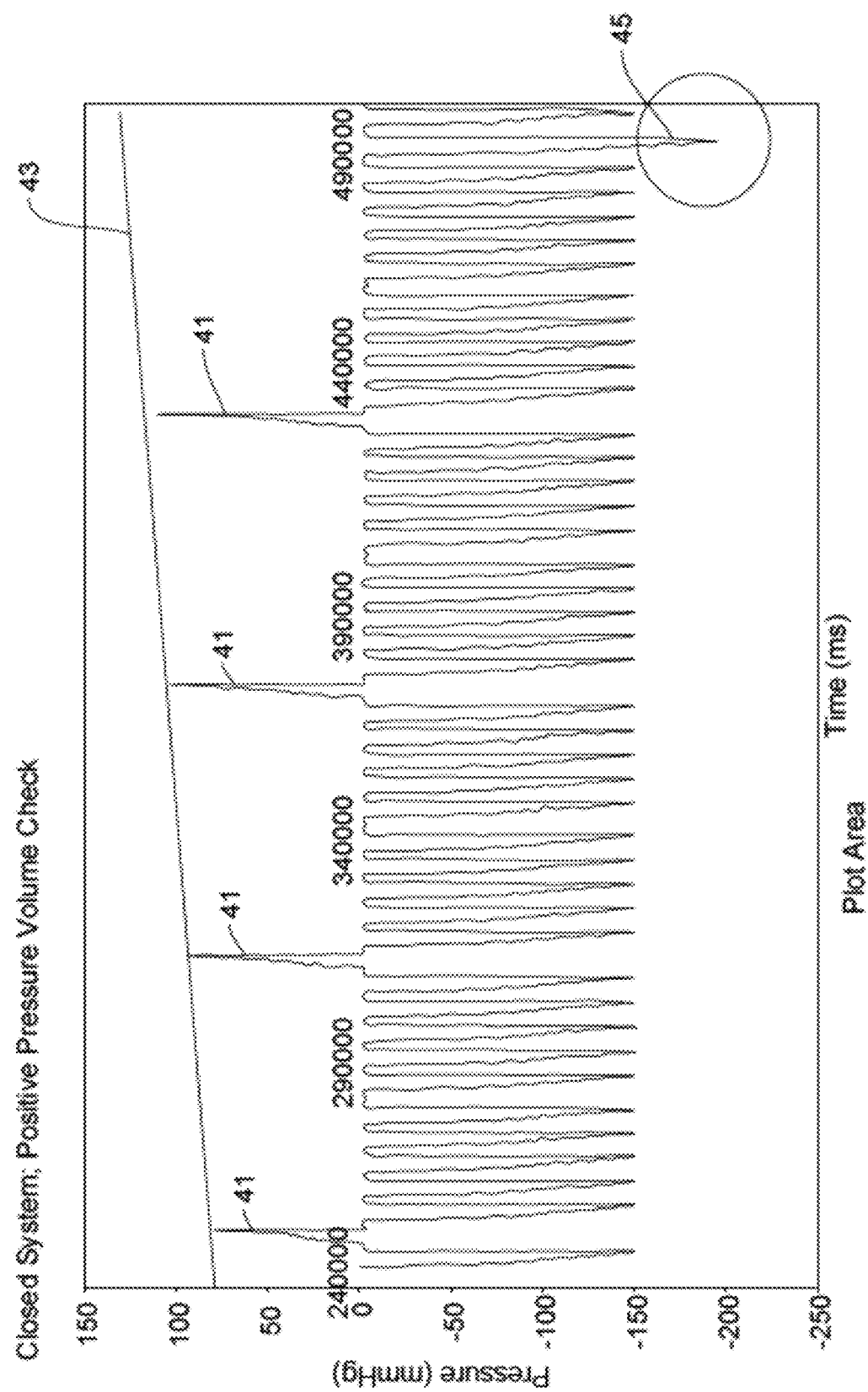
FIG. 13 is a graph depicting measured pressure in the breast pump system of FIG. 12 over time.

Thus by increasing the pressure in this fashion, the rate of pressure increase can be determined, from which the volume of milk held in the container 3 is calculable. FIG. 13 shows repeated milking and volume measurement cycles as the collection container 3 is filled. To determine the rate of pressure increase the pump 83 was run for a fixed time.

As pumping proceeds and the volume of air reduces in the system 400, the pump 83 is able to achieve a higher pressure. Each milking cycle is represented by a positive pressure spike 41. There is a clear upwards trend 43 in magnitude of positive pressures achieved as the collection container 3 is filled.

A method of estimating the pressure applied by a breast pump may comprise the steps of: selecting a pressure cycle from a pre-defined list of pressure cycles; applying pressure with the pump to stimulate milk expression; reading the output of the pressure sensor, and adjusting the applied pressure of the pump to match the pressure profile selected.

This allows for repeatable application of force to the breast, even as the pump performance degrades.

Preferably the method further comprises the steps of: approximating the elasticity and extension of the diaphragm at the relevant pressure; and calculating an estimated applied pressure based upon the output of the pressure sensor and the approximated elasticity and extension of the diaphragm.

Alternatively, a method of estimating the milk collected by a breast pump may comprise the steps of: generating a positive pressure with the pump; transmitting the positive pressure via the diaphragm and second non-return valve to only the milk collection container, measuring the increase in pressure by the pressure sensor in pneumatic connection with the diaphragm; estimating the volume of milk inside the milk collection container based upon the rate of increase of pressure. In this manner, the volume of milk can be estimated remotely.

In this manner, an estimate can be obtained for the volume of milk in the container 3 based upon the measured pressures.

FIG. 13 also shows a dead end stop pump test 45 as described above. The negative spike shows the application of negative pressure directly to the pressure sensor 101.

2. Breast Shield Sizing and Nipple Alignment

The correct sizing of the breast shield and the alignment of the nipple in the breast shield are key for an efficient and comfortable use of the breast pump. However breast shape, size as well as nipple size and position on the breast vary from one person to another and one breast from another. In addition, women's bodies often change during the pumping life cycle and consequently breast shield sizing may also need to be changed. Therefore, a number of breast shield sizes are available. Guide lines for correct nipple alignment are also provided.

Figure 14:
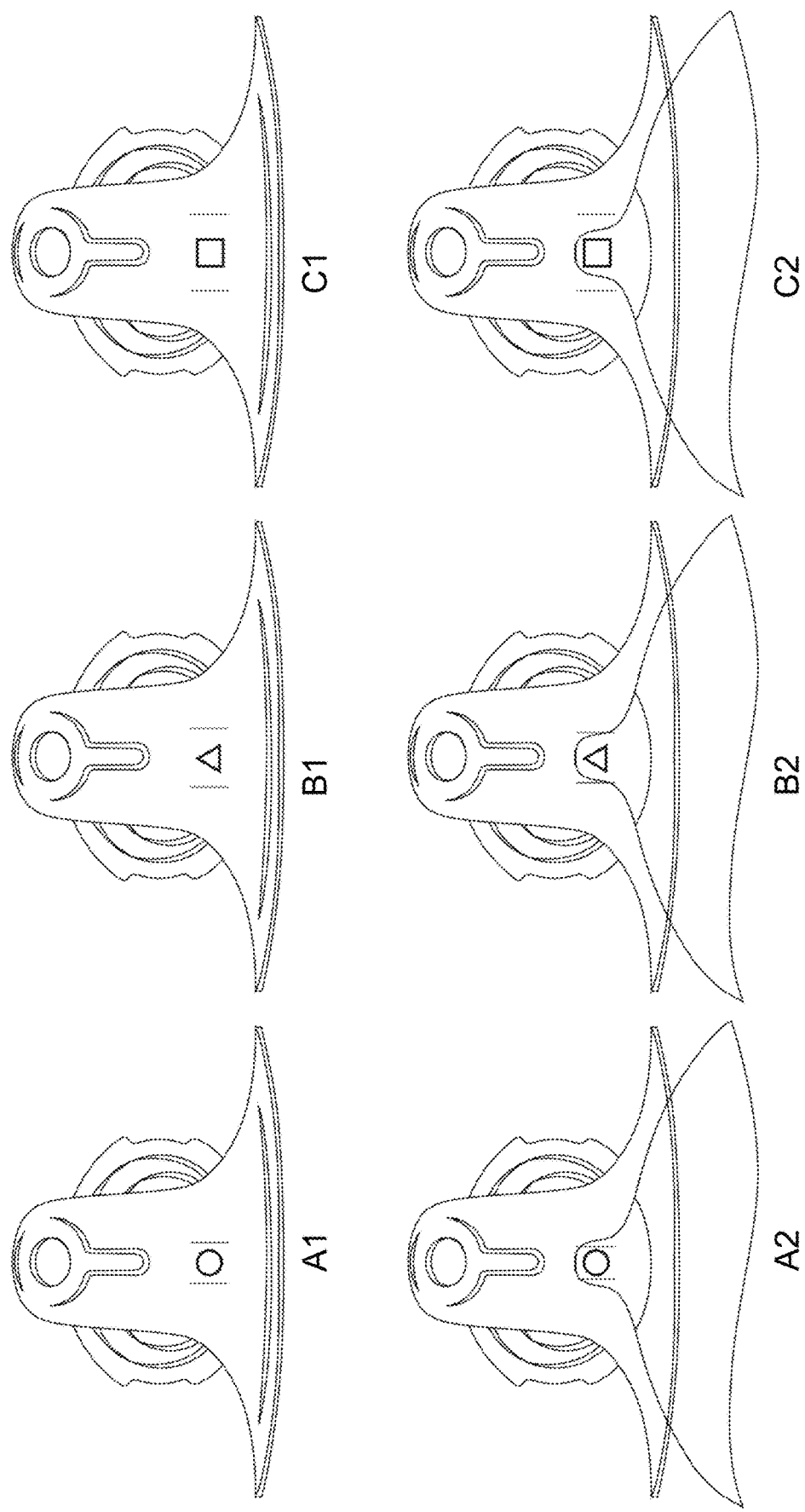
FIG. 14 shows schematics for breast shield sizing and nipple alignment.

With reference to FIG. 14, three breast shield sizes are shown (A1, B1, C1). The substantially clear breast shield gives an unobstructed view of the breast and allows a user to easily confirm that she has the appropriate sized shield for her breast.

In order to determine the correct breast shield size and nipple alignment, the breast shield and the diaphragm are detached from the housing and placed on the breast with the sizing symbol facing upwards (with the diaphragm positioned below the nipple) and the nipple aligned in the centre of the fit lines (as shown in A2, B2, C2). The transparent breast shield allows the user to observe the nipple while adjusting the position of the breast shield in order to align the nipple correctly near the centre of the breast shield nipple tunnel. Prior to using the pump, the nipple is aligned correctly, and the breast shield is pushed into place ensuring the seal is correctly positioned on the breast shield. The fit lines should be directly aligned with the outside of the nipple. The correct alignment is illustrated B2.

When the nipple is correctly aligned, the user then rotates the breast shield in order for the diaphragm to be positioned on top of the nipple. The user may then quickly assemble the rest of the breast pump (i.e. the housing and the milk container) on the breast shield via a one-click attachment mechanism confirming correct engagement, which may be performed one-handed. Nipple alignment may therefore be easily maintained. Audio and/or haptic feedback may also be provided to further confirm correct engagement.

3. Connected Device Application

FIGS. 15 to 20 show examples of screenshots of a connected device application that may be used in conjunction with the breast pump system as described above. The interface shown here is an example only and the same data may be presented via any conceivable means including animated graphics, device notifications, audio or text descriptions.

Figure 15:
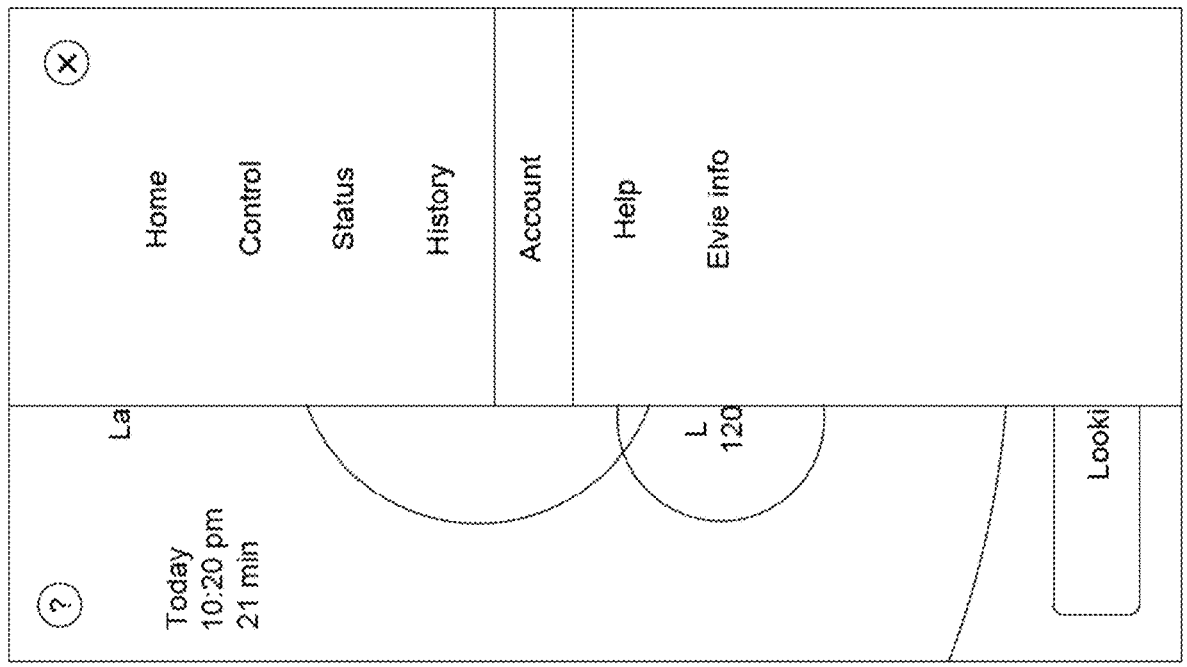
FIG. 15 shows a screenshot of an application running on a device connected to the breast pump system.

FIG. 15 shows a homepage of the application with different functions provided to the user which can be accessed either directly while pumping or at a later time in order for example: to review pump settings or the history of previous pumping sessions.

Figure 16:
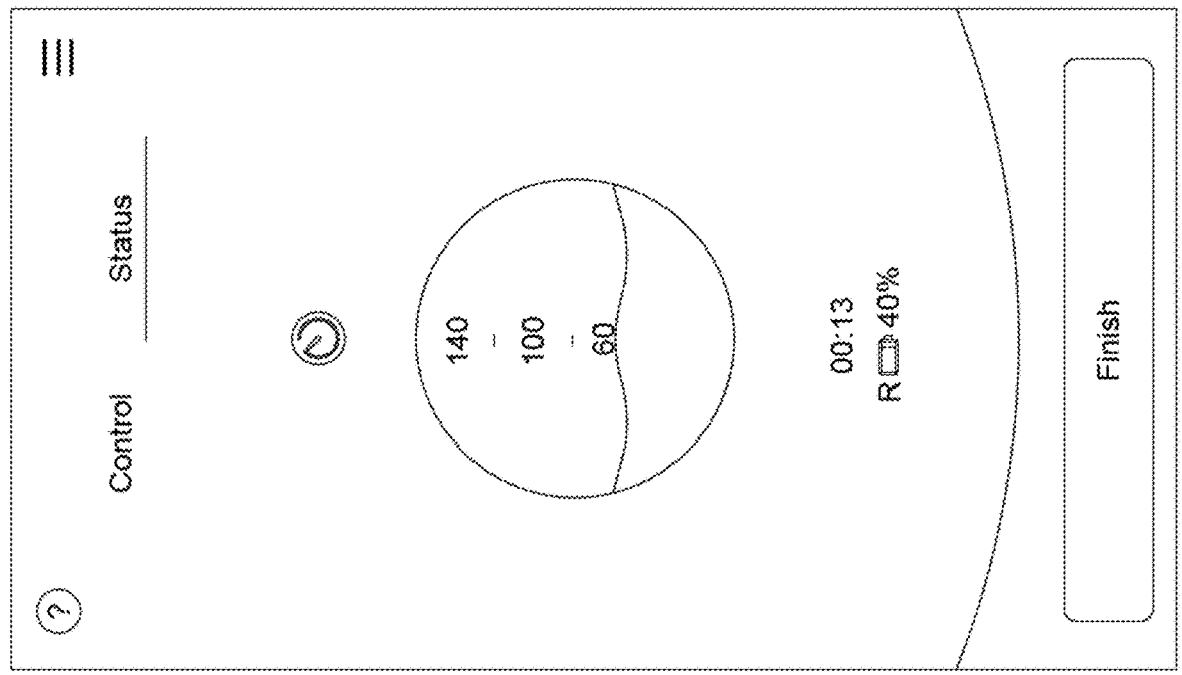
FIG. 16 shows a screenshot of an application running on a device connected to the breast pump system.

FIG. 16 shows a status page with details of remaining battery life, pumping time elapsed and volume of milk inside the milk container.

Figure 17:
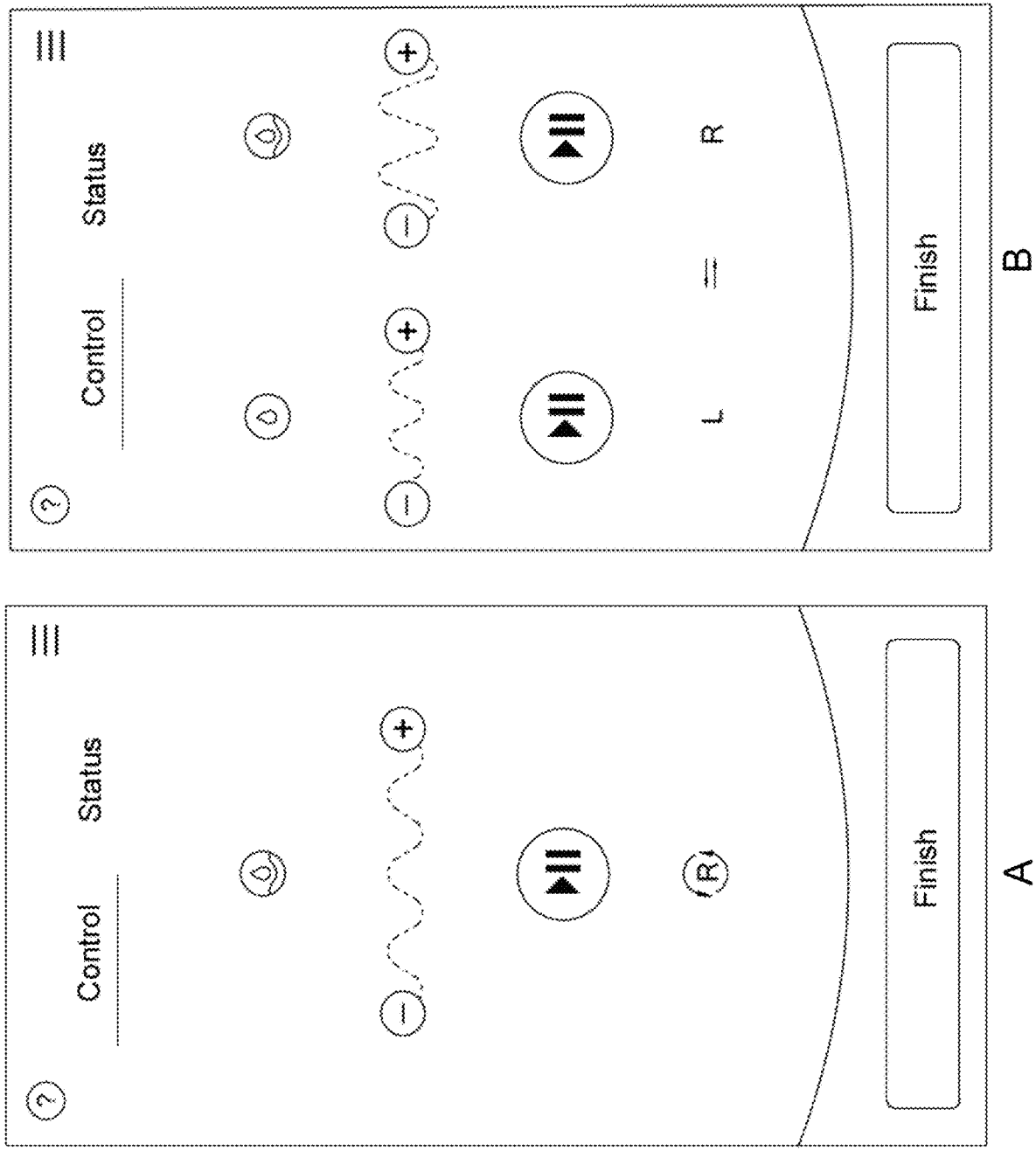
FIG. 17 shows a screenshot of an application running on a device connected to the breast pump system.

FIG. 17 shows screenshots of a control page, in which a user is able to control different pump parameters for a single breast pump (A) or two breast pumps (B). The user may press on the play button to either start, pause, or resume a pumping activity. The user may also directly increase or decrease the rate of expression using the (+) or (−) buttons. When only one breast is being pumped (A), the user may also indicate if it is either the right or left breast that is being pumped. The user may also control the pump peak pressure or alternatively may switch between different pre-programmed pressure profiles such as one mimicking the sucking pattern of a baby during expression or stimulation cycle.

Figure 18:
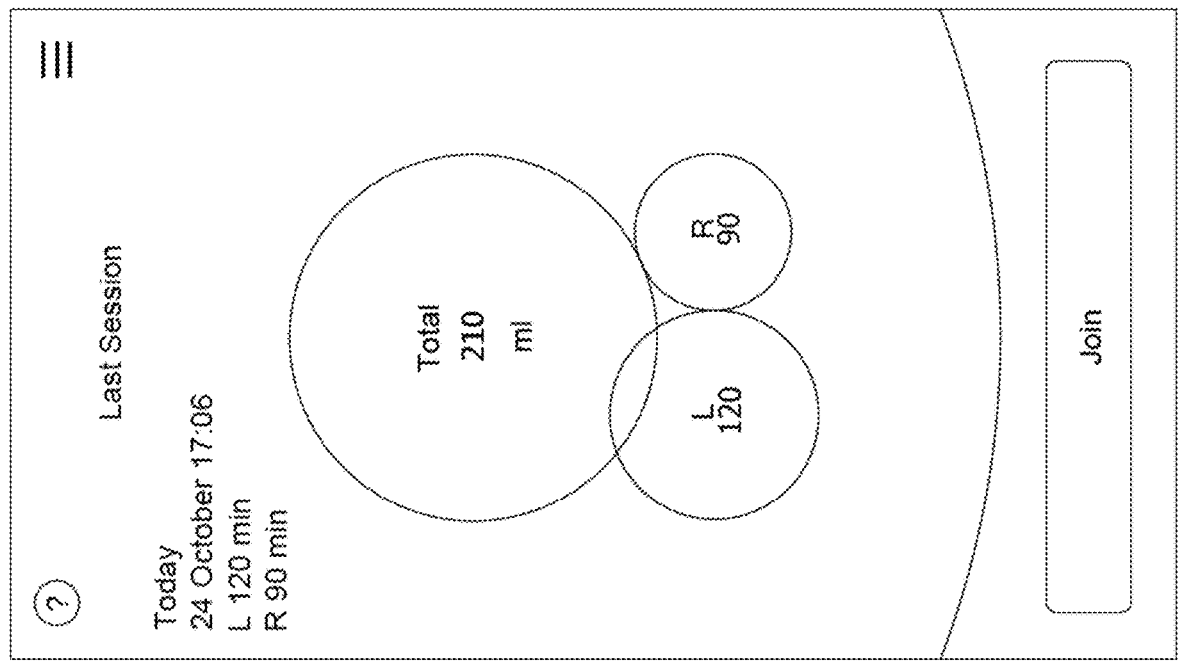
FIG. 18 shows a screenshot of an application running on a device connected to the breast pump system.

FIG. 18 shows a page providing a summary of the last recorded pumping session.

Figure 19:
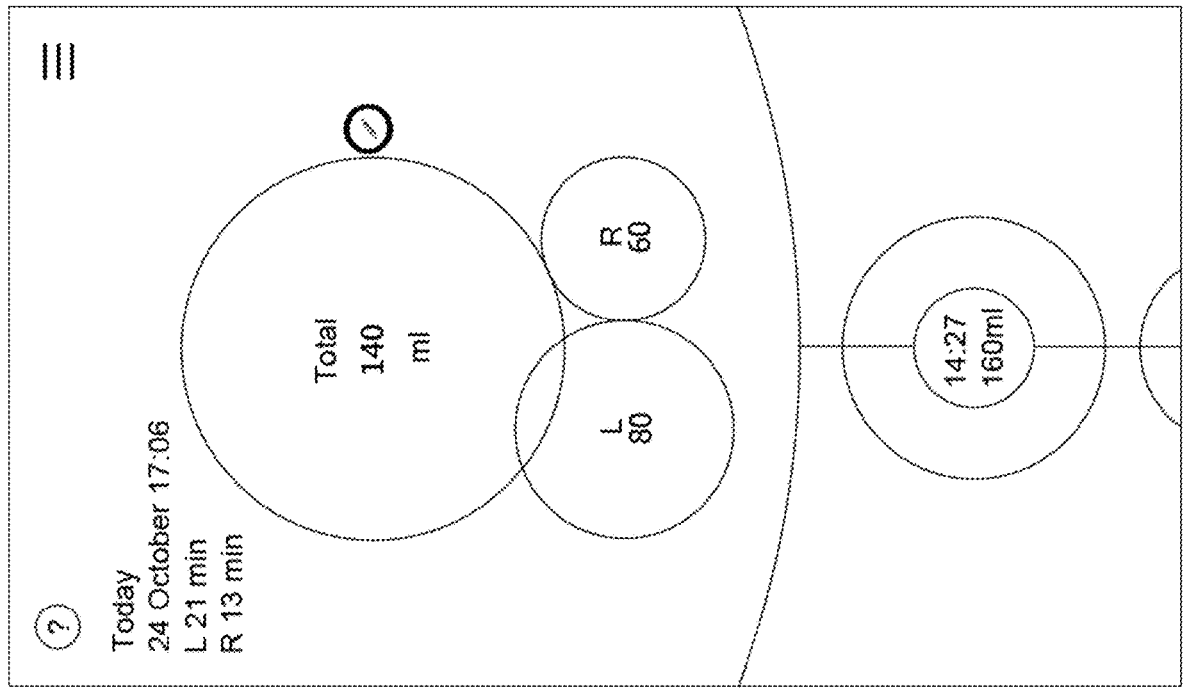
FIG. 19 shows a screenshot of an application running on a device connected to the breast pump system.

FIG. 19 shows a page providing a history of previous pumping sessions. The user may scroll down through the page and visualize the data related to specific pumping sessions as a function of time.

Figure 20:
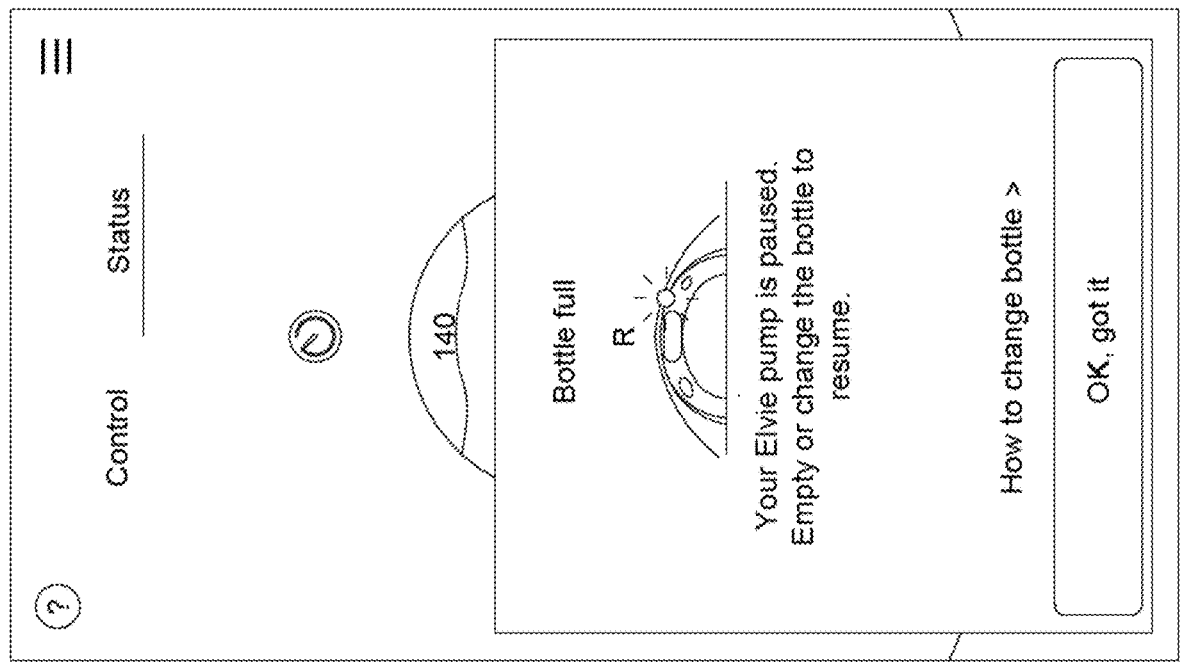
FIG. 20 shows a screenshot of an application running on a connected device.

The application is also capable of providing notifications relating to pumping. FIG. 20 shows a screenshot of the application, in which a user is provided a notification when the milk collection bottle is full. Other generated notifications may include warnings about battery life, Bluetooth connection status or any other wireless communication status, status of miss-assembly, excessive movement or lack of expression.

Figure 21:
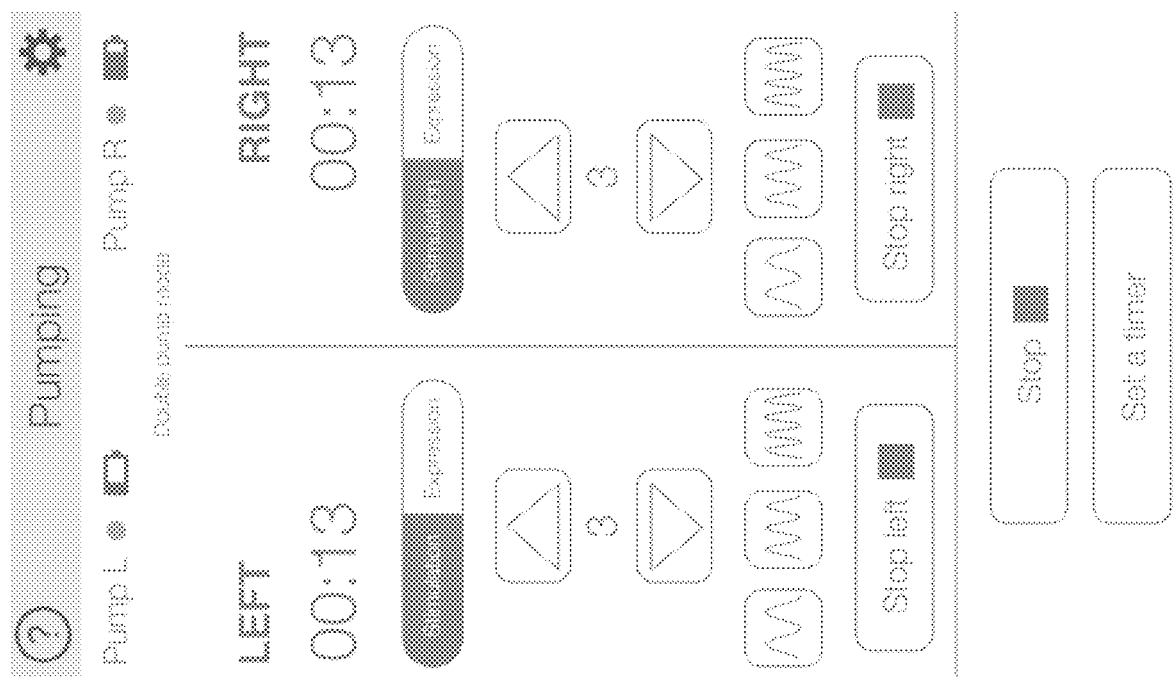
FIG. 21 shows a screenshot of an application running on a connected device.
Figure 22:
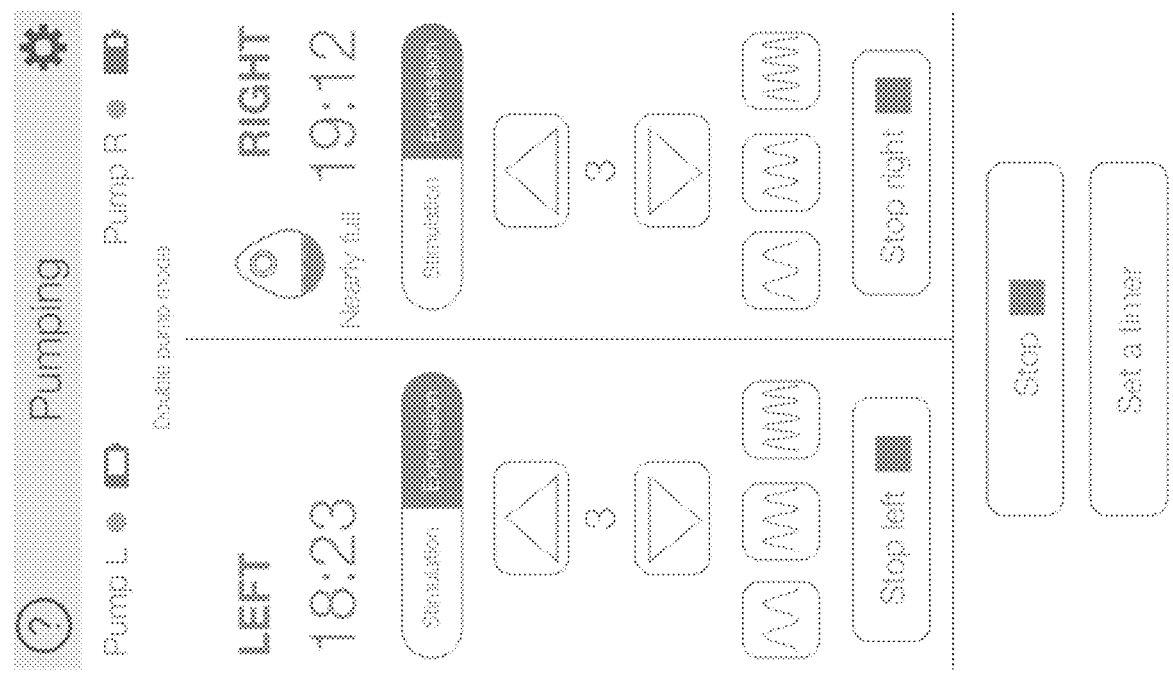
FIG. 22 shows a screenshot of an application running on a connected device.

FIG. 21 shows a further example with a screenshot of an application running on a connected device. The page shows the pumping status when a user is using a double pump mode of operation with a pump on each breast. The user is able to manually control each pump individually and may start, stop or change a pumping cycle, increase or decrease each pump peak pressure, or switch between different pre-program pressure profiles such as one mimicking the sucking pattern of a baby during an expression or stimulation cycle. The application also notifies the user when a milk collection container is nearly full as shown in FIG. 22.

Figure 23:
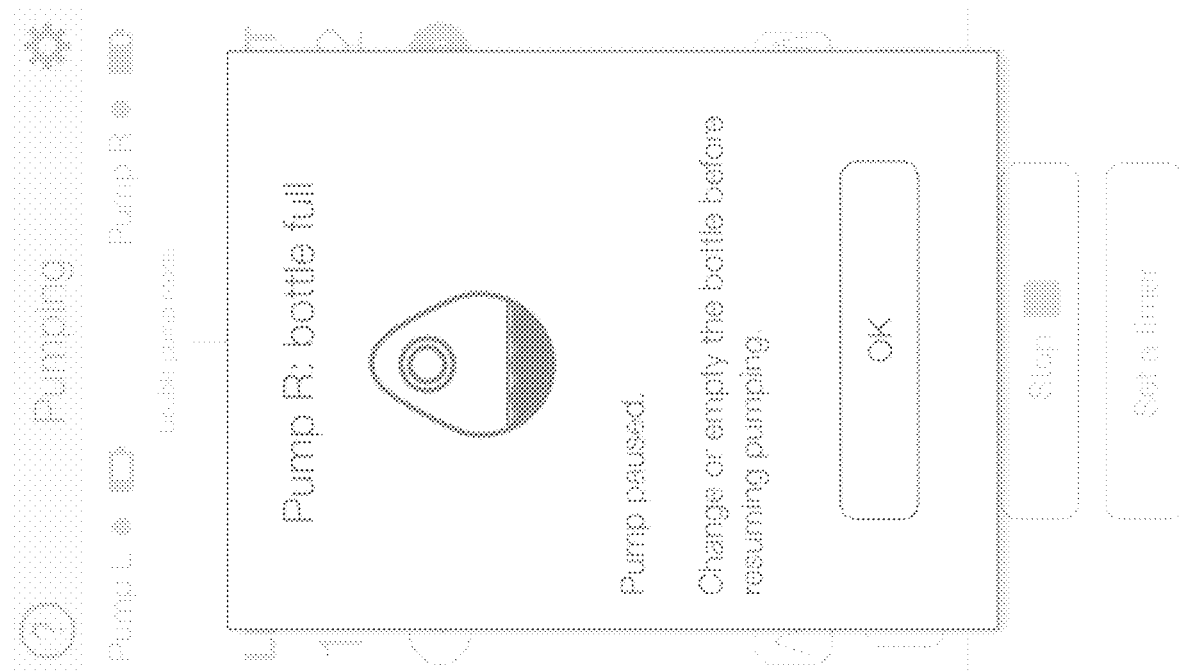
FIG. 23 shows a screenshot of an application running on a connected device.

FIG. 23 shows a status page with an alert notifying the user that the milk collection container of the pump on the right breast is full. A message is displayed that the pump session has paused and that the milk collection container should be changed or emptied before resuming pumping.

Figure 24:
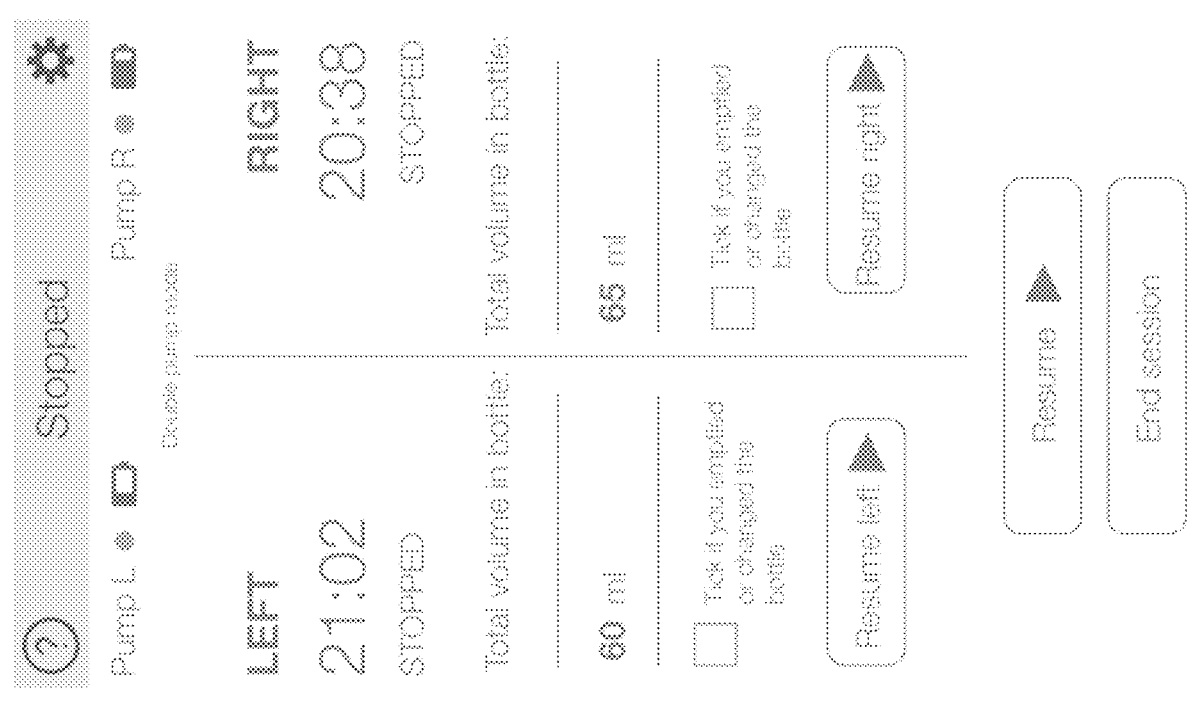

With reference to FIG. 24, when the left and right pump are stopped or paused, the application displays the elapsed time since the start of each session (right and left), the total volume of milk collected in each bottle.

Figure 25:
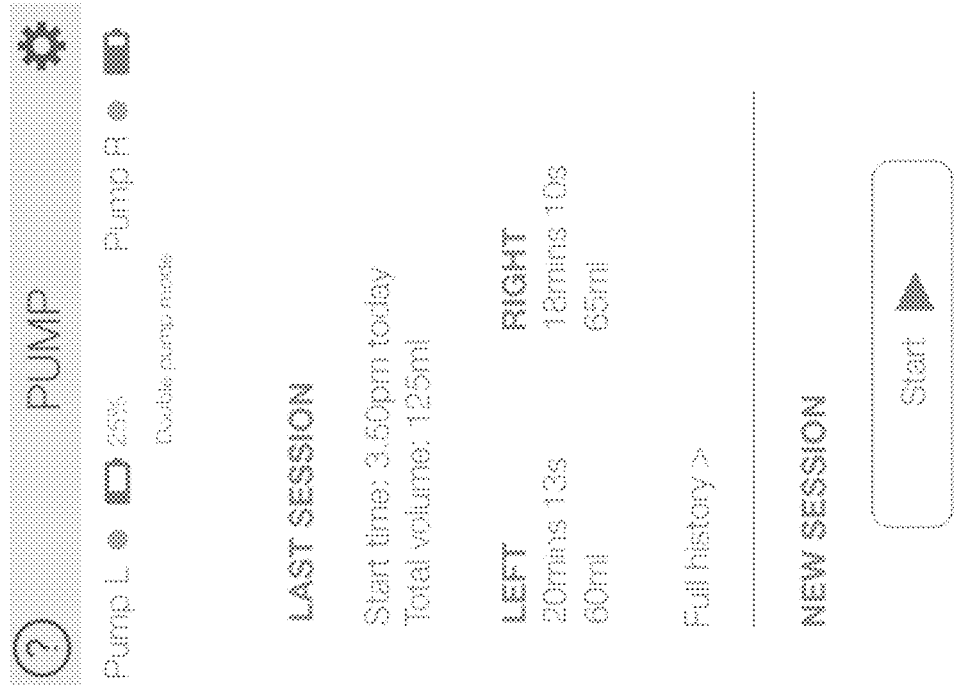
FIG. 25 shows a screenshot of an application running on a connected device.

With reference to FIG. 25, a page summarising the last session (with a double pump mode) is displayed.

In addition to the data provided to the user, and their interactions with the application, the app will also hold data that the user does not interact with. For example, this may include data associated with pump diagnostics. In addition to all functions and sources of data discussed above, the application may itself generate metadata associated with its use or inputs, notes or files uploaded by the user. All data handled within the mobile application can be periodically transferred to a cloud database for analysis. An alternative embodiment of the breast pump system may include direct contact between the database and the pump, so that pumping data may be conveyed directly, without the use of a smartphone application.

In addition to providing data to the cloud, the application may also provide a platform to receive data including for example firmware updates.

4. Breast Pump Data Analysis

The discreet, wearable and fully integrated breast pump may offer live expression monitoring and intelligent feedback to the user in order to provide recommendations for improving pump efficiency or performance, user comfort or other pumping/sensing variables, and to enable the user to understand what variables correlate to good milk flow.

Examples of variables automatically collected by the device are: time of day, pump speed, pressure level setting, measured pressure, pressure cycle or duty cycle, voltage supplied to pumps, flow rate, volume of milk, tilt, temperature, events such as when let-down happens, when a session is finished. The user can also input the following variables: what side they have pump with (left or right or both), and the comfort level.

This is in part possible because the live milk volume measurement system functions reliably (as discussed in Section B). The breast pump system includes a measurement sub system including IR sensors that measures or infers milk flow into the milk container, and that enables a data analysis system to determine patterns of usage in order to optimally control pumping parameters. The generated data may then be distributed to a connected device and/or to a cloud server for analysis in order to provide several useful functions.

Figure 26:
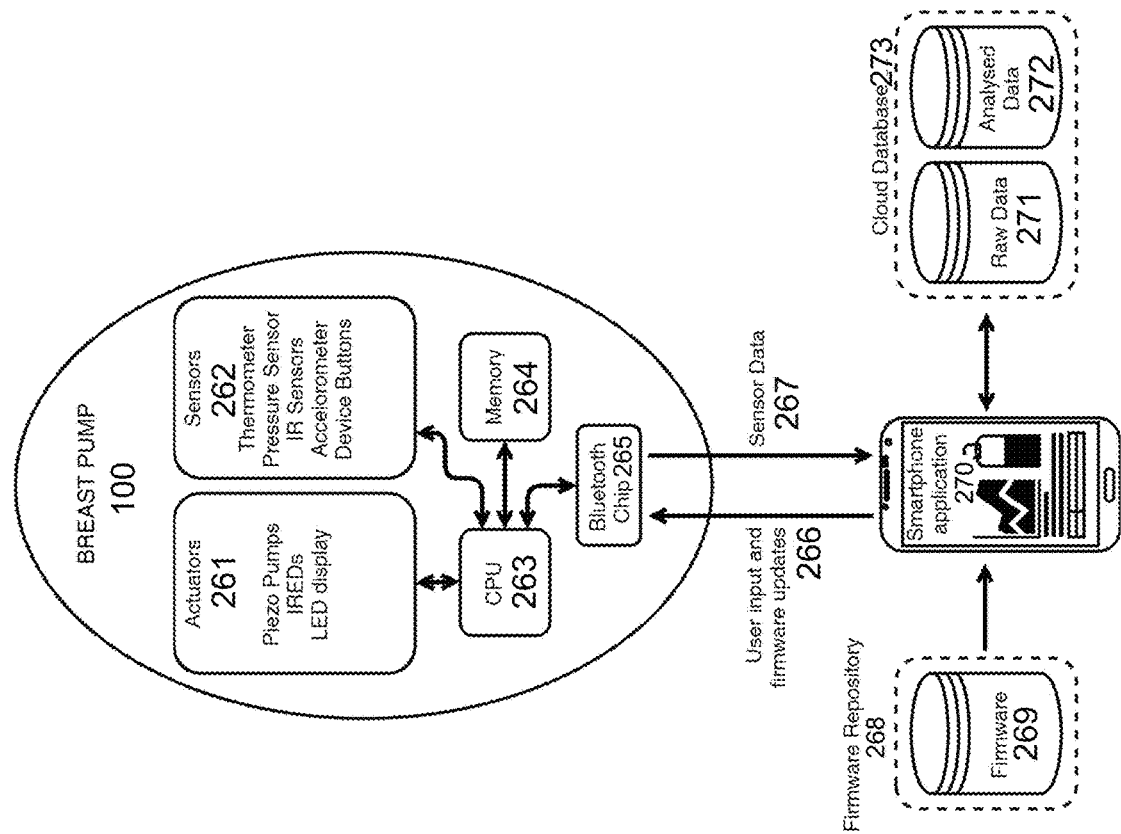
FIG. 26 shows a diagram of a breast pump sensor network.

FIG. 26 illustrates an outline of a smart breast pump system network which includes the breast pump system (100) in communication with a peripheral mobile device and application (270) and several cloud-based databases (268, 273). The breast pump system (100) includes several sensors (262). Sensor data refers to a broad definition including data generated from any sensor or any other analogue/digital reading directly from the motherboard or any other component. However, within the embodiment detailed, these measurements include one or more of the following, but not limited to: milk volume measurements, temperature sensor readings, skin temperature sensing, pressure sensor readings, accelerometer data and user inputs through any physical device interface.

The device also contains a number of actuators, including, but not restricted to: piezoelectric pump(s), solenoid valve(s), IREDs and an LED display. Sensors and actuators within the device are coordinated by the CPU (263). In addition, any interactions, and data from these components, may be stored in memory (264).

Further to these components, the device also contains a communication chip, such as a Bluetooth chip (265) which can be used to communicate wirelessly with connected devices such as a peripheral mobile device (270). Through this connection any sensor data (267) generated in the breast pump can be sent to the connected device. This user data, along with any other metadata generated from a connected device app, can be provided to an online database which aggregates all user data (273). In addition, the communication chip will also allow the sending of user control data/firmware updates from the connected device to the breast pump system (266).

Raw data (271) collected from the measurement sub-system including sensors (262) may be analysed on a cloud database and the analysed data may be stored on the cloud (272). Through inferences provided by the analysed data, firmware updates (269) may be developed. These can be provided for download to the pump through, for example, an online firmware repository or bundled with the companion app in the connected device app store (268).

In addition, it should be appreciated that despite the sophistication of the proposed breast pump network, the breast pump still retains complete functionality without wireless integration into this network. Relevant data may be stored in the device's memory (264) which may then be later uploaded to the peripheral portion of the system when a connection is established, the connection could be via USB cable or wireless.

The measurement sub-system may analyse one or more of the following:
  the quantity of the liquid in the container above its base;
  the height of the liquid in the container above its base;
  the angle the top surface of the liquid in the container makes with respect to a baseline, such as the horizontal.

Based on whether the quantity and/or the height of the liquid in the container above its base is increasing above a threshold rate of increase, a haptic and/or visual indicator indicates if the pump is operating correctly to pump milk. For example, the visual indicator is a row of LEDs that changes appearance as the quantity of liquid increases.

The visual indicator may provide:
  an estimation of the flow rate;
  an estimation of the fill rate;
  an indication of how much of the container has been filled.

As a further example, an accelerometer may infer the amount of movement or tilt angle during a pumping session. If the tilt angle excesses a threshold, the system warns or alerts the user of an imminent spillage, or provides the user with an alert to change position. Alternatively, the system may also stop pumping to prevent spillage, and once the tilt angle reduces below the threshold, pumping may resume automatically. By sensing the movement or title angle during a pumping session, the system may also derive the user's activity such as walking, standing or lying.

Many variables can affect milk expression and data analysis of these multiple variables can help mothers to achieve efficient pumping regimes and improve the overall user experience.

Therefore, the measurement sub-system measures or infers milk flow into the milk container and enables a user to understand what variables (e.g. time of day, pump setting) correlates to good milk flow. The amount of milk expressed over one or more sessions is recorded as well as additional metrics such as: time of day, pump setting, length of a single pumping session, vacuum level, cycle times, comfort, liquids consumed by the mother. Live data or feedback is then provided to the user to ensure the breast pump is being used properly and to support the user in understanding the variables that would correspond to the specific individual optimum use of the breast pump.

Furthermore, live data can be used to automatically and intelligently affect specific pumping parameters in order to produce the most efficient pumping session. For example, if the rate of expression increases, the milking cycle might be adjusted accordingly to achieve a more efficient, or more comfortable pumping cycle.

The measurement sub-system also enables a data analysis system to determine patterns of usage in order to optimally control pumping parameters. Collected metrics are transferred through wireless connections between the pump, a connected device or app and a cloud database. Additionally, the application can also connect to other apps residing on the connected device, such as fitness app or social media app or any other apps. Further metrics may also include the behaviour or specific usage of the user associated with the connected device while using the pump (detection of vision and/or audio cues, internet usage, application usage, calls, text message).

Different aspects of pumping can be automatically changed based on dynamic sensor feedback within the breast pump device. The data analysis system is able to access real-time data of pumping sessions and may be used to perform one or more of the following functions, but not limited to:
  indicate whether the milk is flowing or not flowing,
  measure or infer the quantity and/or height of the liquid in the container above its base,
  give recommendations to the mother for optimal metrics for optimal milk flow,
  give recommendations to the mother for optimal metrics for weaning,
  give recommendations to the mother for optimal metrics for increasing milk supply (e.g. power pumping),
  give recommendations to the mother for optimal metrics if an optimal session start time or a complete session has been missed,
  automatically set metrics for the pumping mechanism, such as length of a single pumping session, vacuum level, cycle times.
  automatically stop pumping when the milk container is full,
  automatically adjust one or more pumping parameters to achieve an optimum pumping session,
  automatically adjust one or more pumping parameters to achieve a comfortable pumping session,
  automatically change the pumping cycle from a programmed cycle to another different programmed cycle, such as from a stimulation cycle to an expression cycle.

In addition, sensor feedback might be used to improve the physical function of the breast pump system itself. For example, an array of piezoelectric pumps may be dynamically adjusted in response to their operating temperatures so as to optimise the total life of the component whist maintaining peak pressures.

Many additional embodiments may be described for these simple feedback systems, yet the premise remains: real-time sensor feedback is used to automatically and dynamically adjust actuator function. Each feedback program may feasibly include any number and combination of data sources and affect any arrangement of actuators.

The data generated can also be used to generate large datasets of pumping parameters, user metadata and associated expression rates, therefore allowing the analysis of trends and the construction of associations or correlations that can be used to improve pumping efficiency, efficacy or any function related to effective milk expression. The analysis of large user datasets may yield useful general associations between pumping parameters and expression data, which may be used to construct additional feedback systems to include on firmware updates.

Multiple data sources can be interpreted simultaneously and several different changes to pumping might be actuated to increase pumping efficiency, user experience or optimize pump performance.

Collected metrics may be anonymised and exported for sharing to other apps, community or social media platforms on the connected device, or to an external products and services, such as community or social media platform. By contrasting the performance of different users in the context of associated metadata, users may be grouped into discrete 'Pumper profiles' or communities, which may then be used to recommend, or action the most appropriate selection of intelligent feedback systems to encourage efficient expression. For example, a higher peak pressure may be recommended for women who tend to move more whilst pumping, so as to achieve more efficient expression.

Section B: IR System

This section describes the milk detecting system used in the Elvie™ pump.

Figure 27:
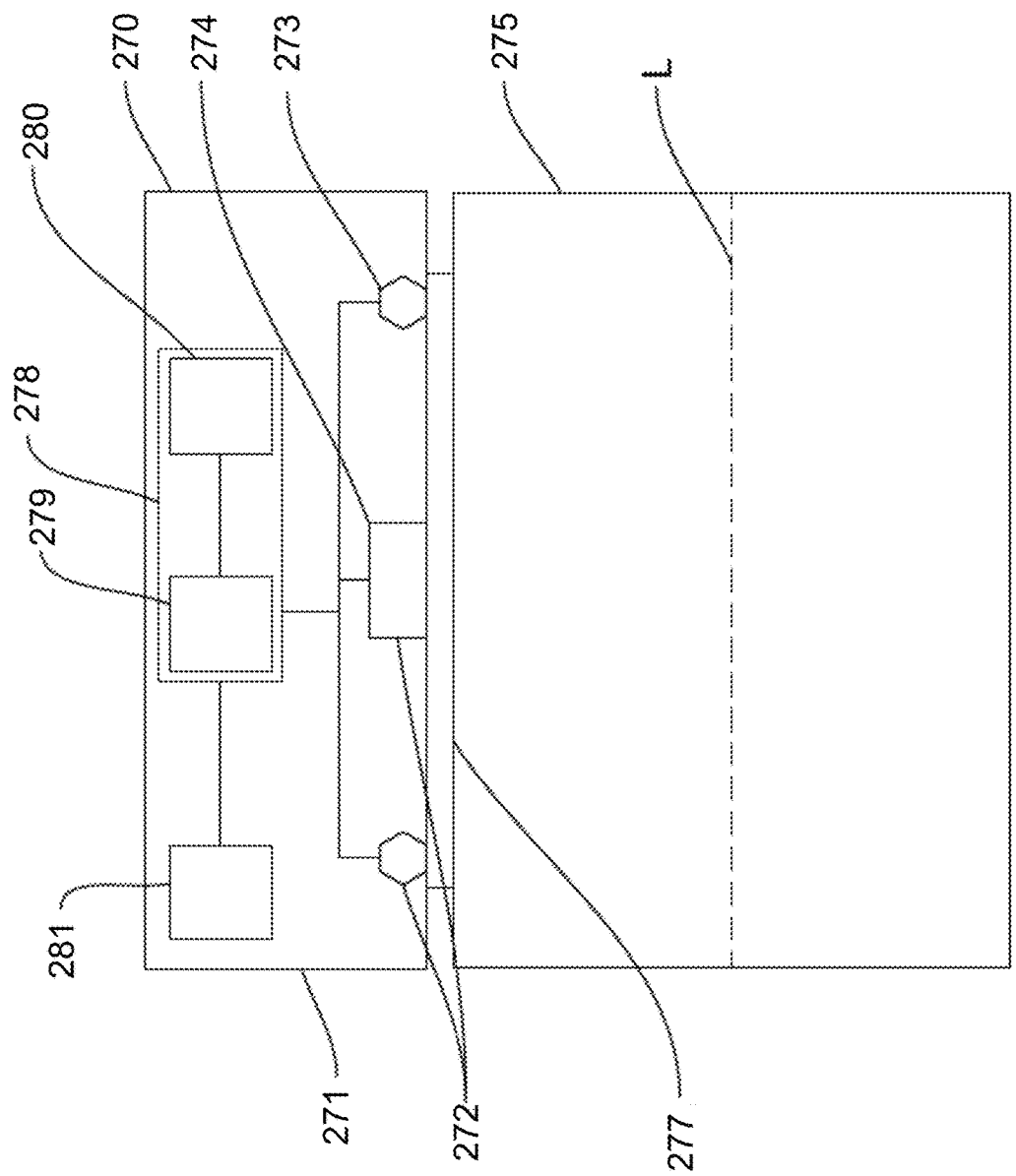
FIG. 27 shows a sectional view of a device being used to determine the level of liquid in a container.
Figure 28:
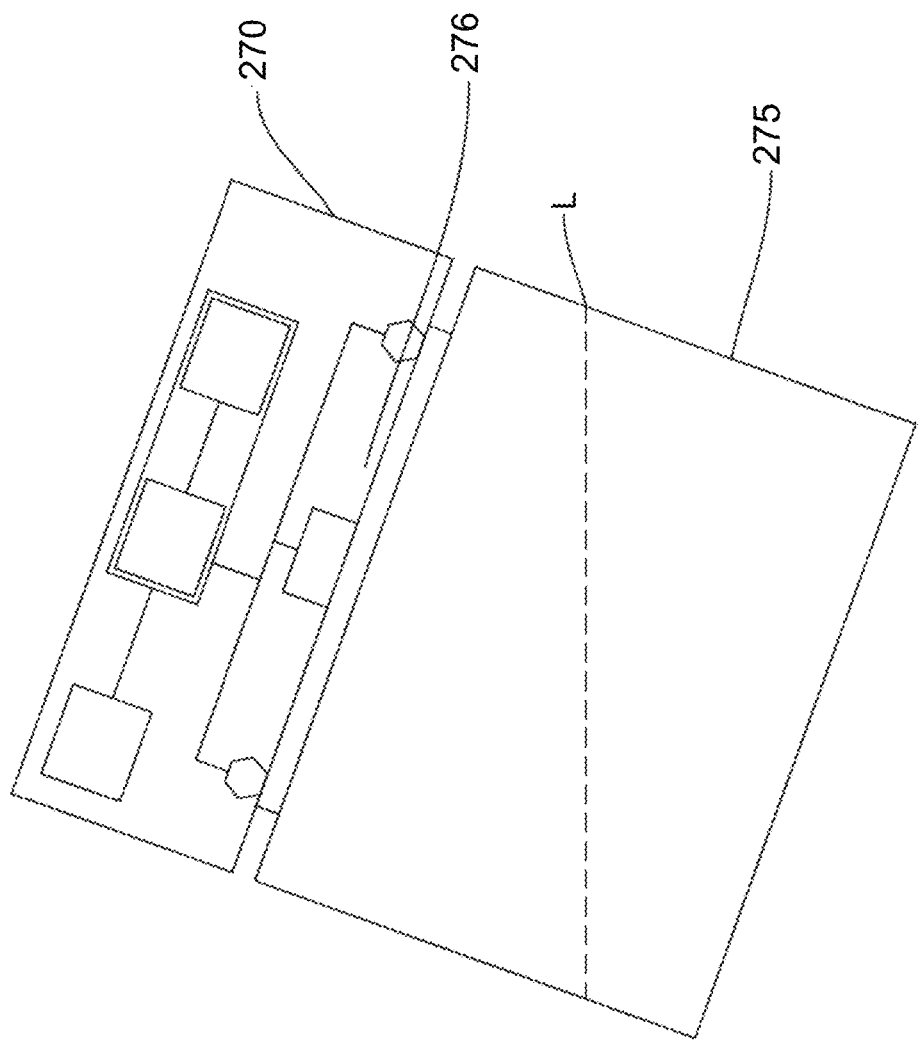
FIG. 28 shows a sectional view of the device and the container from FIG. 27 being used at a different orientation.

With reference to FIGS. 27 and 28, there is shown a device 270 for use in detecting the level of liquid inside a container 275. The device 270 is formed of a housing 271 in which is located a sensing assembly 272 comprising a series of optical emitters 273 (an array of three optical emitters is used on one implementation) which are relative to, and each located at a distance from, an optical receiver 274. In operation of the device as will be described, each optical emitter 273 is operable to emit radiation which is received by the optical receiver 274. In an embodiment of the invention, the series of optical emitters are each located equidistant from the optical receiver 274.

The optical emitters 273 and the optical receiver 274 from the sensing assembly 272 are located in a portion 276 of the device 270 which faces the container 275 when the device is connected to the container 275. The portion 276 of the device 270 containing the optical emitters 273 and the optical receiver 274 comprises a window 277 of material which is transparent to optical radiation. In this way, each of the optical emitters 273 and the optical receiver 274 have a line of sight through the window 277 into the container 275 when the device 270 is connected thereto.

A controller 278 comprising a CPU 279 and a memory 280 is provided in the device 270 for controlling the operation of the sensing assembly 272. An accelerometer 281 is also provided in the housing 271, which is operatively connected to the controller 278. Operation of the device 270 when connected to the container 275 will now be described.

In a principal mode of operation, to determine the level L of liquid inside the container 275, the controller 278 instructs the optical emitters 273 to each emit radiation towards the surface of the liquid inside the container 275 at a given intensity. The optical receiver 274 receives the reflected radiation from each optical emitter 273 via the surface of the liquid and each of these intensities is recorded by the controller.

For each operation of the sensing assembly 272, the controller 278 records the intensities of radiation emitted by each of the optical emitters 273 as intensities IE1; IE2 . . . IEn (where n is the total number of optical emitters), and records the intensities of radiation received by the optical receiver 274 from each of the optical emitters 273 as received intensities IR1; IR2 . . . IRn.

By comparing the emitted radiation intensities IE1; IE2 . . . IEn with the received radiation intensities IR1; IR2 . . . IRn, the controller 278 calculates a series of intensity ratios IE1:IR1; IE2:IR2 . . . IEn:IRn, which are then used to determine the level of the liquid inside the container. At the most basic level, if the intensity ratio of IE1:IR1 is the same as IE2:IR2, given the optical emitters 273 are equidistant from the optical receiver 274, this indicates that the level of the liquid inside the container is parallel to the top of the bottle, as shown in FIG. 27. In contrast, if these two intensity ratios are different, this indicates that the liquid level is at a different angle, such as that shown in FIG. 28.

To accurately determine the level and the quantity of liquid inside the container 275, the controller 278 processes the recorded intensity ratios using a database located in the memory 280. The database contains an individual record for each container which is operable to connect with the device 270. Each record from the database contains a look-up table of information, which contains expected intensity ratios (IE1:IR1 and IE2:IR2) for the container 275 when filled at different orientations, and with different quantities of liquid.

By comparing the information from the look-up table with the recorded intensity ratios, the controller 278 calculates the level and quantity of liquid inside the container 275 and stores this information in the memory 280.

In situations where a container 275 to the device 270 contains no stored record in the database, the sensing assembly 272 can be used in a calibration mode to create a new record. In the calibration mode, the sensing assembly 272 is operated as the container is filled from empty, and as it is positioned at different orientations. At each point during the calibration mode, the controller 278 calculates the recorded intensity ratios (IE1:IR1 and IE2:IR2) and stores them in the record relating to the container 275. For each set of recorded intensity ratios, the user includes information in the record relating to the orientation and fill level of liquid inside of the container 275.

To improve the accuracy of the results obtained by the device 270 during its use, the controller 278 when recording each intensity ratio also records a parameter from the accelerometer 281 relating to the acceleration experienced by the device 270. For each recorded acceleration parameter, the controller 278 determines whether the parameter 278 exceeds a predetermined threshold acceleration parameter stored in the memory 280. The predetermined threshold is indicative of an excessive acceleration, which causes sloshing of liquid inside the container 275 connected to the device 270. In the event of a recorded acceleration parameter exceeding the predetermined threshold acceleration parameter, the controller 278 flags the recorded intensity ratios associated with the recorded acceleration parameter as being unreliable (due to sloshing).

Figure 29:
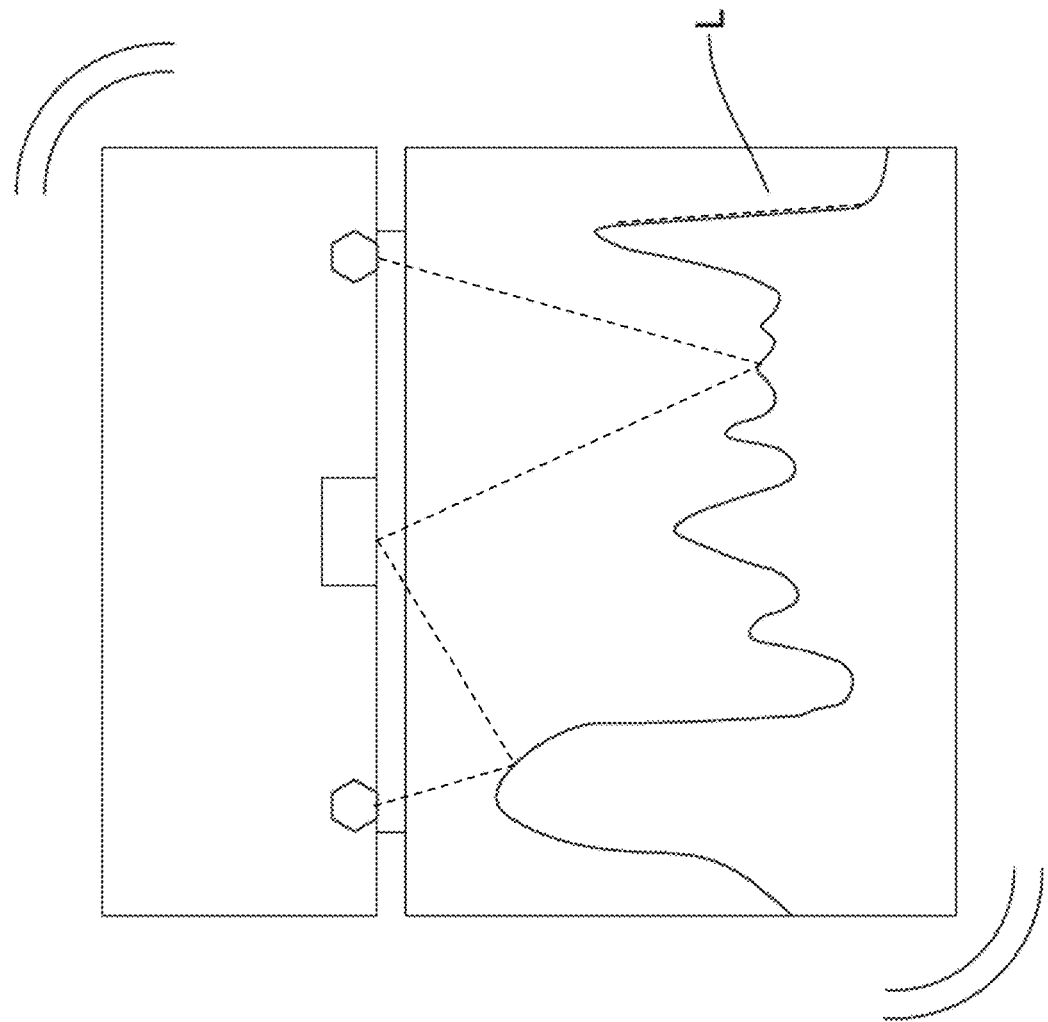
FIG. 29 shows a sectional view of the device and the container from FIG. 27 being used whilst undergoing acceleration.

Even without the use of the accelerometer 281, the controller 278 is nonetheless operable to determine whether a set of recorded intensity ratios occur during a period of excess acceleration. In this regard, for each set of intensity ratios recorded at a given time, the controller 278 checks whether any of these intensity ratios is of a predetermined order of magnitude different than the remaining recorded intensity ratios from the set. In the event that the controller 278 determines that this is the case, this indicates that the liquid inside the container has 'sloshed' as a result of the excess acceleration, as shown in FIG. 29. In this event, the controller 278 flags the set of recorded intensity ratios as being unreliable.

It will be appreciated that instead of recording the relative intensities of radiation emitted by the optical emitters 273 with the radiation received by the optical emitter 274, the controller 278 could instead record the time taken for radiation emitted by each of the optical emitters 273 to be received by the optical receiver 274. In this arrangement, the look up table would instead contain time periods as opposed to intensity ratios.

Figure 30:
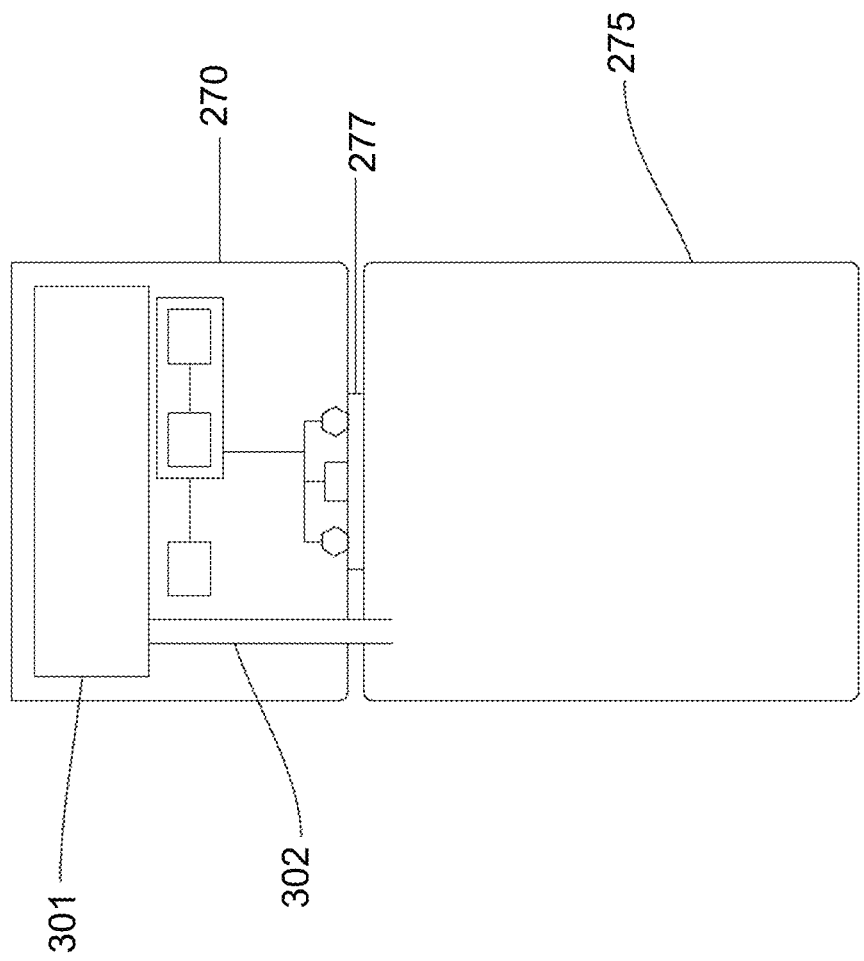
FIG. 30 shows a sectional view of the device from FIG. 27 being used as part of a breast pump assembly.

In terms of the applications for the device 270, it will be appreciated that the device can be used in a wide variety of applications. One possible application is the use of the device 270 to determine the level of liquid located within a container 275, such as a baby bottle, used as part of a breast pump assembly. In this arrangement, the device 270 is associated with a breast pump 301 which assists with the expression of milk from a breast. The breast pump may be located in the housing 271 of the device 270 as shown in FIG. 30, or it may be realisably connected to the housing 271.

Either way, the device 270 would be connectable to the container 275 such that milk expressed by the breast pump can pass from the pump via a channel 302 into the container 275.

The breast pump may be any type of breast pump system including any shapes of milk container or bottle and may comprise a pump module for pumping milk from a breast. The pump module being contained within the housing may comprise: a coupling, a container attachable to the housing via the coupling to receive milk from the pump, a sensing assembly within the housing and comprising at least one optical emitter operable to emit optical radiation towards the surface of the body of milk held in the container when the housing is connected to the container, an optical receiver for receiving the reflected radiation from the surface of the milk, and a controller electrically connected to the sensing assembly for receiving signals from the optical receiver and calculating the level of the milk inside the container based on the reflected radiation received by the optical receiver.

By determining the level of milk inside the container based on reflected radiation from the surface of the milk in the container, there is no need to monitor the individual droplets of milk entering the container, such that the sensing assembly can avoid errors associated with measuring these droplets. For example, because we take multiple reflection-based measurements once the container is filled, we can generate an average measurement that that is more accurate than a single measurement. But with systems that rely in counting individual droplets, that is not possible—further, systemic errors (e.g. not counting droplets below a certain size) will accumulate over time and render the overall results unreliable. Furthermore, by not needing to measure these droplets, the sensing assembly from the breast pump need not always be on during the pumping process, which saves power.

When at least two optical emitters are used, the sensing assembly from the breast pump may determine the level of milk inside the container more accurately and irrespective of the orientation of the liquid level inside the container.

Each optical emitter may be equidistant from the optical receiver in order for the controller to easily calculate the level of the milk inside the container based on the reflected radiation originating from each optical emitter. The signals from the optical receiver preferably comprise information relating to the intensity of the radiation received by the optical receiver.

Each optical emitter may be operable to emit radiation at a different wavelength, or at a different time, than the other optical emitters. In this way, the controller can more easily process the signals from the optical receiver, and more easily distinguish between the radiation emitted by each of the optical emitters.

The optical emitter may emit radiation in the visible range of wavelengths. Alternatively, it may be UV or IR light. The emitted wavelength may be for example between 10 nm and 1 mm.

The sensing assembly may also comprise at least one accelerometer electrically connected to the controller. The controller may be configured to record an accelerometer parameter from the accelerometer and determine whether the accelerometer parameter exceeds a predetermined threshold. The predetermined threshold may be indicative of an excessive acceleration, which might cause sloshing of milk inside any container connected to the breast pump.

Figure 31:
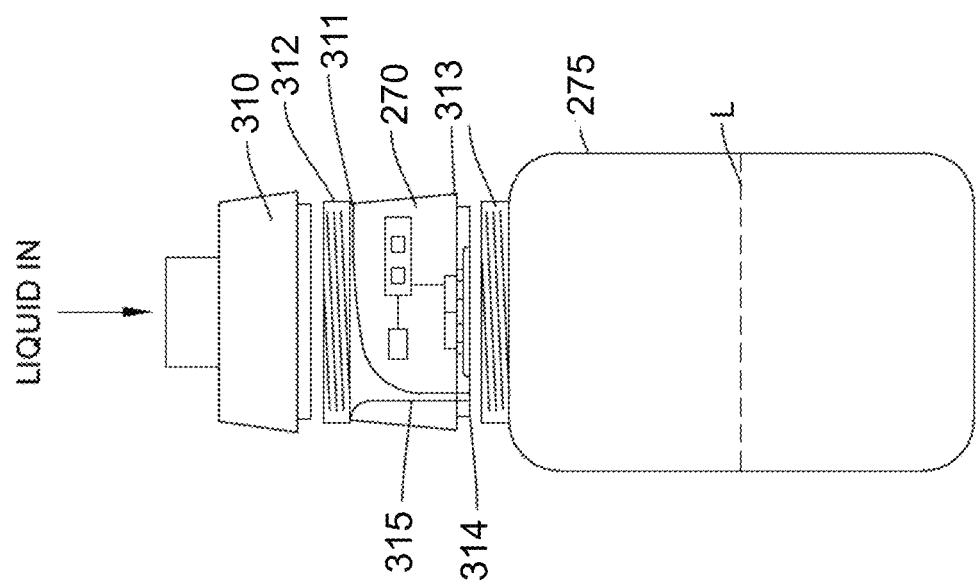
FIG. 31 shows a sectional view of a device connected between a container and its lid, and which is operable to determine the level of liquid inside the container.

Another application for the device 270 is as a collar for detecting the level/quantity of liquid in a container 275, such as a baby bottle, via its lid 310. An example of the device 270 being used as such a collar is shown in FIG. 31. In this arrangement, the device 270 is located between the container 275 and the lid 310, and comprises a first end 311 having a first coupling 312 for attaching the collar to the lid 310. The device comprises a second end 313 having a second coupling 314 for attaching the device 270 to the container 275. The second coupling may be a screw thread, shown in FIG. 31, on the inside surface of the container 275. In this way, the distinctive bottom inside surface can be used by the sensing assembly 272 to more easily calibrate itself to the container 275 on which the distinctive bottom inside surface is located. The distinctive bottom may also be used to help identify which container 275 the device is connected to, and thus which record should be used from the database when the device 270 is used.

To further improve the accuracy of the sensing assembly 272, the controller 278 may also be configured to use the recorded information from the accelerometer 281, in situations where the record acceleration is below the predetermined threshold acceleration parameter, to calculate a more accurate liquid level and/or quantity of liquid located inside the container which is compensated for acceleration.

In one particular arrangement, the controller 278 may poll the accelerometer 281 prior to each operation of the sensing assembly 272 to verify that the device 270 is not currently undergoing excessive acceleration. In the event of the controller 278 determining excessive acceleration in the device 270, the controller 278 would continually re-poll the accelerometer, and not operate the sensing assembly 272, until the parameter from the accelerometer is determined as being below the predetermined threshold acceleration parameter stored in the memory 280.

It will also be appreciated that for each container record stored in the database, the container record may comprise a plurality of look up tables, wherein each look up table is associated with a particular liquid used in the container, and wherein each look up table contains its own set of intensity ratios. In this way, the device 270 can more accurately determine the level/quantity of different liquids used in a particular container 275.

As described herein, the sensing assembly 272 has been described as having a plurality of optical emitters 273. It will be appreciated however that the sensing assembly could operate using a single optical emitter 273 and plurality of optical receivers 274. In this arrangement, each record from the database would contain a plurality of ratios relating to the emitted radiation from the optical emitter 273 as received by each of the optical receivers 274. In use of the device 270, the controller 278 would then similarly record the emitted radiation from the optical emitter 273 as received by each of the optical receivers 274. In an alternate arrangement, there may be provided a plurality of optical emitters 273 and a plurality of optical receivers 274, wherein each optical emitter 273 is associated with a respective optical receiver 274. In its simplest arrangement, the sensing assembly 272 may comprise a single optical emitter 273 and a single optical receiver 274.

In certain configurations, the optical emitters 273 may together emit radiation having the same wavelength. In other configurations, the optical emitters 273 may each emit radiation having a different wavelength. In this latter configuration, the optical receiver 274 would then be able to determine which optical emitter 273 is associated with any given received radiation, based on the wavelength of the received radiation.

The optical emitters 273 may also each emit radiation at different times, such to allow the controller 278 to more easily process the signals from the optical receiver 274, and more easily distinguish between the radiation emitted by each of the optical emitters 273.

In relation to the electrical connection between the controller 278 and the sensing assembly 272, it will be appreciated this electrical connection may be either a wired/wireless connection as required.

Although not shown in the Figures, the device 270 herein described is preferably powered by a battery or some other power source located in the device 270. In other embodiments, the device 270 may be powered using mains electricity.

In one configuration, it is also envisaged that rather than the controller 278 comparing the information from the look-up table with the recorded intensity ratios to calculate the level and quantity of liquid inside the container 275, the controller 278 could instead process the recorded intensity ratios through a liquid-level equation stored in the memory 280. In this configuration, the liquid-level equation could be a generalised equation covering a family of different containers, or could be an equation specific to a container having a given shape and/or type of liquid inside.

It will also be appreciated that in some applications of the device 270, the device could be used to detect the level of a solid, as opposed to a liquid, in a container. As used herein, the terms 'optical emitter' and 'optical receiver' are intended to cover sensors which can emit radiation in or close to the optical wavelength. Any type of radiation at or close to the optical wavelength is suitable provided that it does not have any harmful effects. The exact wavelength is not important in the context of the invention. Such sensors thus include those which can emit visible radiation (such as radiation having wavelengths in the region of 400 nm-700 nm), and/or those which can emit IR radiation (such as radiation having wavelengths in the region of 700 nm-1 mm and/or those which can emit UV radiation (such as radiation having wavelengths in the region of 10 nm to 400 nm).

Existing prior art for such a sensor module is the apparatus disclosed in RU2441367. In this apparatus, the container is an industrially sized milk tank, which only includes a single laser mounted at the top of the tank. Whilst this apparatus is suited for large-sized containers, which do not move in use, the apparatus is less-suited for applications where the container moves in use, or where the liquid level inside the container is non perpendicular to the laser beam shone into the container. In contrast, the sensor module described above can be used in a variety of different applications, is conveniently located within a housing, and which by virtue of it having at least two optical emitters, can determine the level of liquid even inside containers of irregular shapes, and which can determine the level of liquid inside a container irrespective of the orientation of the liquid level inside the container.

Further to the embodiments of the fluid measurement system in different contexts, it can be appreciated that different functions entirely may be possible using the same component structure. For example, it is known that certain molecules within breast milk absorb specific wavelengths of light at characteristic propensities. Whilst the proposed system uses multiplexed IREDs at the same wavelengths to perform proximity measurements, the same array of IREDs may instead be used to emit several different wavelengths of light and determine their absorption upon reflection. If appropriately calibrated, the system may be able to report on the presence or concentration of specific compounds in the expressed milk, such as fat, lactose or protein content.

In addition to this embodiment, it is feasible that the system might be applied to monitor the change in volume of any other container of liquid, given there is sufficient reflection of IR off its surface. These embodiments might include for example: liquid vessel measurement such as for protein shakes, cement or paint, or volume measurements within a sealed beer keg.

Section C: Bra Clip

This section describes a bra clip that forms an accessory to the Elvie™ pump.

It relates to a system allowing a user to quickly and simply adjust the cup size of a maternity bra to allow discrete and comfortable insertion and use of an integrated wearable breast pump. As such, the user does not need a specialised adjustable bra; instead the present system works with all conventional maternity bras. The user also does not have to purchase any larger bras to wear while pumping.

Figure 32:
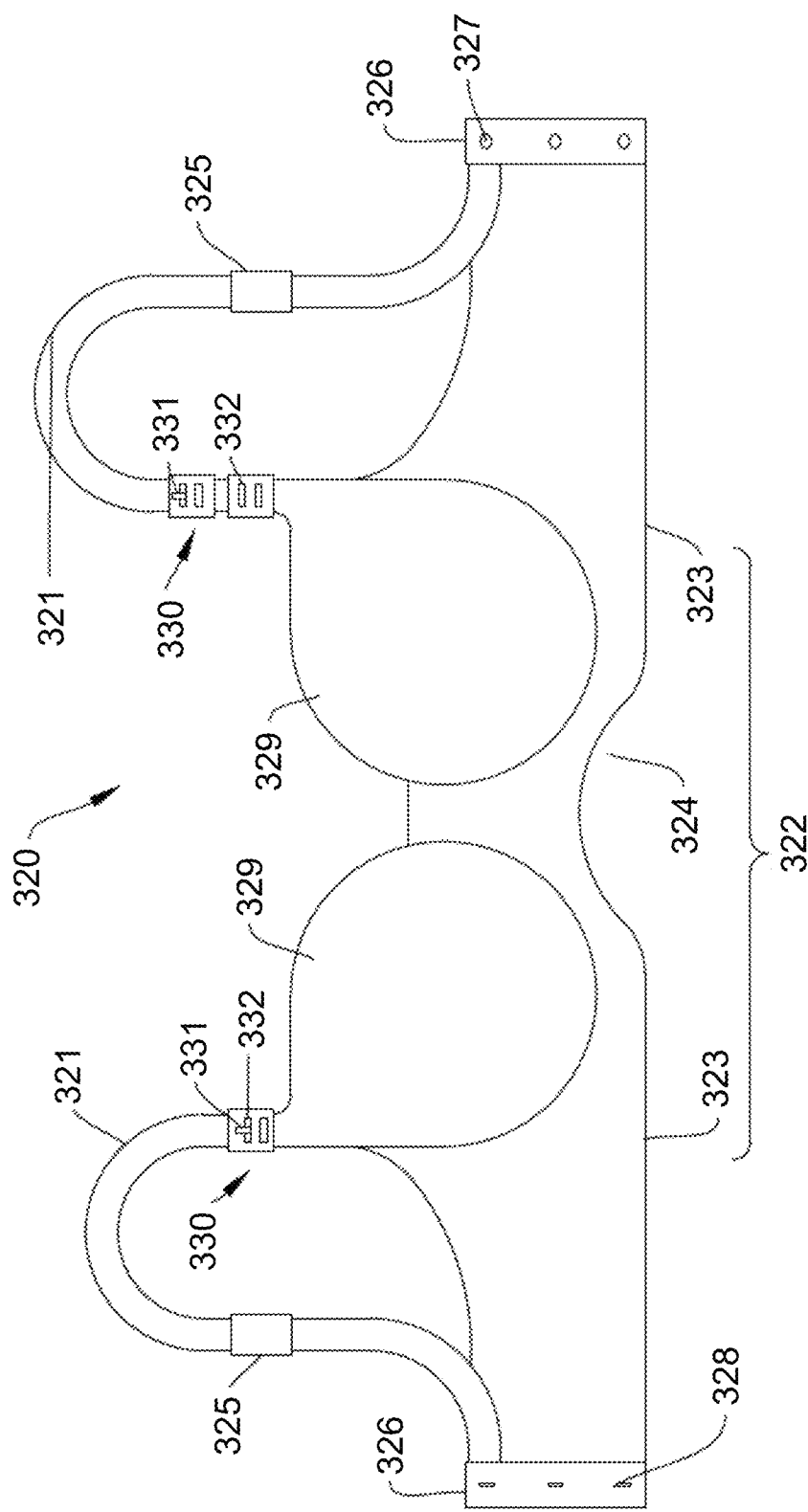
FIG. 32 depicts a prior art design for a maternity bra.

As shown in FIG. 32, a typical maternity bra 320 comprises a support structure made up of shoulder straps 321 which support the bra 320 on the wearer's shoulders, and a bra band 322 for extending around a user's ribcage, comprising two wings 323 and a central panel or bridge 324. The straps 321 are typically provided with adjustment mechanisms 325 for varying the length of the straps 321 to fit the bra 320 to the wearer. At the outermost end of each wing, an attachment region 326 is provided. Typically, hooks 327 and loops 328 are provided for securing the bra 320 at the user's back. However, any other suitable attachment mechanism may be used. Alternatively, the attachment region 326 may be provided at the front of the bra 320 in the bridge region 324, with a continuous wing 323 extending continuously around the wearer's back. Typically, a number of sets of loops 328 are provided to allow for variation in the tightness of the bra 320 on the wearer. While shown as having a separation in FIG. 32, the wings 323 and bridge 324 may form a single continuous piece in certain designs. Likewise, while shown with a distinct separation in FIG. 32, the shoulder straps 321 and the wings 323 may likewise form a single continuous piece.

The maternity bra 320 is further provided with two breast-supporting cups 329 attached to the support structure. The cups 329 define a cup size, which defines the difference in protrusion of the cups 329 from the band 322. The European standard EN 13402 for Cup Sizing defines cup sizes based upon the bust girth and the underbust girth of the wearer and ranges from AA to Z, with each letter increment denoting a 2 cm difference between the protrusion of the cups 329 from the band 322. Some manufacturers do vary from these conventions in denomination, and some maternity bras are measured in sizes of S, M, L, XL, etc.

The cups 329 may be stitched to the bra band 321. At least one of the cups 329, is in detachable attachment with the corresponding strap 321. In particular, this is achieved at attachment point 330 where a hook 331 attached to the bra strap 321 engages with a clasp 331 attached to the cup 329. The hook 331 and the bra strap adjuster 325 are set such that in the closed position, the cup size of the bra 320 fits the wearer's breasts.

In FIG. 32, the left cup 329 is shown attached to its attachment point 330, which the right cup 329 is unattached. In this manner, the wearer is able to detach the cup 329 to expose their breast for feeding or for breast pumping. Once this is completed, the cup 329 is reattached and the maternity bra 320 continues to function as a normal bra.

While in the depicted embodiments, a hook 331 is shown on the bra strap 321 and a clasp 332 is shown on the cup 329, it is appreciated that the provision of these may be reversed, or that alternative attachment mechanisms may be used.

A maternity bra therefore may comprise a support structure comprising shoulder straps and a bra band and a first and a second cup each attached to the support structure to provide a first cup size, at least one cup being at least partially detachable from the support structure at an attachment point.

In other embodiments, the detachable attachment point 330 may be provided at a different location, such as at the attachment between the bra band 322 and the cup 329. The mechanism for such an attachment point is the same as described above.

A clip has been designed such that it is configured to be attached to the support structure at a position away from the attachment point. This results in the original attachment point being usable, with the clip providing an alternative attachment point to give, in effect, an adjusted cup size.

Alternatively, the clip may also be attachable to the support structure at a plurality of non-discrete positions. This ensures essentially infinite adjustment of the clip position such that the perfect position for the user can be found.

The clip can also extend between an unextended and an extended state, and can attach to the support structure at the attachment point; the first cup size is providable when the at least partially detachable cup is attached to the clip when the clip is an unextended state; the second cup size is providable when the at least partially detachable cup is attached to the clip when the clip is in an extended state. An extendable clip like this allows quick switching between the two states in use.

Figure 33:
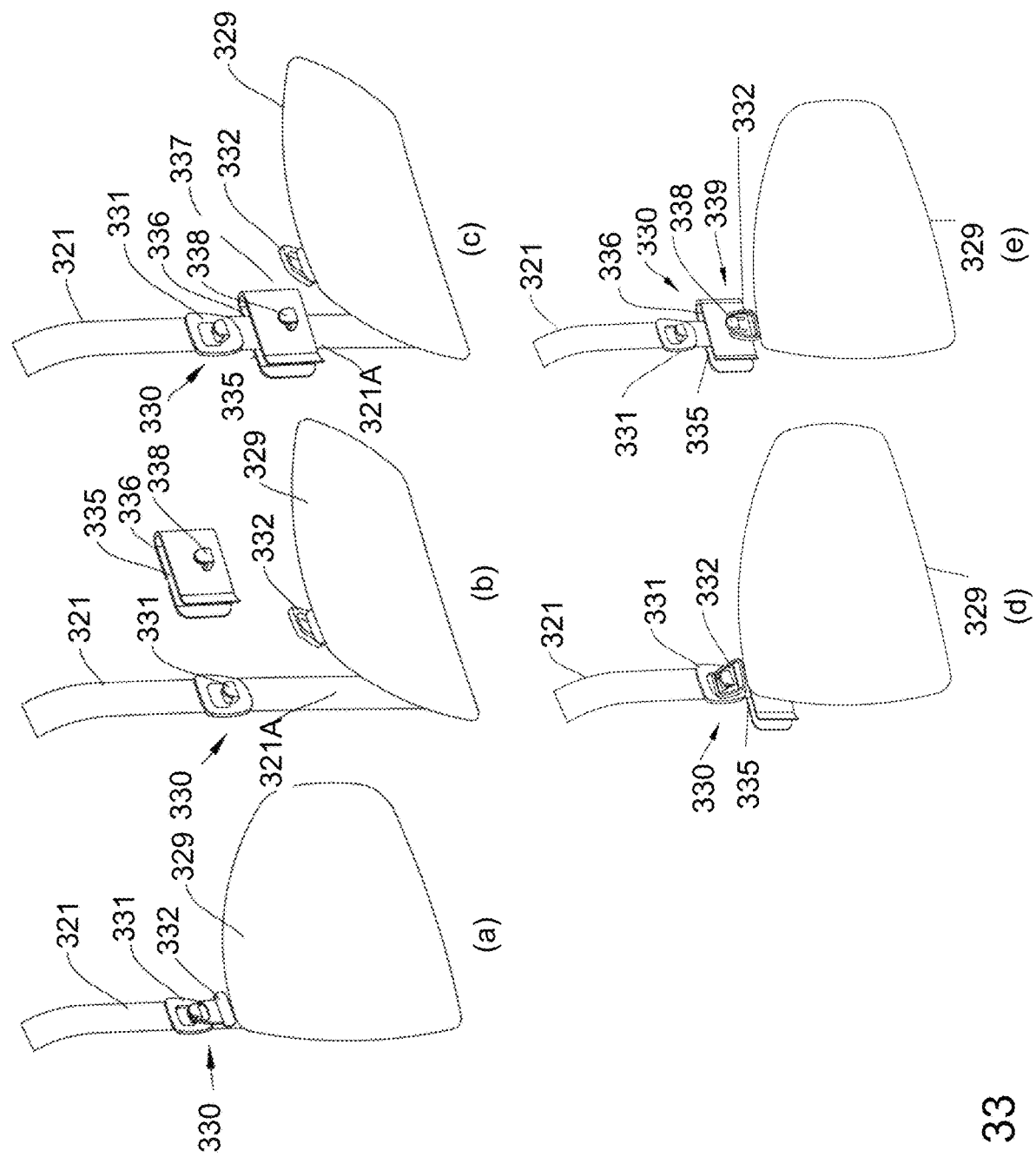
FIG. 33 depicts a clip and clasp being fitted to a maternity bra.

FIG. 33 depict a clip 335 according to the present invention, along with a clasp 332 shown in isolation from the bra cup 329 it is normally attached to. The clip comprises a first engagement mechanism and at least one second engagement mechanism(s). The clip is attachable in a releasable manner to the support structure at a first position via the first engagement mechanism and attachable in a releasable manner to one of the partially detachable cups via the second engagement mechanism to provide a second cup size different to the first cup size. The clip 335 is provided with a material pathway 336 which receives a portion of the bra strap 321. In the particular embodiment of these Figures, the clip 335 is substantially U-shaped, with a narrowing profile towards its open end. However, it is appreciated that any other suitable shape with a material pathway may be used, such as an S-shape or E-shape. The clip 335 is designed to be attached to the bra strap 321 in a releasable manner, with the slot 336 acting as a support engaging mechanism. The releasable manner means that the clip 335 may be simply removed from the bra 320 without causing any damage to the functioning of the bra 320. To enhance the ease of attachment, the clip 335 may be provided with outwardly extending wings 204 which help direct the bra strap 321 into the clip 335. The clip 335 is further provided with a hook 220 acting as a cup engaging mechanism which can engage with the clasp 332.

FIG. 33 (c) shows the clip 335 being attached to a bra strap 321 in order to provide a second attachment point 337 for the clasp 332 to attach to, and hence to provide a second cup size for the bra 320. In this particular embodiment, the clip 335 is attached in a portion of strap 321A below the original attachment point 330 and hence the second attachment point 337 is likewise below the original attachment point. This results in a second cup size larger than the first cup size. In preferred embodiments, as shown in these Figures, the clip 335 engages with the support structure in a direction transverse to the direction in which it engages with the cup.

FIGS. 33 (d) and (e) show how a wearer is able to move between the first and second cup sizes. In 33(d), the cup 329 is attached at the first attachment point 330 to provide a first cup size. The wearer then disengages the clasp 332 from the hook 331 at the hook 338 at the second engagement point 239. In this manner, the wearer is easily able to transition between the two cup sizes.

Figure 34:
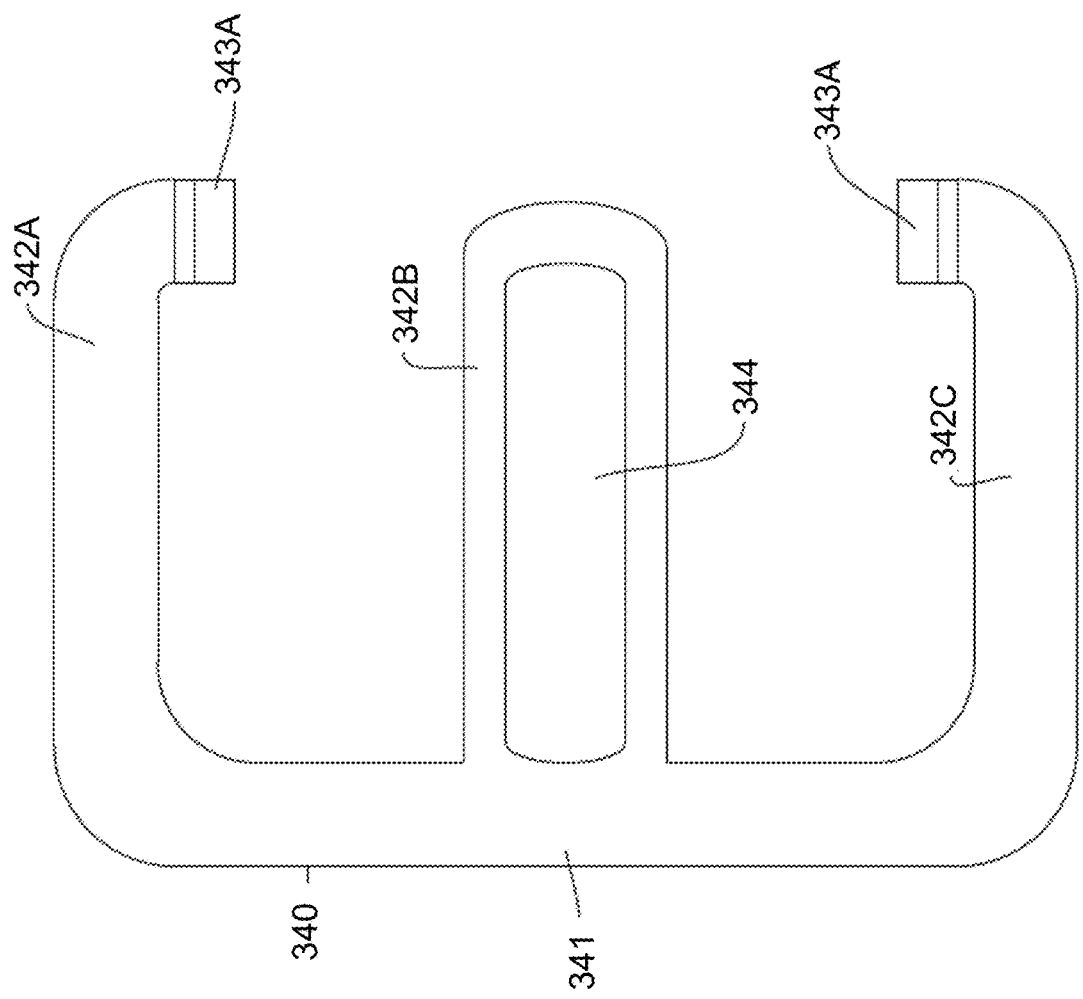
FIG. 34 depicts an alternative clip for adjustment of a maternity bra.
Figure 35:
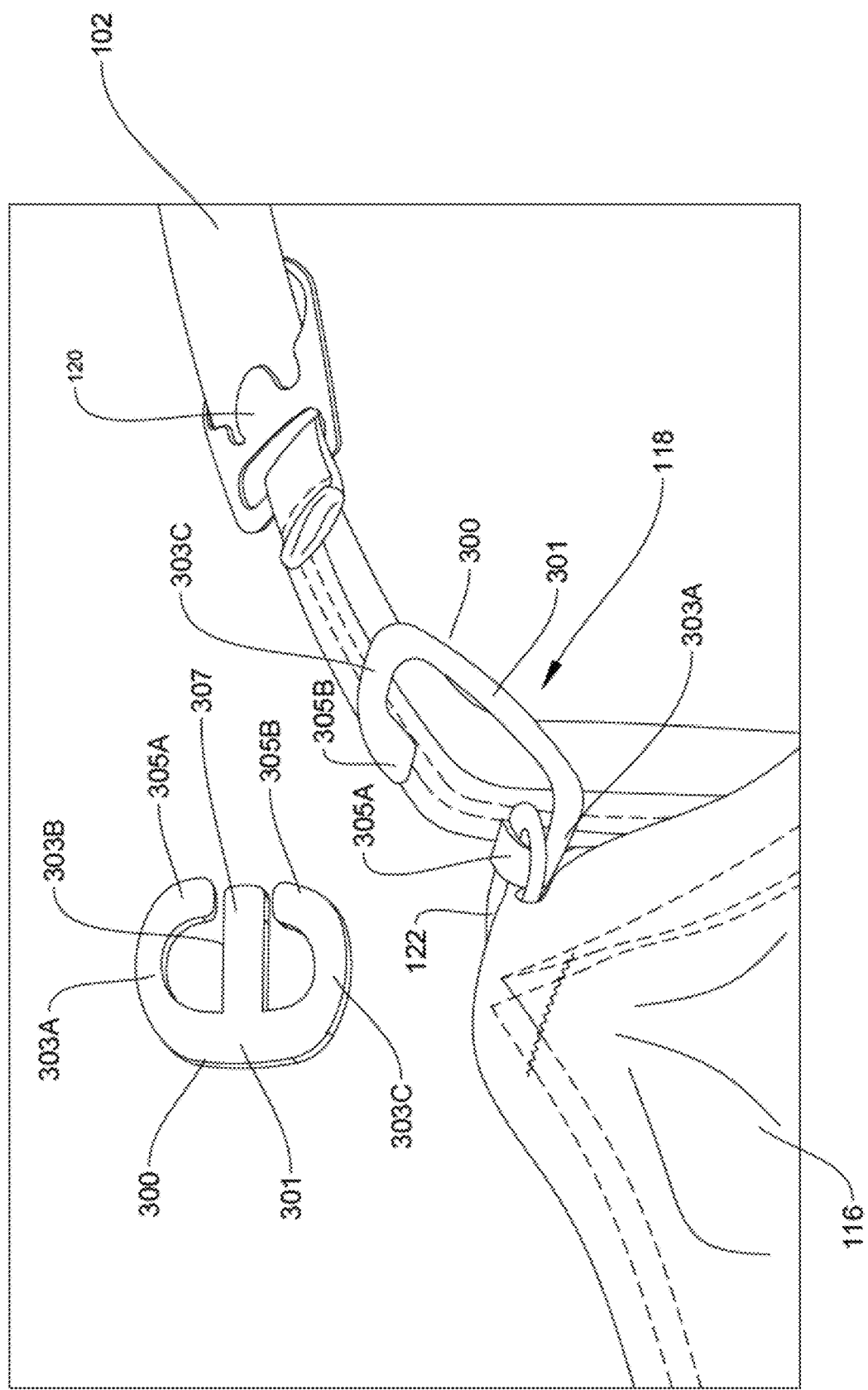
FIG. 35 depicts the alternative clip of FIG. 34.

FIGS. 34 and 35 show an alternative design for a clip 340. This clip 340 is substantially "E-shaped", with a back portion 341 and first, second and 5 third prongs 342A, 342B, 342C extending transverse from this back portion 341. The three prongs 342A, 342B, 342C are spaced apart along the length of the back portion 341. The first and third prongs 342A, 342C are provided with attachment clips 343A, 343B.

These attachment clips 343A, 343B can engage with the clasp 332 of a bra to provide the second cup size. Depending upon the orientation of the clip 300, one or the other of the attachment clips 343A, 343B will be used to attach the clasp 332 of the bra. By providing these clips 343A, 343B on both of the first and the third prongs 342A, 342C the clip is easily reversible so it can be used on either side of the bra. Preferably the clip 340 is also symmetrical, to aid the reversibility of the clip 340.

FIG. 35 shows the clip 340 attached to a bra. As can be seen, the first and third prongs 342A, 342C extend on the front side of the bra strap, with the second prong 342B extending on the rear side of the bra strap. In this manner, the clip 340 is attached to the strap. In preferable embodiments, a grip-enhancing member 344 such as a number of projections and/or roughened patches can be provided on the second prong 342B in order to strengthen this grip.

In alternative embodiments, the attachment clip could be provided on the second, centremost prong 342B. In such an arrangement, the centremost prong 342B would be on the outside of the bra, with the first and third prongs 342A, 342C on the inside.

The provision of the attachable clip allows maternity bras already owned by the wearer to be quickly transformed into bras with quick switchable double cup size options.

This allows the use of integrated wearable breast pumps which increase the user's required cup size. This allows more design freedom for the breast pump in terms of size and shape, while still allowing the user to discretely pump with the pump held within their bra. By allowing conversion of the user's existing maternity bras, they are not forced to purchase specially designed bras to wear with the pump. The bra is hence normally at the first engagement point 330 when the breast pump device is not being used. As shown in FIG. 33, the clasp 332 is then engaged by the user to discretely switch between the two configurations, and the user then inserts the pump without any complex adjustment or removal of clothing.

Preferably, the clip will be relatively unobtrusive in size and shape and hence can be left in place when the bra is first put on and used when necessary. To this end, the clip is preferably machine washable without significant damage or degradation.

In some embodiments, the clip may be switchable between positions for engaging with each cup so that a single clip may be used on either side of the bra. To achieve this, the clip is preferably reversible. This may provide the user with a visual indication of which breast has produced milk most recently so switching can take place.

In a preferred embodiment, the first engagement mechanism engages with the support structure in a first direction and the second engagement mechanism engages with the cup in a second direction transverse to the first direction. This increases ease of attachment as with this structure the sideways engagement of the clip to the support structure ensures that the second attachment mechanism is correctly orientated for the cup.

The second engagement mechanism may be one or more of a hook or a snap or a clip. This ensures easy interfacing with the traditional hook and clasp systems already provided on maternity bras.

Preferably the clip further comprises two distinct second engagement mechanisms which can be used interchangeably dependent upon the orientation of the clip. This makes the clip easier to use as it can be quickly switched between each bra strap, and the user does not have to worry which way up to put the clip on.

Preferably, the clip comprises a material pathway with an opening for receiving a portion of the support structure as the first engagement mechanism for securing the clip to the bra. This ensures a quick and simple method for attaching the clip to the bra. In particular, the clip may substantially U-shaped, and the material pathway is between the arms of the U.

Preferably, the clip comprises three prongs extending from a central support, the three prongs arranged as a central prong and two outer prongs so as to receive the support structure on one side of the central prong and on the opposite side of each respective outer prong, at least one prong being provided with the second engagement mechanism. This ensures a strong attachment to the bra and a simple design.

Preferably, both outer prongs are each provided with a respective second engagement mechanism. This ensures that the clip is reversible for easier attachment to the bra.

A method of adjusting the cup size of a maternity bra is provided according to the present invention, comprising: providing a maternity bra comprising a support structure comprising shoulder straps and a bra band; and a first and second cup each attached to the support structure to provide a first cup size, the at least one cup being detachable from the support structure at an attachment point, providing a clip comprising first and section engagement mechanisms, attaching the first engagement mechanism of the clip in a releasable manner to a first position of the support structure of the maternity bra, attaching one of the detachable cup to the second engagement mechanism of the clip in a releasable manner to provide a second cup size different to the first cup size.

This clip and method allow a user to quickly and simply adjust the cup size of a maternity bra to allow discrete and comfortable insertion and use of an integrated wearable breast pump.

Preferably, the method further comprises the step of inserting a breast pump into the detachable cup. The adjustment of the size of the bra allows the bra to support the breast pump against the user's breast for comfort and ease.

Preferably, the method further comprises the steps of: detaching the first engagement mechanism of the clip from the first position support structure of the maternity bra; attaching the first engagement mechanism of the clip in a releasable manner to a second position of the support structure of the maternity bra; and attaching the other of the detachable cups to the second engagement mechanism of the clip in a releasable manner to provide a second cup size different to the first cup size. This allows the user to use a single clip on either of the cups.

Figure 36:
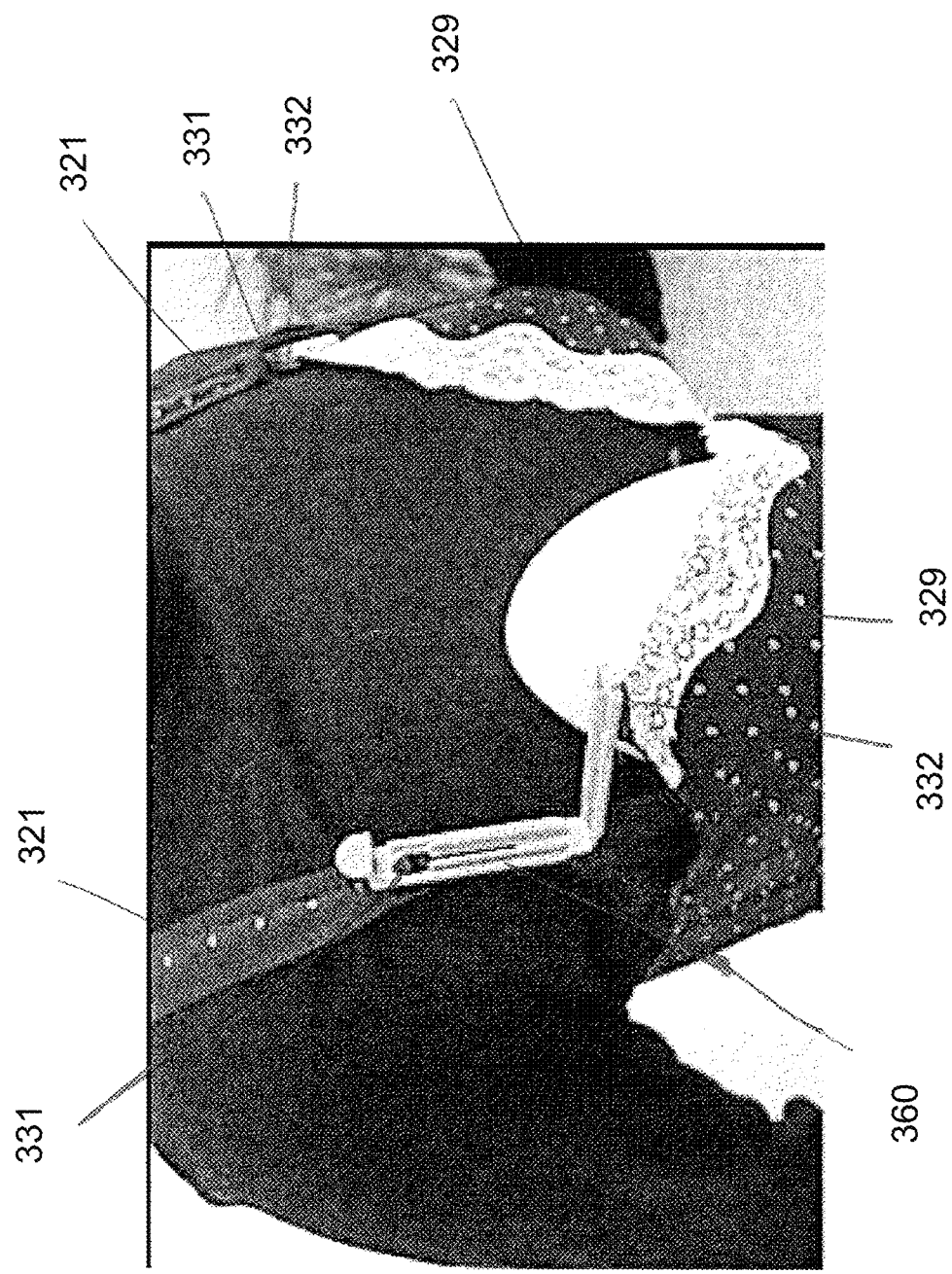
FIG. 36 depicts an alternative clip for adjustment of a maternity bra.

An alternative embodiment may be provided, with an extendable clip 360 as shown in FIG. 36. In such an embodiment the clip is attached to the hook 331 on the strap 321 in a releasable manner, with the clasp 332 attached to an expandable portion of the clip. The clip is then able to expand between an unexpanded state where the clasp 332 is held in substantially the same position as the first attachment point 330 to provide the first cup size, and an expanded state, where the clasp 332 is held in a second position away from the first attachment point 330 to provide the second cup size.

For example, an elongate clip with first and second opposite ends may be provided. A first attachment point for attaching to the hook 331 is provided at the first end, and a second attachment point for attaching to the clasp 332 is provided at the second end. The elongate clip is hinged between the two ends, such that the clip can be folded between an elongate configuration to a closed configuration where the second end touches the first end. A clasp can be provided on the clip to hold the second end in this closed configuration. Thus, in the closed position the clasp 332 is held in substantially the same location as the first attachment point 330 to provide the first cup size, and in the open position the clasp is held away from the first attachment point 330 to provide the second cup size.

Other extendable clip embodiments are also possible, for example sliding clips or elastic clips.

Figure 37:
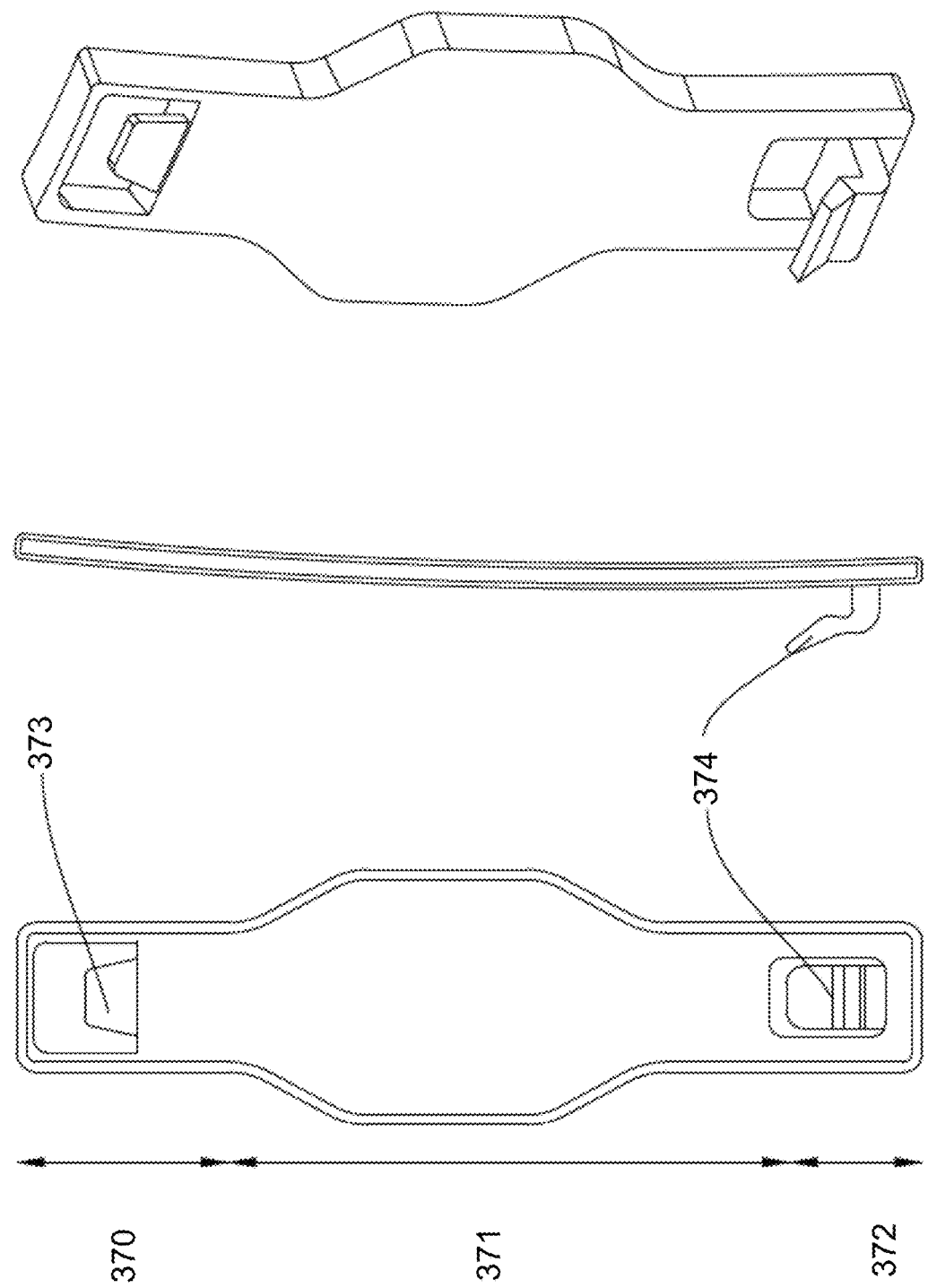
FIG. 37 depicts an alternative clip for adjustment of a maternity bra.
Figure 38:
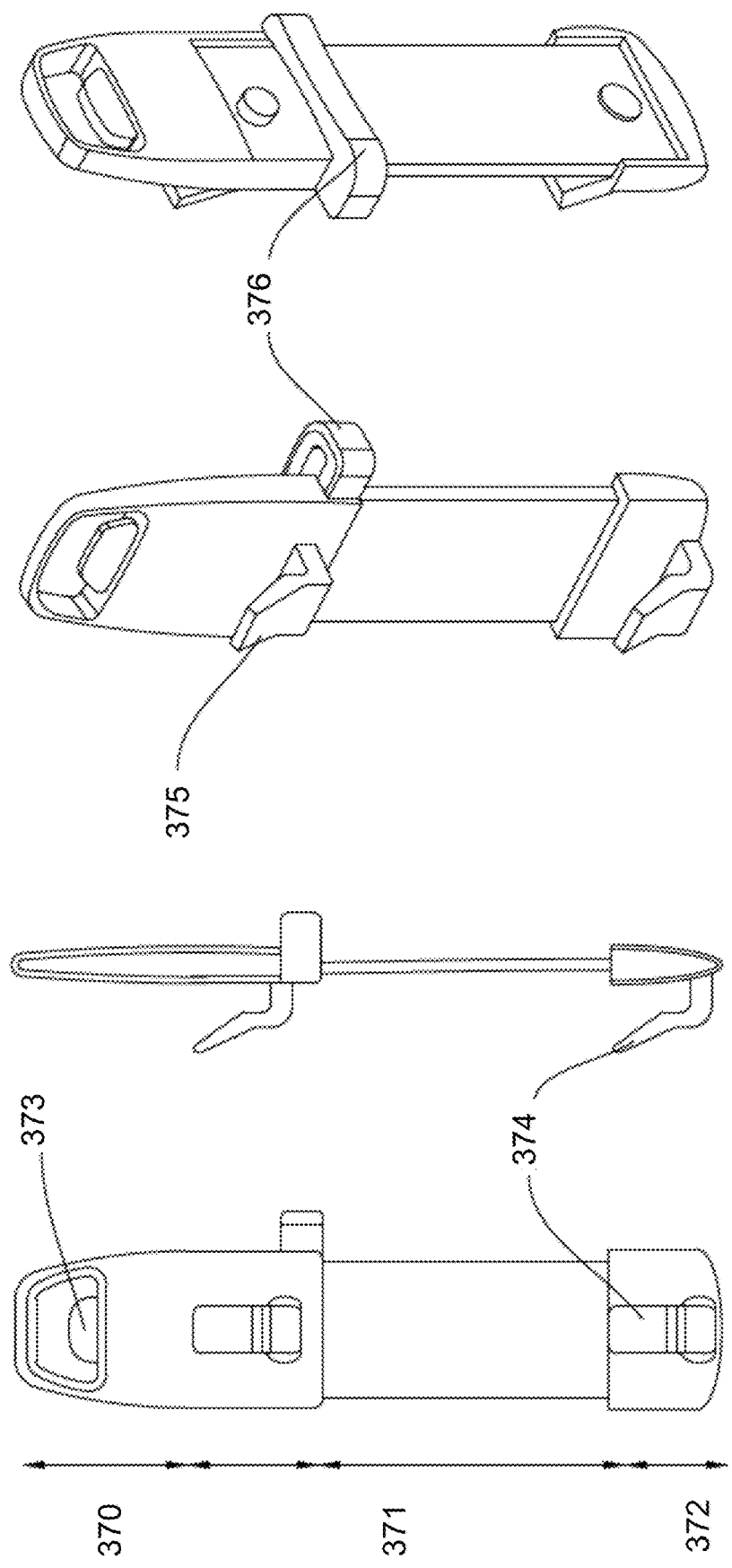
FIG. 38 depicts an alternative clip for adjustment of a maternity bra.

Additional embodiments of a maternity bra adjuster are provided in FIGS. 37 and 38. The alternative proposed solution is a small adapter device, which comprises a first portion 370 including a clasp 373 and a second portion 372 including a hook 374, in which the first and second portions are separated by a small distance 371 in order to provide two different adjustable sizes. The first portion includes a clasp 373 that is designed to attach to the hook on the bra strap 321. It may also include a top hook 375 positioned underneath the clasp, and a clip 376 on the rear side. The second portion includes a bottom hook 372.

Figure 39:
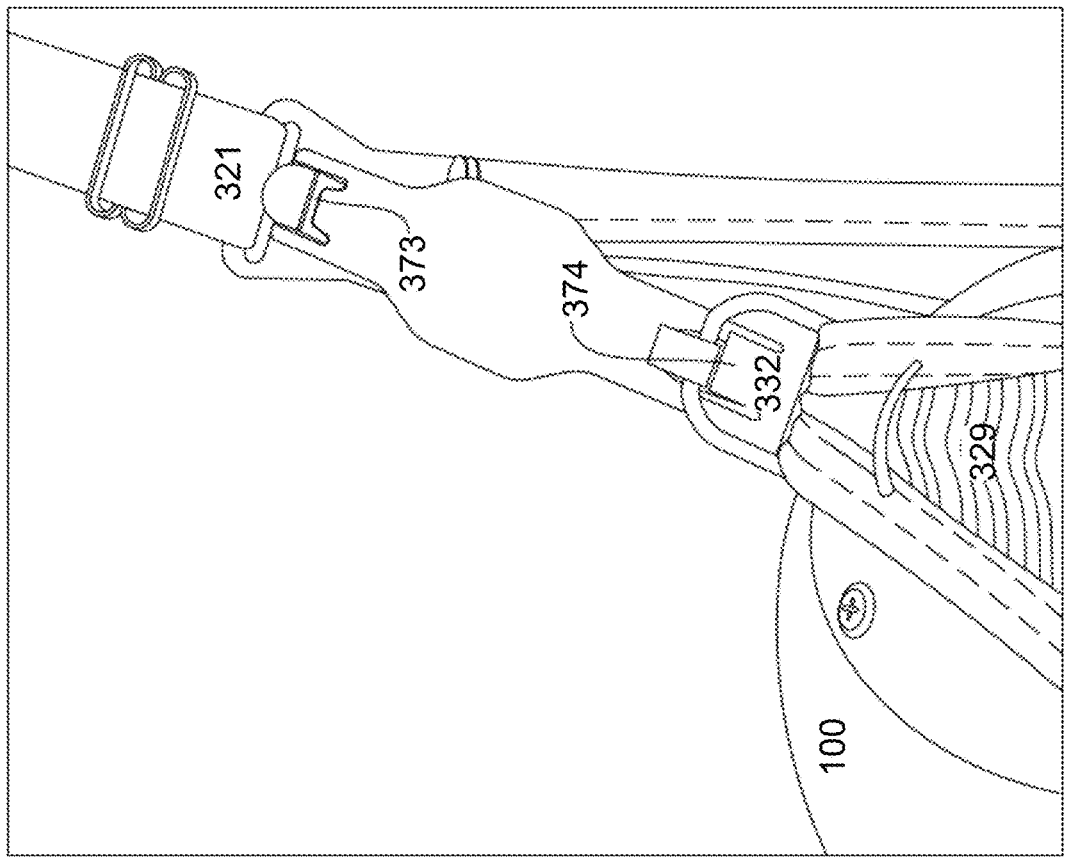
FIG. 39 depicts adjustment of the maternity bra of FIG. 37.

The clasp 332 that is present on the cup 329 of the maternity bra, may then either engage with the top hook (321) to provide a first cup size, and engage with the bottom hook (332) to provide a second cup size that is different from the first cup size, as illustrated in FIG. 39. The user may then discretely switch between a non pumping position, provided by the first cup size, and a second pumping position without any complex adjustment or removal of clothing needed, while using a wearable breast pump system (100).

The first portion and second portion may be made of plastic and may be separated by a stretchy material such as elastic or elastomeric material. The first portion may also include a clip on the rear side, the purpose of which is to allow the user to leave the clip attached to the bra for an extended time period.

Section D: Use of Piezo Pump in Wearables

As described in Section A, the breast pump system includes a piezo air pump, resulting in a fully wearable system that delivers a quiet, comfortable and discreet operation in normal use. This section gives further information on the piezo air pump.

In comparison with other pumps of comparable strength, piezo pumps are smaller, lighter and quieter.

Each individual Piezo pump weighs approximately 6 gm and may, with material and design improvements, weigh less than 6 gm.

In operation, the Elvie breast pump system makes less then 30 dB noise at maximum power and less than 25 dB at normal power, against a 20 dB ambient noise; tests indicate that it makes approximately 24 dB noise at maximum power and 22 dB at normal power, against a 20 dB ambient noise.

Piezo pumps also have lower current draw, allowing for increased battery life. A piezo pump is therefore ideally suited for wearable devices with its low noise, high strength and compact size. Further, as shown in the breast pump system of FIGS. 7 and 8, more than one piezo pump may be used.

Whilst a breast pump system is largely described in previous sections, the use of piezo mounted either in series or in parallel can also be implemented in any medical wearable devices or any wearable device. The piezo pump may pump air as well as any liquid.

Figure 40:
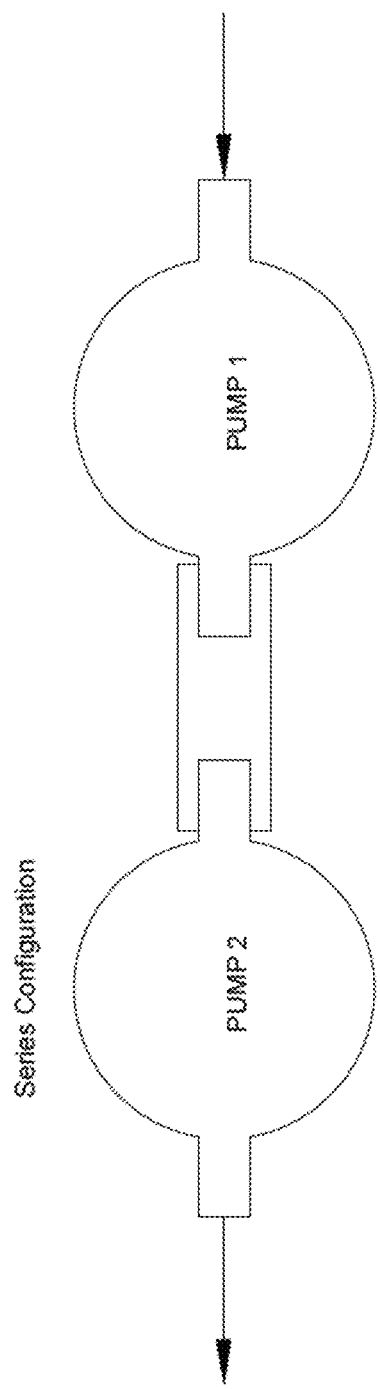
FIG. 40 shows a configuration with two piezo pumps mounted in series.

With reference to FIG. 40, a diagram illustrating a configuration of two piezo pumps mounted in series is shown.

Figure 41:
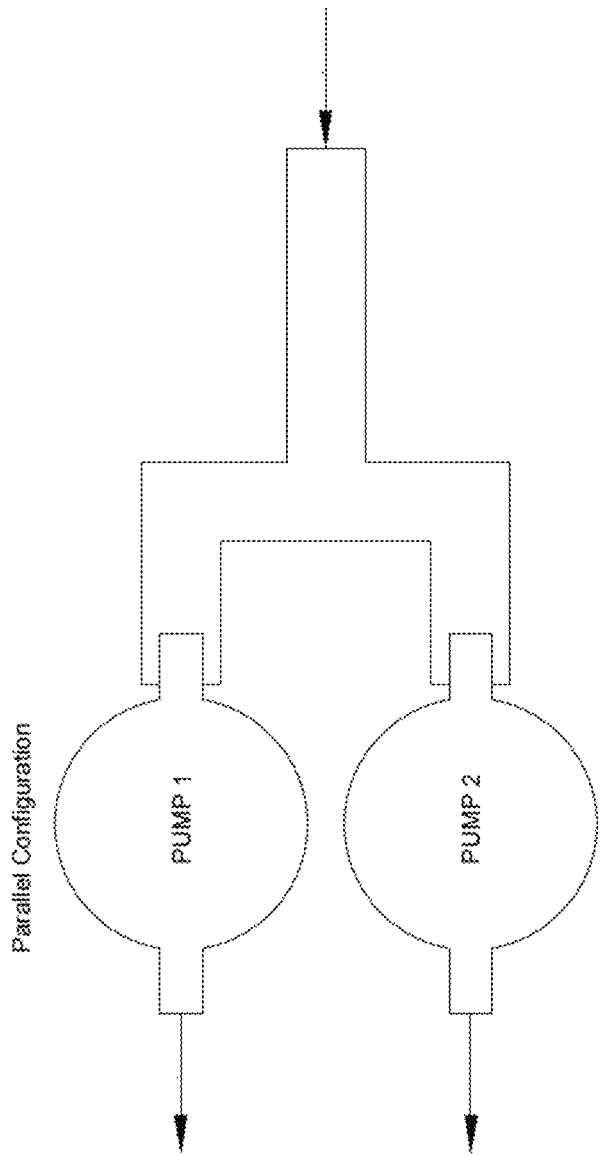
FIG. 41 shows a configuration of two piezo pumps mounted in parallel.

With reference to FIG. 41, a diagram illustrating a configuration of two piezo pumps mounted in parallel is shown.

Figure 42:
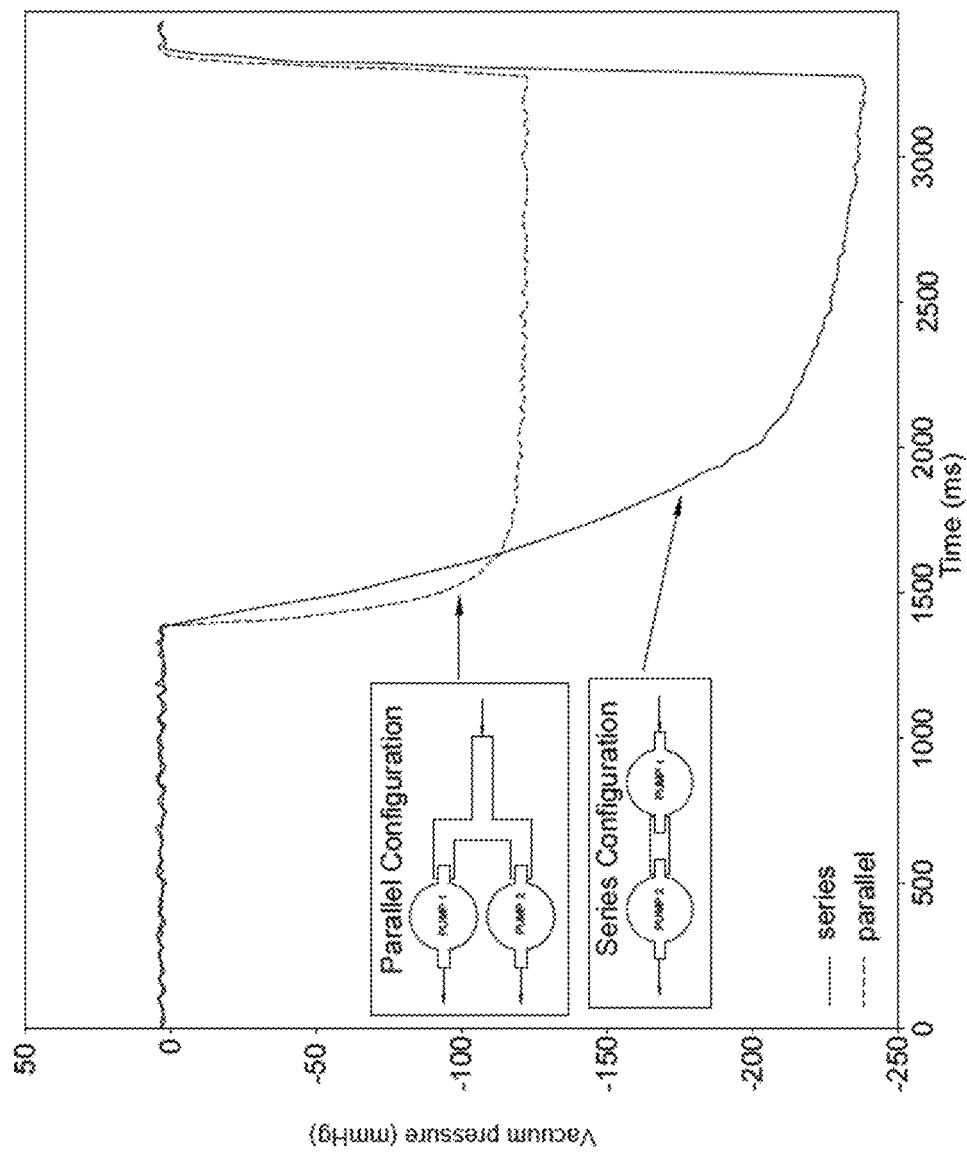
FIG. 42 shows a plot of the air pressure generated as a function of time by two piezo pumps mounted in series and mounted in parallel respectively.

With reference to FIG. 42, the air pressure generated as a function of time by two piezo pumps mounted in series and two piezo pumps mounted in parallel are compared. In this example, the parallel configuration produces higher flow rate and achieves −100 mmHg negative air pressure faster than the series configuration. In comparison, the series configuration produces lower flow rate and takes slightly longer to reach 100 mmHg. However, the parallel configuration cannot achieve as high as a vacuum as the series configuration and plateaus at −140 mmHg. In comparison, the series configuration is able to generate about −240 mmHg.

A dual configuration is also implemented in which more than one piezo pump is configured such that they can easily switch between a parallel mode and a series mode. This dual configuration would suit wearable devices that would need to achieve either lower or higher pressure faster.

Figure 43:
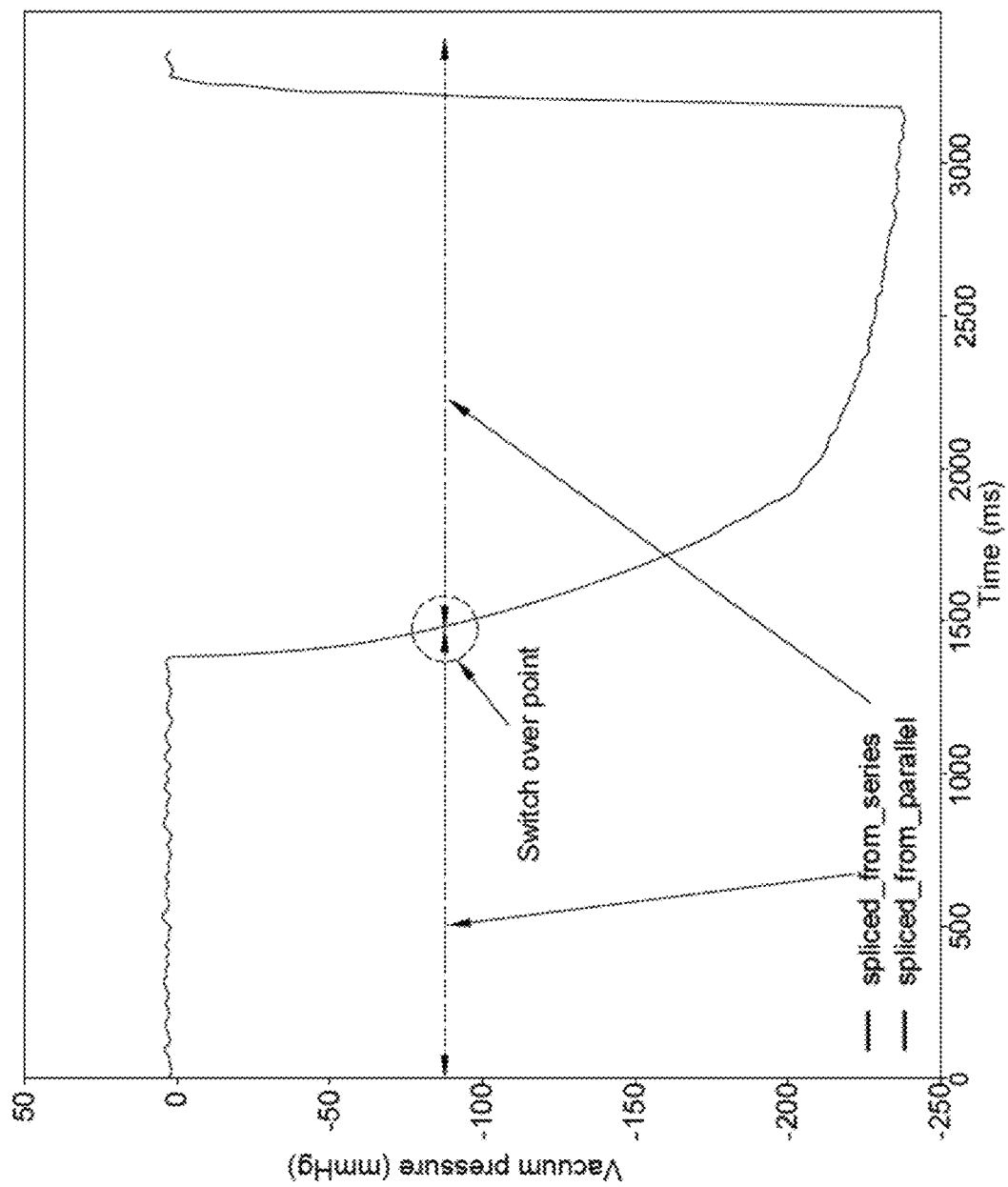
FIG. 43 shows a plot of the air pressure generated as a function of time by two piezo pumps mounted in a dual configuration.

FIG. 43 shows a plot of the air pressure generated as a function of time by two piezo pumps mounted in a dual configuration. In this dual configuration, the piezo pumps first start with a parallel mode in order to benefit from faster flow rate, and then switch to a series mode (as indicated by the switch-over point) when stronger vacuums are required, enabling to save up to 500 ms on cycle time with elastic loads.

Additionally, a piezo pump may be used in combination with a heat sink in order to efficiently manage the heat produced by the wearable pump. This configuration may be used to ensure that the wearable device can be worn comfortably. The heat sink or heat sinks are configured to ensure that the maximum temperature of any parts of the breast pump system that might come into contact with the skin (especially prolonged contact for greater than 1 minute) are no more than 48° C. and preferably no more than 43° C.

The heat sink may store the heat produced by a piezo pump in order to help diverting the heat produced to another location. This not only ensures that the wearable system can be worn comfortably, but also increases the lifetime of a piezo pump.

Figure 44:
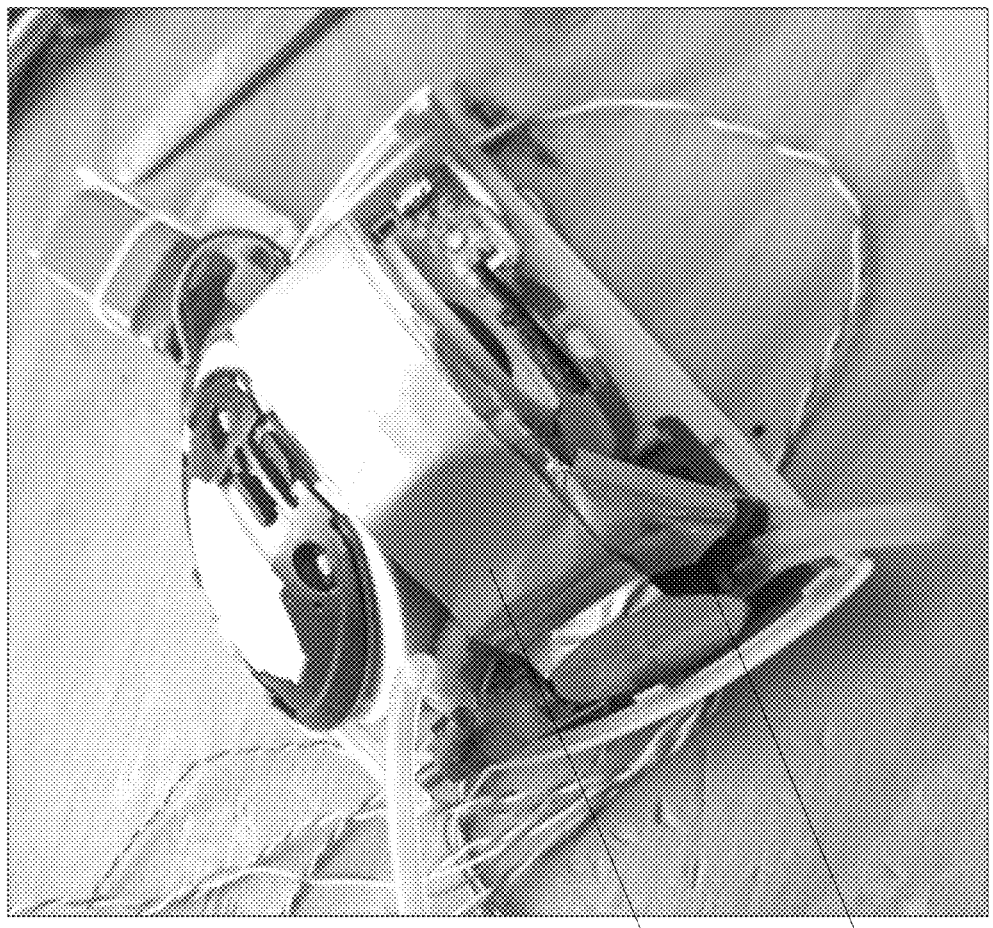
FIG. 44 shows a figure of a pump including two piezo pumps in which each piezo pump is connected to a heat sink.

FIG. 44 shows a picture of a wearable breast pump housing including multiple piezo pumps (440). The breast pump system is wearable and the housing is shaped at least in part to fit inside a bra. By applying a voltage to the piezo pumps, the pressure provided by the pumps increase. The generation of higher pressure by the piezo pumps also means higher heat produced that needs to be managed. Each piezo pump is therefore connected to a heat sink (441), such as a thin sheet of copper. The heat sink has a long thermal path length that diverts the heat away from the piezo pump.

The use of a heat sink in combination with a piezo pump is particularly relevant when the wearable device is worn directly or near the body, and where the management of heat induced by the piezo pump is crucial.

A wearable device including a piezo pump may therefore include a thermal cut out, and may allow for excess heat to be diverted to a specific location. The heat sink may be connected to an air exhaust so that air warmed by the piezo pumps vents to the atmosphere. For example, the wearable system is a breast pump system and the heat sink stores heat, which can then be diverted to warm the breast shield of the breast pump system.

Use cases application include but are not limited to:
Wound therapy;
High degree burns;
Sleep apnoea;
Deep vein thrombosis;
Sports injury.

APPENDIX: SUMMARY OF KEY FEATURES

In this section, we summarise the various features implemented in the Elvie™ pump system. We organize these features into six broad categories:

A. Elvie Breast Pump: General Usability Feature Cluster
B. Elvie Piezo Air Pump Feature Cluster
C. Elvie Milk Container Feature Cluster
D. Elvie IR System Feature Cluster
E. Elvie Bra Clip Feature Cluster
F. Other Features, outside the breast pump context Drilling down, we now list the features for each category:

A. Elvie Breast Pump: General Usability Feature Cluster

Feature 1 Elvie is wearable and includes only two parts that are removable from the pump main housing in normal use.

Feature 2 Elvie is wearable and includes a clear breast shield giving an unobstructed view of the breast for easy nipple alignment.

Feature 3 Elvie is wearable and includes a clear breast shield with nipple guides for easy breast shield sizing.

Feature 4 Elvie is wearable and includes a breast shield that audibly attaches to the housing.

Feature 5 Elvie is wearable and includes a breast shield that attaches to the housing with a single push.

Feature 6 Elvie is wearable and not top heavy, to ensure comfort and reliable suction against the breast.

Feature 7 Elvie is wearable and has a Night Mode for convenience.

Feature 8 Elvie is wearable and includes a haptic or visual indicator showing when milk is flowing or not flowing well.

Feature 9 Elvie is wearable and collects data to enable the mother to understand what variables (e.g. time of day, pump speed etc.) correlate to good milk-flow.

Feature 10 Elvie is wearable and collects data that can be exported to social media.

Feature 11 Elvie is wearable and has a smart bottle that stores the time and/or date of pumping to ensure the milk is used when fresh.

Feature 12 A smart bottle that stores the time and/or date of pumping to ensure the milk is used when fresh.

Feature 13 Elvie is wearable and includes a sensor to infer the amount of movement or tilt angle during normal use.

Feature 14 Elvie includes a control to toggle between expressing milk from the left breast and the right breast.

Feature 15 Elvie includes a pressure sensor.

Feature 16 Elvie includes a microcontroller to enable fine tuning between pre-set pressure profiles.

Feature 17 Elvie enables a user to set the comfort level they are experiencing.

Feature 18 Elvie includes a microcontroller to dynamically and automatically alter pump operational parameters.

Feature 19 Elvie automatically learns the optimal conditions for let-down.

B. Elvie Piezo Air Pump Feature Cluster

Feature 20 Elvie is wearable and has a piezo air-pump for quiet operation.

Feature 21 Elvie has a piezo air-pump and self-sealing diaphragm

Feature 22 Elvie uses more than one piezo air pump in series.

Feature 23 Elvie is wearable and has a piezo air-pump, a breast shield and a diaphragm that fits directly onto the breast shield.

Feature 24 Elvie is wearable and has a piezo air-pump for quiet operation and a re-useable, rigid milk container for convenience.

Feature 25 Elvie has a piezo-pump for quiet operation and is a connected device.

Feature 26 Elvie uses a piezo in combination with a heat sink that manages the heat produced by the pump.

Feature 27 Elvie is wearable and gently massages a mother's breast using small bladders inflated by air from its negative pressure air-pump.

Feature 28 Elvie is wearable and gently warms a mother's breast using small chambers inflated by warm air from its negative pressure air-pump.

C. Elvie Milk Container Feature Cluster

Feature 29 Elvie is wearable and includes a re-useable, rigid milk container that forms the lower part of the pump, to fit inside a bra comfortably.

Feature 30 Elvie is wearable and includes a milk container that latches to the housing with a simple push to latch action.

Feature 31 Elvie is wearable and includes a removable milk container with an integral milk pouring spout for convenience.

Feature 32 Elvie is wearable and includes a removable milk container below the milk flow path defined by a breast shield for fast and reliable milk collection.

Feature 33 Elvie is wearable and includes a breast shield and removable milk container of optically clear, dishwasher safe plastic for ease of use and cleaning.

Feature 34 Elvie is wearable and includes various components that self-seal under negative air pressure, for convenience of assembly and disassembly.

Feature 35 Elvie is wearable and includes a spout at the front edge of the milk container for easy pouring.

Feature 36 Elvie is wearable and includes a milk container that is shaped with broad shoulders and that can be adapted as a drinking bottle that baby can easily hold.

D. Elvie IR System Feature Cluster

Feature 37 Elvie is wearable and includes a light-based system that measures the quantity of milk in the container for fast and reliable feedback.

Feature 38 The separate IR puck for liquid quantity measurement.

Feature 39 The separate IR puck combined with liquid tilt angle measurement.

E. Bra Clip Feature

Feature 40 Bra Adjuster.

F. Other Features that can Sit Outside the Breast Pump Context

Feature 41 Wearable device using more than one piezo pump connected in series or in parallel.

Feature 42 Wearable medical device using a piezo pump and a heat sink attached together.

We define these features in terms of the device; methods or process steps which correspond to these features or implement the functional requirements of a feature are also covered.

We'll now explore each feature 1-42 in depth. Note that each feature can be combined with any other feature; any sub-features described as 'optional' can be combined with any other feature or sub-feature.

A. Elvie Breast Pump: General Usability Feature Cluster

Feature 1 Elvie is Wearable and Includes Only Two Parts that are Removable from the Pump Main Housing in Normal Use A wearable breast pump system including:

(a) a housing shaped at least in part to fit inside a bra and including a pumping mechanism;

(b) a breast shield;

(c) a rigid or non-collapsible milk container and in which the breast pump system includes only two parts that are directly removable from the housing in normal use or normal dis-assembly: the breast shield and the rigid, non-collapsible milk container.

Optional:

The only parts of the system that come into contact with milk in normal use are the breast shield and the milk container.

Milk only flows through the breast shield and then directly into the milk container.

The breast shield and milk container are each pressed or pushed into engagement with the housing.

The breast shield and milk container are each pressed or pushed into a latched engagement with the housing.

The two removable parts are each insertable into and removable from the housing using an action confirmed with an audible sound, such as a click.

Breast shield is a one-piece item including a generally convex surface shaped to fit over a breast and nipple tunnel shaped to receive a nipple.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Breast shield slides into the housing using guide members.

housing is configured to slide onto the breast shield, when the breast shield has been placed onto a breast, using guide members.

Breast shield latches into position against the housing.

Breast shield latches into position against the housing when spring plungers, such as ball bearings, in the housing locate into small indents in the breast shield.

Breast shield latches into position against the housing using magnets.

Breast shield includes or operates with a flexible diaphragm that (a) flexes when negative air pressure is applied to it by an air pump system in the housing, and (b) transfers that negative air-pressure to pull the breast and/or nipple against the breast shield to cause milk to be expressed.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

No other parts are removable from the breast shield, apart from the flexible diaphragm.

The milk container attaches to a lower surface of the housing and forms the base of the breast pump system in use.

The milk container mechanically or magnetically latches to the housing.

The milk container is released by the user pressing a button on the housing.

The milk container includes a removable cap and a removable valve that is seated on the lid.

In normal use, the milk container is positioned entirely within a bra.

No other parts are removable from the milk container, apart from the cap and the valve.

All parts that are user-removable in normal use are attached to either the breast shield or the milk container.

Audible or haptic feedback confirms the pump system is properly assembled for normal use with the milk container locked to the housing and the breast shield locked to the housing.

Pumping mechanism is a closed loop negative air-pressure system that applies negative pressure to a region surrounding a woman's breast to pump milk form that breast.

Feature 2 Elvie is Wearable and Includes a Clear Breast Shield Giving an Unobstructed View of the Breast for Easy Nipple Alignment A wearable breast pump system including:

(a) a housing shaped at least in part to fit inside a bra and including a pumping mechanism;

(b) and a breast shield including a substantially transparent nipple tunnel, shaped to receive a nipple, providing to the mother placing the breast shield onto her breast a clear and unobstructed view of the nipple when positioned inside the nipple tunnel, to facilitate correct nipple alignment.

Optional:

The breast shield is configured to provide to the mother a clear and unobstructed view of the nipple when the breast shield is completely out, of or separated from, the housing.

The breast shield is configured to provide to the mother a clear and unobstructed view of the nipple when the breast shield is partially out of, or partially separated from, the housing.

Entire breast shield is substantially transparent.

Breast shield is a one-piece item including a generally convex surface shaped to fit over a breast.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Housing is configured to slide onto the breast shield, when the breast shield has been placed onto a breast, using guide members.

Breast shield latches into position against the housing.

Breast shield latches into position against the housing when spring plungers, such as ball bearings in the housing locate into small indents in the breast shield.

Breast shield latches into position against the housing using magnets.

Breast shield includes or operates with a flexible diaphragm that (a) flexes when negative air pressure is applied to it by an air pump system in the housing, and (b) transfers that negative air-pressure to pull the breast and/or nipple against the breast shield to cause milk to be expressed.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

Nipple tunnel includes on its lower surface an opening through which expressed milk flows.

Pumping mechanism is a closed loop negative air-pressure system that applies negative pressure to a region surrounding a woman's breast to pump milk form that breast.

A milk container attaches to a lower surface of the housing and forms the base of the breast pump system in use.

The milk container mechanically or magnetically latches to the housing.

The milk container is released by the user pressing a button on the housing.

The milk container includes a removable cap and a removable valve that is seated on the lid.

In normal use, the milk container is positioned entirely within a bra.

Feature 3 Elvie is Wearable and Includes a Clear Breast Shield with Nipple Guides for Easy Breast Shield Sizing A wearable breast pump system including:

(a) a housing shaped at least in part to fit inside a bra and including a pumping mechanism;

(b) and a breast shield including a substantially transparent nipple tunnel shaped to receive a nipple, the nipple tunnel including guide lines that define the correct spacing of the nipple from the side walls of the nipple tunnel.

Optional:

The guide lines run generally parallel to the sides of the nipple placed within the nipple tunnel.

Breast shield is selected by the user from a set of different sizes of breast shield to give the correct spacing.

Breast shield is a one-piece item including a generally convex surface shaped to fit over a breast.

Breast shield is generally symmetrical about a centre-line running from the top to the bottom of the breast shield when positioned upright for normal use.

Breast shield is configured to be rotated smoothly around the nipple inserted into the nipple tunnel to position a diaphragm housing portion of the breast shield at the top of the breast.

Housing is configured to slide onto the breast shield, when the breast shield has been placed onto a breast, using guide members.

Breast shield latches into position against the housing.

Breast shield latches into position against the housing when spring plungers in the housing locate into small indents in the breast shield.

Breast shield latches into position against the housing using magnets.

Breast shield includes or operates with a flexible diaphragm that (a) flexes when negative air pressure is applied to it by an air pump system in the housing, and (b) transfers that negative air-pressure to pull the breast and/or nipple against the breast shield to cause milk to be expressed.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

Nipple tunnel includes on its lower surface an opening through which expressed milk flows.

Pumping mechanism is a closed loop negative air-pressure system that applies negative pressure to a region surrounding a woman's breast to pump milk form that breast.

Feature 4 Elvie is Wearable and Includes a Breast Shield that Audibly Attaches to the Housing.

A wearable breast pump system including:

(a) a housing shaped at least in part to fit inside a bra and including a pumping mechanism;

(b) and a breast shield that is attachable to the housing with a mechanism that latches with an audible click when the breast shield is slid on to or against the housing with sufficient force.

Optional:

The breast shield is configured to slide onto or against the housing in a direction parallel to the long dimension of a nipple tunnel in the breast shield.

Breast shield is removable from the housing with an audible click when the breast shield is pulled away from the housing with sufficient force.

Breast shield is a one-piece item including a generally convex surface shaped to fit over a breast.

Breast shield is generally symmetrical about a centre-line running from the top to the bottom of the breast shield when positioned upright for normal use.

Breast shield is configured to be rotated smoothly around the nipple inserted into the nipple tunnel to position a diaphragm housing portion of the breast shield at the top of the breast.

Housing is configured to slide onto the breast shield, when the breast shield has been placed onto a breast, using guide members.

Breast shield latches into position against the housing.

Breast shield latches into position against the housing when spring plungers, such as ball bearings in the housing locate into small indents in the breast shield.

Breast shield latches into position against the housing using magnets.

Breast shield includes or operates with a flexible diaphragm that (a) flexes when negative air pressure is applied to it by an air pump system in the housing, and (b) transfers that negative air-pressure to pull the breast and/or nipple against the breast shield to cause milk to be expressed.

The edge of the flexible diaphragm seals, self-seals, self-energising seals, or interference fit seals against the housing when the breast shield attaches to the housing.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

Nipple tunnel includes on its lower surface an opening through which expressed milk flows.

Pumping mechanism is a closed loop negative air-pressure system that applies negative pressure to a region surrounding a woman's breast to pump milk form that breast.

Feature 5 Elvie is Wearable and Includes a Breast Shield that Attaches to the Housing with a Single Push A wearable breast pump system including:

(a) a housing shaped at least in part to fit inside a bra and including a pumping mechanism;

(b) and a breast shield configured to attach to the housing with a single, sliding push action.

Optional:

The breast shield is configured to slide onto or against the housing in a direction parallel to the long dimension of a nipple tunnel in the breast shield.

The single push action overcomes a latching resistance.

Breast shield is a one-piece item including a generally convex surface shaped to fit over a breast.

Breast shield is generally symmetrical about a centre-line running from the top to the bottom of the breast shield when positioned upright for normal use.

Breast shield is configured to be rotated smoothly around a nipple inserted into a nipple tunnel in the breast shield to position a diaphragm housing portion of the breast shield at the top of the breast.

Housing is configured to slide onto the breast shield when the breast shield has been placed onto a breast using guide members.

Breast shield latches into position against the housing.

Breast shield latches into position against the housing when spring plungers, such as ball bearings in the housing locate into small indents in the breast shield.

Breast shield latches into position against the housing using magnets.

Breast shield includes or operates with a flexible diaphragm that (a) flexes when negative air pressure is applied to it by an air pump system in the housing, and (b) transfers that negative air-pressure to pull the breast and/or nipple against the breast shield to cause milk to be expressed.

The edge of the flexible diaphragm seals, self-seals, self-energising seals, or interference fit seals against the housing when the breast shield attaches to the housing.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

Nipple tunnel includes on its lower surface an opening through which expressed milk flows.

Pumping mechanism is a closed loop negative air-pressure system that applies negative pressure to a region surrounding a woman's breast to pump milk form that breast.

A milk container attaches to a lower surface of the housing and forms the base of the breast pump system in use.

The milk container mechanically or magnetically latches to the housing.

The milk container is released by the user pressing a button on the housing.

The milk container includes a removable cap and a removable valve that is seated on the lid.

In normal use, the milk container is positioned entirely within a bra.

Feature 6 Elvie is Wearable and not Top Heavy, to Ensure Comfort and Reliable Suction Against the Breast A wearable breast pump system including:

(a) a housing shaped at least in part to fit inside a bra and including a pumping mechanism (b) and a breast shield;

(c) a milk container and in which the centre of gravity of the pump system is, when the milk container is empty, substantially at or below (i) the half-way height line of the housing or (ii) the horizontal line that passes through a nipple tunnel or filling point on a breast shield, so that the device is not top-heavy for a woman using the pump.

Optional:

The milk container is a re-useable milk container that when connected to the housing is positioned to form the base of the housing.

In which the centre of gravity only moves lower during use as the milk container gradually receives milk, which increases the stability of the pump inside the bra.

In which milk only passes downwards when moving to the milk container, passing through the nipple tunnel and then through an opening in the lower surface of the nipple tunnel directly into the milk container, or components that are attached to the milk container.

System is configured so that its centre of gravity is no more than 60 mm up from the base of the milk container also below the top of the user's bra cup.

In which the pumping mechanism and the power supply for that mechanism are positioned within the housing to provide a sufficiently low centre of gravity.

In which the pumping mechanism is one or more piezo air pumps, and the low weight of the piezo air pumps enables the centre of gravity to be substantially at or below (i) the half-way height line of the housing or (ii) the horizontal line that passes through the nipple tunnel or filling point on the breast shield.

In which the pumping mechanism is one or more piezo air pumps, and the small size of the piezo air pumps enables the components in the housing to be arranged so that the centre of gravity is substantially at or below (i) the half-way height line of the housing or (ii) the horizontal line that passes through the nipple tunnel or filling point on the breast shield.

In which the pumping mechanism is one or more piezo air pumps, and the low weight of the battery or batteries needed to power that piezo air pumps enables the centre of gravity to be substantially at or below (i) the half-way height line of the housing or (ii) the horizontal line that passes through the nipple tunnel or filling point on the breast shield.

Pumping mechanism is a closed loop negative air-pressure system that applies negative pressure to a region surrounding a woman's breast to pump milk form that breast.

Feature 7 Elvie is Wearable and has a Night Mode for Convenience

A breast pump system including:

(a) a housing including a pumping mechanism;

(b) an illuminated control panel;

(c) a control system that reduces or adjusts the level or colour of illumination of the control panel at night or when stipulated by the user.

Optional:

The breast pump is wearable and the housing is shaped at least in part to fit inside a bra.

Control system is implemented in hardware in the pump itself using a 'night mode' button.

Control system is implemented in software within a connected device app running on the user's smartphone.

Control system is linked to the illumination level on a connected device app., so that when the connected app is in 'night mode', the illuminated control panel is also in 'night mode', with a lower level of illumination, and when the illuminated control panel on the housing is in 'night mode', then the connected app is also in 'night mode'.

Pumping mechanism is a closed loop negative air-pressure system that applies negative pressure to a region surrounding a woman's breast to pump milk form that breast. The pumping mechanism is one or more piezo air pumps, selected for quiet operation.

Feature 8 Elvie is Wearable and Includes a Haptic or Visual Indicator Showing when Milk is Flowing or not Flowing Well A wearable breast pump system including:

(a) a housing shaped at least in part to fit inside a bra and including a pumping mechanism;

(b) a milk container that is configured to be concealed within a bra and is hence not visible to the mother in normal use;

(c) a visual and/or haptic indicator that indicates whether milk is flowing or not flowing into the milk container.

Optional:

A haptic and/or visual indicator indicates if the pump is operating correctly to pump milk, based on whether the quantity and/or the height of the liquid in the container above its base is increasing above a threshold rate of increase The visual indicator is a row of LEDs that changes appearance as the quantity of liquid increases.

The haptic and/or visual indicator provides an indication of an estimation of the flow rate.

The visual indicator provides a colour-coded indication of an estimation of the flow rate.

The visual indicator provides an indication of how much of the container has been filled.

The visual indicator is part of a user interface in a connected, companion application, running on a smartphone or other personal device, such as a smart watch or smart ring.

The haptic indicator is part of a user interface in a connected, companion application, running on a smartphone or other personal device, such as a smart watch or smart ring.

A sub-system measures or infers the quantity and/or the height of the liquid in the container.

The sub-system measures or infers the quantity and/or the height of the liquid in the container by using one or more light emitters and light detectors to detect light from the emitters that has been reflected by the liquid, and measuring the intensity of that reflected light.

Sub-system includes or communicates with an accelerometer and uses a signal from the accelerometer to determine if the liquid is sufficiently still to permit the sub-system to accurately measure or infer the quantity and/or the height of the liquid in the container.

A sub-system measures or infers the angle the top surface of the liquid in the container makes with respect to a baseline, such as the horizontal.

A haptic and/or visual indicator indicates if the amount of milk in the milk container has reached a preset quantity or level.

A haptic and/or visual indicator indicates if there is too much movement of the breast pump system for viable operation.

Milk container is attached to the lower part of the housing and forms the base of the breast pump system.

Milk container is made of transparent material.

Pumping mechanism is a closed loop negative air-pressure system that applies negative pressure to a region surrounding a woman's breast to pump milk form that breast.

Feature 9 Elvie is Wearable and Collects Data to Enable the Mother to Understand What Variables (e.g. Time of Day, Pump Speed Etc.) Correlate to Good Milk-Flow A breast pump system including:
(a) a housing including a pumping mechanism;
(b) a milk container
(c) a measurement sub-system that measures or infers milk flow into the milk container,
and in which the measurement sub-system provides data to a data analysis system that determines metrics that correlate with user-defined requirements for milk-flow rate or milk expression.

Optional:

The breast pump is wearable and the housing is shaped at least in part to fit inside a bra.

User-defined requirement is to enhance or increase milk-flow.

User-defined requirement is to reduce milk-flow.

The data analysis system analyses data such as any of the following: amount of milk expressed over one or more sessions, rate at which milk is expressed over one or more sessions, profile of the rate at which milk is expressed over one or more sessions.

The data analysis system determines metrics such as any of the following pump speed, length of a single pumping session, negative air pressure or vacuum level, peak negative air pressure or vacuum level, pump cycle time or frequency, changing profile of pump speed over a single pumping session time of day.

The data analysis system determines metrics such as any of the following amount and type of liquids consumed by the mother, state of relaxation of the mother before or during a session, state of quiet experienced by the mother before or during a session, what overall milk expression profile the mother most closely matches.

Data analysis system is local to the breast pump system, or runs on a connected device, such as a smartphone, or is on a remote server or is on the cloud, or is any combination of these.

measurement sub-system measures or infers the quantity and/or the height of the liquid in the container above its base.

Measurement sub-system measures or infers angle the top surface of the liquid in the container makes with respect to a baseline, such as the horizontal.

Data analysis system gives recommended metrics for improving milk flow

Data analysis system gives recommended metrics for weaning.

Data analysis system gives recommended metrics for increasing milk supply (e.g. power pumping).

Data analysis system gives recommended metrics if an optimal session start time or a complete session has been missed.

Data analysis system leads to automatic setting of metrics for the pumping mechanism, such as pump speed, length of a single pumping session, vacuum level, cycle times, changing profile of pump speed over a single pumping session.

Data analysis system enables sharing across large numbers of connected devices or apps information that in turn optimizes the milk pumping or milk weaning efficacy of the breast pump.

Metrics include the specific usage of the connected device by a woman while using the pump (for example by the detection of vision and/or audio cues).

The measurement sub-system measures or infers the quantity and/or the height of the liquid in the container.

The measurement sub-system measures or infers the quantity and/or the height of the liquid in the container by using one or more light emitters and light detectors to detect light from the emitters that has been reflected by the liquid, and measuring the intensity of that reflected light.

The measurement sub-system includes or communicates with an accelerometer and uses a signal from the accelerometer to determine if the liquid is sufficiently still to permit the measurement sub-system to accurately measure or infer the quantity and/or the height of the liquid in the container.

Milk container is a re-useable milk container that when connected to the housing is positioned to form the base of the housing.

Pumping mechanism is a closed loop negative air-pressure system that applies negative pressure to a region surrounding a woman's breast to pump milk form that breast.

Feature 10 Elvie is Wearable and Collects Data that can be Exported to Social Media.

A breast pump system including:
(a) a housing including a pumping mechanism;
(b) a milk container,
(c) a data sub-system that collects and provides data to a connected device or remote application or remote server, (d) and in which the collected data, in whole or in part, is used by a data analysis system that provides inputs to a social media or community function or platform.

Optional:
- The breast pump is wearable and the housing is shaped at least in part to fit inside a bra.
- The data analysis system analyses metrics such as any of the following: amount of milk expressed over one or more sessions, rate at which milk is expressed over one or more sessions, profile of the rate at which milk is expressed over one or more sessions.
- The data analysis system analyses metrics such as any of the following pump speed, length of a single pumping session, negative air pressure or vacuum level, peak negative air pressure or vacuum level, pump cycle time or frequency, changing profile of pump speed over a single pumping session time of day.
- The data analysis system analyses metrics such as any of the following amount and type of liquids consumed by the mother, state of relaxation of the mother before or during a session, state of quiet experienced by the mother before or during a session, what overall milk expression profile the mother most closely matches.
- Data analysis system is local to the breast pump system, or runs on a connected device, such as a smartphone, or is on a remote server or is on the cloud, or is any combination of these.
- The social media or community function or platform organizes the collected data into different profiles.
- The social media or community function or platform enables a user to select a matching profile from a set of potential profiles.
- each profile is associated with a specific kind of milk expression profile, and provides information or advice that is specifically relevant to each milk expression profile.
- Information or advice includes advice on how to increase milk expression by varying parameters, such as time of milk expression, frequency of a milk expression session, pump speed, length of a single pumping session, vacuum level, cycle times, changing profile of pump speed over a single pumping session and any other parameter that can be varied by a mother to help her achieve her milk expression goals.
- The application is connected to other applications residing on the connected device, such as a fitness app.
- The collected data includes data received from other connected apps.
- The collected data is anonymised before it is shared.
- The sub-system includes a wi-fi connectivity component for direct connectivity to a remote server.
- The milk container is a re-useable milk container that when connected to the housing is positioned to form the base of the housing.
- Pumping mechanism is a closed loop negative air-pressure system that applies negative pressure to a region surrounding a woman's breast to pump milk form that breast.

Feature 11 Elvie is Wearable and has a Smart Bottle that Stores the Time and/or Date of Pumping to Ensure the Milk is Used when Fresh A breast pump system including a pumping mechanism and a milk container and including:
(a) a housing including the pumping mechanism;
(b) a milk container,
(c) and in which the milk container or any associated part, such as a lid, includes a memory or tag that is automatically programmed to store the time and/or date it was filled with milk.

Optional:
- The breast pump is wearable and the housing is shaped at least in part to fit inside a bra.
- Memory or tag is programmed to store the quantity of milk in the milk container.
- Memory or tag stores the milk expiry date.
- Memory or tag stores a record of the temperature of the milk or the ambient temperature around the milk, and calculates an expiry date using that temperature record.
- System includes a clock and writes the time and/or date the milk container was filled with milk to the memory or tag on the milk container.
- Clock is in the housing.
- Clock is in the milk container.
- Milk container includes a display that shows the time and/or date it was filled with milk.
- Milk container includes a display that shows the quantity of milk that it was last filled with milk.
- Milk container includes a display that shows whether the left or right breast was used to fill the milk container.
- Memory or tag is connected to a data communications sub-system.
- Memory or tag is a remotely readable memory or tag, such as a NFC tag, enabling a user to scan the milk container with a reader device, such as a smartphone, and have the time and/or date that container was filled with milk, displayed on the reader device.
- Reader device shows the time and/or date a specific milk container was filled with milk.
- Reader device shows the quantity of milk that a specific milk container was last filled with.
- Reader device shows the time and/or date and/or quantity that each of several different milk containers were filled with.
- Reader device shows whether the left or right breast was used to fill the milk contained in a specific milk container.
- A sub-system measures or infers milk flow into the milk container.
- The sub-system measures or infers the quantity and/or the height of the liquid in the container.
- The sub-system measures or infers the quantity and/or the height of the liquid in the container by using one or more light emitters and light detectors to detect light from the emitters that has been reflected by the liquid, and measuring the intensity of that reflected light.
- Sub-system includes an accelerometer and uses a signal from the accelerometer to determine if the liquid is sufficiently still to permit the sub-system to accurately measure or infer the quantity and/Tr the height of the liquid in the container.
- The sub-system is in the housing.
- Milk container is a re-useable milk container that when connected to the housing is positioned to form the base of the housing.
- Pumping mechanism is a closed loop negative air-pressure system that applies negative pressure to a region surrounding a woman's breast to pump milk form that breast.

Feature 12 a Smart Bottle that Stores the Time and/or Date of Pumping to Ensure the Milk is Used when Fresh.

A smart bottle or container that includes or is associated with a memory or a tag that is programmed to store the date and time it is filled using data from a pump or a connected device, such as a smartphone.

Optional:
The container includes wireless connectivity and connects to a companion app.
The memory or tag includes an NFC chip and is read using a NFC reader.
The memory or tag stores also an expiry date.
Memory or tag stores a record of the temperature of the milk or the ambient temperature around the milk, and calculates an expiry date using that temperature record.
The memory or tag stores also the quantity of milk stored.
System includes a clock and writes the time and/or date the milk container was filled with milk to the memory or tag on the milk container.
Clock is in the housing.
Clock is in the container.
Milk container includes a display that shows the time and/or date it was filled with milk.
Milk container includes a display that shows the quantity of milk that it was last filled with milk.
Milk container includes a display that shows whether the left or right breast was used to fill the milk contained.
Milk container includes a display that shows the expiry date.
memory or tag is connected to a data communications sub-system.
Memory or tag is a remotely readable memory or tag, such as a NFC tag, enabling a user to scan the milk container with a reader device, such as a smartphone.
Reader device shows the time and/or date a specific milk container was filled with milk.
Reader device shows the quantity of milk that a specific milk container was last filled with.
Reader device shows the time and/or date and/or quantity that each of several different containers were filled with.
Reader device shows whether the left or right breast was used to fill the milk contained in a specific milk container.
Reader device shows the expiry date.
Container includes wireless connectivity and connects to a companion application.
An application tracks status of one or more smart containers and enables a user to select an appropriate smart container for a feeding session.
The pump is wearable.
The pump is in a housing shaped to fit inside a bra and the container is a milk container that is connected to the housing and is positioned to form the base of the housing.
Container is used for liquids other than milk.

Feature 13 Elvie is Wearable and Includes a Sensor to Infer the Amount of Movement or Tilt Angle During Normal Use.

A breast pump system including:
(a) a housing;
(b) a milk container
(c) the housing including a sensor, such as an accelerometer, that measures or determines the movement and/or tilt angle of the housing, during a pumping session and automatically affects or adjusts the operation of the system depending on the output of the sensor.

Optional:
The breast pump is wearable and the housing is shaped at least in part to fit inside a bra.
If the tilt angle of the housing exceeds a threshold, then the system automatically affects the operation of the system by warning or alerting the mother of a potential imminent spillage (e.g. from milk flowing back out of a breast shield) using an audio, or visual or haptic alert, or a combination of audio, haptic and visual alerts.
If the tilt angle of the housing exceeds a threshold, then the system automatically adjusts the operation of the system by stopping the pump to prevent spillage.
When the tilt angle of the housing reduces below the threshold, the system automatically adjusts the operation of the system by causing pumping to resume automatically.
If the tilt angle of the housing exceeds a threshold, then the system automatically affects the operation of the system by providing the mother with an alert to change position.
The container includes an optically clear region.
There are one or more light emitters and detectors positioned in the base of the housing, the light emitters and receivers operating as part of a sub-system that measures or infers the tilt angle of the milk in the container.
The sub-system measures the quantity of liquid in the milk container and also takes the measured tilt angle of the housing into account.
If the tilt angle is above a certain threshold, the system ignores the quantity of liquid measured.
The sub-system derives or infers the mother's activity, such as walking, standing or lying activities, from the sensor.
The milk container is a re-useable milk container that when connected to the housing is positioned to form the base of the housing.
Sub-system stores a time-stamped record of movement and/or tilt angles of the housing in association with milk flow data.
System includes a breast shield that attaches to the housing.
System includes a closed loop negative air-pressure system that applies negative pressure to a region surrounding a woman's breast to pump milk form that breast.

Feature 14 Elvie Includes a Control to Toggle Between Recording Whether Milk is being Expressed from the Left Breast and the Right Breast.

A wearable breast pump system including:
(a) a housing shaped at least in part to fit inside a bra;
(b) a control interface that the user can select to indicate or record if milk is being expressed from the left or the right breast.

Optional:
Control interface is a physical interface on the housing.
Control interface is a single button on the housing.
Control interface is from an application running on a device, such as a smartphone or smart ring.
Visual indicators on the housing indicate whether the breast pump system is being set up the left or the right breast.
The visual indicator for the left breast is on the right-hand side of the housing, when viewed from the front; and the visual indicator for the right breast is on the left-hand side of the housing, when viewed from the front.
The housing includes a button labeled to indicate the left breast and a button labeled to indicate the right breast, that are respectively illuminated to indicate from which breast the milk is being expressed.

Breast pump system is a closed loop negative air-pressure system that applies negative pressure to a region surrounding a woman's breast to pump milk form that breast.

Feature 15 Elvie Includes a Pressure Sensor.

A breast pump system including (i) a pumping mechanism that applies negative air-pressure and (ii) an air pressure sensor configured to measure the negative pressure delivered by the negative air-pressure mechanism and (iii) a measurement sub-system that measures or infers milk flow or milk volume.

Optional:
The system also includes a control sub-system that combines or relates the air-pressure measurements with the milk flow or milk volume measurements The control sub-system automatically adjusts the negative air-pressure to give the optimal milk flow or milk volume.

The control sub-system automatically adjusts the negative air-pressure during a pumping session to give the optimal milk flow or milk volume within comfort constraints defined by the user.

The air pressure sensor detects pressure created by the pumping mechanism.

Sensor is a piezo air pressure sensor

Air pressure sensor measures the negative air pressure during a normal milk expression session.

Air pressure sensor measures the negative air pressure during a calibration session, and the system uses the results to vary the operation of the pumping mechanism so that it deliver consistent performance over time.

Air pressure sensor measures the negative air pressure during a calibration session, and the system uses the results to vary the operation of the pumping mechanism so that different pumping mechanisms in different breast pump systems all deliver consistent performance Air pressure sensor measures the negative air pressure during a calibration session, and the system uses the results to determine if the pumping mechanism is working correctly, within tolerance levels.

The operation of the pumping mechanism is varied by altering the duty or pump cycle.

The operation of the pumping mechanism is varied by altering the voltage applied to the pumping mechanism.

Pumping mechanism is a piezo air pump.

Piezo air pump forms part of a closed or closed loop system.

The piezo-air pump is a closed loop negative air-pressure system that applies negative pressure to a flexible diaphragm that seals, self-seals, self-energising seals or interference fit seals against a diaphragm housing that forms part of a breast shield.

Breast pump system is wearable and includes a housing that is shaped at least in part to fit inside a bra.

Breast pump system includes a milk container and a measurement sub-system that automatically measures the quantity of milk in the milk container.

The measurement sub-system includes one or more light emitters and one or more light detectors, operating as part of a sub-system that measures or infers the quantity of the milk in the container and/or the height of the milk in the container above its base, and in which the light detectors detect and measure the intensity of the light from the emitters that has been reflected from the surface of the milk.

Feature 16 Elvie Includes a Microcontroller to Enable Fine Tuning Between Pre-Set Pressure Profiles A breast pump system including (i) a pumping mechanism that applies negative air-pressure and (ii) a microcontroller programmed to cause the pumping mechanism to deliver various pre-set pressure profiles and to permit the user to manually vary the pressure to a value or values that are in-between the values available from a pre-set pressure profile.

Optional:
The user manually varies the pressure using a control interface on a housing of the breast pump system The user manually varies the pressure using a control interface on an application running on a wireless device such as a smartphone that is wirelessly connected to the breast pump system.

The user manually varies the pressure by altering a control parameter of the pumping mechanism.

The user manually varies the pressure by altering the duty cycle or timing of the pumping mechanism.

The user manually varies the pressure by altering the voltage applied to the pumping mechanism.

The system includes an air pressure sensor configured to measure the negative air pressure delivered by the pumping mechanism.

The air pressure sensor is a piezo air pressure sensor.

Pumping mechanism is a piezo air pump.

Piezo air pump forms part of a closed or closed loop system.

The piezo-air pump is a closed loop negative air-pressure system that applies negative pressure to a flexible diaphragm that seals, self-seals, self-energising seals or interference fit seals against a diaphragm housing that forms part of a breast shield.

Pressure profile defines one or more maximum negative air pressure levels.

Pressure profile defines one or more maximum negative air pressure levels, each for a pre-set time.

Pressure profile defines one or more cycle time.

Pressure profile defines peak flow rate.

Breast pump system is wearable and includes a housing that is shaped at least in part to fit inside a bra.

Breast pump system includes a milk container and a measurement sub-system that automatically measures the quantity of milk in the milk container.

The measurement sub-system includes one or more light emitters and one or more light detectors, operating as part of a sub-system that measures or infers the quantity of the milk in the container and/or the height of the milk in the container above its base, and in which the light detectors detect and measure the intensity of the light from the emitters that has been reflected from the surface of the milk.

Feature 17 Elvie Enables a User to Set the Comfort Level they are Experiencing

A breast pump system including (i) a pumping mechanism that applies negative air-pressure and (ii) a microcontroller programmed to control the pumping mechanism and to permit the user to manually indicate the level of comfort that they are experiencing when the system is in use.

Optional:
The user manually indicates the level of comfort that they are experiencing using a touch or voice-based interface on a housing of the breast pump system The user manually indicate the level of comfort that they are experiencing using a touch or voice-based interface on an application running on a wireless device, such as a smartphone, that is wirelessly connected to the breast pump system.

The system stores user-indicated comfort levels together with associated parameters of the pumping system.

The system is a connected device and a remote server stores user-indicated comfort levels together with associated parameters of the pumping system.

The parameters of the pumping system include one or more of: pumping strength, peak negative air pressure; flow rate; voltage applied to the pumping mechanism; duty or timing cycle of the pumping mechanism.

System automatically varies parameters of the pumping system and then enables the user to indicate which parameters are acceptable.

System includes an air pressure sensor that measures the negative air pressure delivered by the pumping mechanism.

The air pressure sensor is a piezo air pressure sensor.

Pumping mechanism is a piezo air pump.

Piezo air pump forms part of a closed or closed loop system.

The piezo-air pump is a closed loop negative air-pressure system that applies negative pressure to a flexible diaphragm that seals, self-seals, self-energising seals or interference fit seals against a diaphragm housing that forms part of a breast shield.

Breast pump system is wearable and includes a housing that is shaped at least in part to fit inside a bra.

Breast pump system includes a milk container and a measurement sub-system that automatically measures the quantity of milk in the milk container.

The measurement sub-system includes one or more light emitters and one or more light detectors, operating as part of a sub-system that measures or infers the quantity of the milk in the container and/or the height of the milk in the container above its base, and in which the light detectors detect and measure the intensity of the light from the emitters that has been reflected from the surface of the milk.

Feature 18 Elvie Includes a Microcontroller to Dynamically and Automatically Alter Pump Operational Parameters A breast pump system including (i) a pumping mechanism that applies negative air-pressure and (ii) a microcontroller programmed to automatically change one or more parameters of the pumping mechanism, and to automatically measure or relate milk expression data as a function of different values of one or more of these parameters.

Optional:

The milk expression data includes one or more of the following: milk expression rate or quantity; comfort; optimal pumping mode; optimal pumping mode given remaining battery power.

The system automatically calculates or identifies the parameters of the pumping mechanism that correlate with maximum milk expression rate or quantity and uses that set of parameters.

The system automatically calculates or identifies the parameters of the pumping mechanism that correlate with maximum milk expression rate or quantity and uses that set of parameters if the comfort experienced by the user when those parameters are used is above a threshold.

The system displays the parameters of the pumping mechanism that correlate with maximum milk expression rate or quantity to the user.

The system displays the parameters of the pumping mechanism that correlate with maximum milk expression rate or quantity to the user and enables the user to manually select those parameters if they are acceptable.

Parameters of the pumping mechanism includes pumping strength, peak negative air pressure; flow rate; voltage applied to the pumping mechanism; duty or timing cycle of the pumping mechanism.

System includes an air pressure sensor that measures the negative air pressure delivered by the pumping mechanism.

The air pressure sensor is a piezo air pressure sensor.

Pumping mechanism is a piezo air pump.

Piezo air pump forms part of a closed or closed loop system.

The piezo-air pump is a closed loop negative air-pressure system that applies negative pressure to a flexible diaphragm that seals, self-seals, self-energising seals or interference fit seals against a diaphragm housing that forms part of a breast shield.

Breast pump system is wearable and includes a housing that is shaped at least in part to fit inside a bra.

Breast pump system includes a milk container and a measurement sub-system that automatically measures the quantity of milk in the milk container.

The measurement sub-system includes one or more light emitters and one or more light detectors, operating as part of a sub-system that measures or infers the quantity of the milk in the container and/or the height of the milk in the container above its base, and in which the light detectors detect and measure the intensity of the light from the emitters that has been reflected from the surface of the milk.

Feature 19 Elvie Automatically Learns the Optimal Conditions for Let-Down

A breast pump system including (i) a pumping mechanism that applies negative air-pressure and (ii) a microcontroller programmed to dynamically change one or more parameters of the pumping mechanism, and to automatically detect the start of milk let-down.

Optional:

The microcontroller is programmed to dynamically change one or more parameters of the pumping mechanism, to enable it to learn or optimize the parameters relating to milk let-down.

The system automatically calculates or identifies or learns the parameters of the pumping mechanism that correlate with the quickest start of milk let-down.

The system automatically calculates or identifies or learns the parameters of the pumping mechanism that correlate with the quickest start of milk let-down and uses that set of parameters if the comfort experienced by the user when those parameters are used is above a threshold or are otherwise acceptable to the user.

The system displays the parameters of the pumping mechanism that correlate with the quickest start of milk let-down to the user.

The system displays the parameters of the pumping mechanism that correlate with the quickest start of milk let-down and enables the user to manually select those parameters if they are acceptable.

parameters of the pumping mechanism includes pumping strength, peak negative air pressure; flow rate; voltage applied to the pumping mechanism; duty or timing cycle of the pumping mechanism.

System includes an air pressure sensor that measures the negative air pressure delivered by the pumping mechanism.

The air pressure sensor is a piezo air pressure sensor.

Pumping mechanism is a piezo air pump.

Piezo air pump forms part of a closed or closed loop system.

The piezo-air pump is a closed loop negative air-pressure system that applies negative pressure to a flexible diaphragm that seals, self-seals, self-energising seals or interference fit seals against a diaphragm housing that forms part of a breast shield.

Breast pump system is wearable and includes a housing that is shaped at least in part to fit inside a bra.

Breast pump system includes a milk container and a measurement sub-system that automatically measures the quantity of milk in the milk container.

The measurement sub-system includes one or more light emitters and one or more light detectors, operating as part of a sub-system that measures or infers the quantity of the milk in the container and/or the height of the milk in the container above its base, and in which the light detectors detect and measure the intensity of the light from the emitters that has been reflected from the surface of the milk.

B. Elvie Piezo Air Pump Feature Cluster

Feature 20 Elvie is Wearable and has a Piezo Air-Pump for Quiet Operation

A wearable breast pump system including:

(a) a housing shaped at least in part to fit inside a bra;

(b) a piezo air-pump in the housing that is part of a closed loop system that drives, a separate, deformable diaphragm to generate negative air pressure.

Optional:

The deformable diaphragm inside the housing is driven by negative air pressure generated by the piezo pump.

Piezo air pump is positioned at or close to the base of the housing.

There are two or more piezo air pumps.

There are two or more piezo air pumps mounted in a series arrangement.

There are two or more piezo air pumps mounted in a parallel arrangement.

The closed system is separated from a 'milk' side by the flexible diaphragm.

Deformable diaphragm is removably mounted against a part of a breast shield.

Deformable diaphragm is a unitary or one-piece object that is removably mounted against a part of a breast shield.

Deformable diaphragm is not physically connected to the piezo air-pump.

Piezo air-pump is a closed loop air-pump that drives a physically separate and remote deformable diaphragm that removably fits directly onto the breast shield Deformable diaphragm is a flexible generally circular diaphragm that sits over a diaphragm housing that is an integral part of a breast shield.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

The piezo pump delivers in excess of 400 mBar (40 kPa) stall pressure and 1.5 litres per minute free air flow.

The piezo air pump weighs less than 10 gm, and may weigh less than 6 gm.

In operation, the breast pump system makes less then 30 dB noise at maximum power and less than 25 dB at normal power, against a 20 dB ambient noise.

In operation, the breast pump system makes approximately 24 dB noise at maximum power and 22 dB at normal power, against a 20 dB ambient noise.

The piezo pump is fed by air that passes through an air filter.

The piezo-air pump is a closed loop negative air-pressure system that applies negative pressure to a region surrounding a woman's breast to pump milk form that breast.

Feature 21 Elvie has a Piezo Air-Pump and Self-Sealing Diaphragm

A breast pump system including:

(a) a housing;

(b) a piezo air-pump in the housing that is part of a closed loop system that drives, a physically separate, deformable, self-sealing diaphragm, to generate negative air pressure.

Optional:

The breast pump is wearable and the housing is shaped at least in part to fit inside a bra.

Piezo air pump is positioned at or close to the base of the housing.

There are two or more piezo air pumps.

There are two or more piezo air pumps mounted in a series arrangement.

There are two or more piezo air pumps mounted in a parallel arrangement.

The closed system is separated from a 'milk' side by the flexible diaphragm.

Deformable diaphragm is removably mounted against a part of a breast shield.

Deformable diaphragm is a unitary or one-piece object that is removably mounted against a part of a breast shield.

Deformable diaphragm is not physically connected to the piezo air-pump.

Piezo air-pump is a closed loop air-pump that drives a physically separate and remote deformable diaphragm that removably fits directly onto the breast shield.

Deformable diaphragm is a flexible generally circular diaphragm that sits over a diaphragm housing that is an integral part of a breast shield.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

The piezo pump delivers in excess of 400 mBar (40 kPa) stall pressure and 1.5 litres per minute free air flow.

The piezo air pump weighs less than 10 gm, and may weigh less than 6 gm.

In operation, the breast pump system makes less then 30 dB noise at maximum power and less than 25 dB at normal power, against a 20 dB ambient noise.

In operation, the breast pump system makes approximately 24 dB noise at maximum power and 22 dB at normal power, against a 20 dB ambient noise.

The piezo pump is fed by air that passes through an air filter.

The piezo-air pump is a closed loop negative air-pressure system that applies negative pressure to a region surrounding a woman's breast to pump milk form that breast.

Feature 22 Elvie Uses More than One Piezo Air Pump in Series

A breast pump system including:
(a) a housing;
(b) multiple piezo air-pumps in the housing that drives a deformable diaphragm inside the housing to generate negative air pressure; in which the multiple piezo air-pumps can be operated at different times in series-connected and in parallel-connected modes.

Optional:
The breast pump is wearable and the housing is shaped at least in part to fit inside a bra.
Parallel connected mode is used during a first part of a pumping cycle to reach a defined negative air pressure more quickly than series connected mode would, and then the system switches to a series connected mode to reach a greater negative air pressure than series connected mode can reach.
An actuator switches the system from parallel-connected piezo pump mode to series-connected piezo pump mode.
Each piezo pump delivers in excess of 400 mBar (40 kPa) stall pressure and 1.5 litres per minute free air flow.
Each piezo air pump weighs less than 10 gm, and may weigh less than 6 gm.
In operation, the breast pump system makes less then 30 dB noise at maximum power and less than 25 dB at normal power, against a 20 dB ambient noise.
In operation, the breast pump system makes approximately 24 dB noise at maximum power and 22 dB at normal power, against a 20 dB ambient noise.
Each piezo pump is fed by air that passes through an air filter.
Each piezo air pump forms part of a closed or closed loop system.
Each piezo air pump is positioned at or close to the base of the housing.
There are two or more piezo air pumps.
The piezo-air pumps are a closed loop negative air-pressure system that applies negative pressure to a region surrounding a woman's breast to pump milk form that breast.
The piezo air-pump is a closed loop negative air-pressure system that drives a physically separate and remote deformable, self-sealing diaphragm that removably fits directly onto the breast shield.

Feature 23 Elvie is Wearable and has a Piezo Air-Pump, a Breast Shield and a Diaphragm that Fits Directly onto the Breast Shield A wearable breast pump system including:
(a) a housing shaped at least in part to fit inside a bra;
(b) a breast shield that attaches to the housing;
(b) a piezo air-pump in the housing that drives a deformable diaphragm that fits directly onto the breast shield.

Optional:
Deformable diaphragm is a flexible generally circular diaphragm that sits over a diaphragm housing that is an integral part of a breast shield.
Deformable diaphragm is removable from the diaphragm housing for cleaning.
Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.
Piezo air pump forms part of a closed or closed loop system.
The piezo-air pump is a closed loop negative air-pressure system that applies negative pressure to a region surrounding a woman's breast to pump milk form that breast.
The piezo air-pump is a closed loop negative air-pressure system that drives a physically separate and remote deformable, self-sealing diaphragm that removably fits directly onto the breast shield.
Piezo air pump is position at or close to the base of the housing.
There are two or more piezo air pumps.
There are two or more piezo air pumps mounted in a series arrangement.
There are two or more piezo air pumps mounted in a parallel arrangement.
The piezo pump delivers in excess of 400 mBar (40 kPa) stall pressure and 1.5 litres per minute free air flow.
The piezo air pump weighs less than 10 gm, and may weigh less than 6 gm.
In operation, the breast pump system makes less then 30 dB noise at maximum. power and less than 25 dB at normal power, against a 20 dB ambient noise.
In operation, the breast pump system makes approximately 24 dB noise at maximum power and 22 dB at normal power, against a 20 dB ambient noise. The piezo pump is fed by air that passes through an air filter.
The breast shield and milk container are each pressed or pushed into engagement with the housing.
The breast shield and milk container are each pressed or pushed into a latched engagement with the housing.
The breast shield and milk container are each insertable into and removable from the housing using an action confirmed with an audible sound, such as a click.
Breast shield is a one-piece item including a generally convex surface shaped to fit over a breast and a nipple tunnel shaped to receive a nipple.
Breast shield is generally symmetrical about a centre-line running from the top to the bottom of the breast shield when positioned upright for normal use.
Breast shield is configured to be rotated smoothly around a nipple inserted into the nipple tunnel to position a diaphragm housing portion of the breast shield at the top of the breast.
Breast shield slides into the housing using guide members.
Housing is configured to slide onto the breast shield, when the breast shield has been placed onto a breast, using guide members.
Breast shield latches into position against the housing.
Breast shield latches into position against the housing when spring plungers, such as ball bearings in the housing locate into small indents in the breast shield.

Feature 24 Elvie is Wearable and has a Piezo Air-Pump for Quiet Operation and a Re-Useable, Rigid Milk Container for Convenience A wearable breast pump system including:
(a) a housing shaped at least in part to fit inside a bra;
(b) a piezo air-pump in the housing, (c) and a re-useable, rigid or non-collapsible milk container that when connected to the housing forms an integral part of the housing and that is also removable from the housing.

Optional:
Piezo air pump forms part of a closed or closed loop system.
Piezo air pump is positioned at or close to the base of the housing.
There are two or more piezo air pumps.
There are two or more piezo air pumps mounted in a series arrangement.
There are two or more piezo air pumps mounted in a parallel arrangement.
The piezo-air pump is a closed loop negative air-pressure system that applies negative pressure to a region surrounding a woman's breast to pump milk form that breast.
The closed system is separated from a 'milk' side by a flexible diaphragm.
A deformable diaphragm inside the housing is driven by negative air pressure generated by the piezo pump.
The piezo air-pump is a closed loop negative air-pressure system that drives a physically separate and remote deformable, self-sealing diaphragm that removably fits directly onto the breast shield.
The deformable diaphragm is a flexible generally circular diaphragm that sits over a diaphragm housing that is an integral part of a breast shield.
The deformable diaphragm is removable from the diaphragm housing for cleaning.
Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.
Nipple tunnel in the breast shield includes an opening on its lower surface that is positioned through which expressed milk flows directly into the milk container.
The piezo pump delivers in excess of 400 mBar (40 kPa) stall pressure and 1.5 litres per minute free air flow.
The piezo air pump weighs less than 10 gm, and may weigh less than 6 gm.
In operation, the breast pump system makes less then 30 dB noise at maximum power and less than 25 dB at normal power, against a 20 dB ambient noise.
In operation, the breast pump system makes approximately 24 dB noise at maximum power and 22 dB at normal power, against a 20 dB ambient noise.
The milk container forms the base of the system.
The milk container has a flat base so that it can rest stably on a surface.
The milk container is removable from the housing.
The milk container includes a clear or transparent wall or section to show the amount of milk collected.
The milk container is sealable for storage.
The milk container obviates the need for consumable or replaceable milk pouches.

Feature 25 Elvie has a Piezo-Pump for Quiet Operation and is a Connected Device

A breast pump system including
(a) a housing;
(b) a piezo air-pump in the housing,
(c) a milk container,
(d) a data connectivity module that enables data collection relating to the operation of the piezo air-pump and transmission of that data to a data analysis system.

Optional:
The breast pump is wearable and the housing is shaped at least in part to fit inside a bra.
Transmission is to an application running on a connected device such as a smartphone, or a server, or the cloud.
The data collection and transmission relates to any other operational data of the system.
Piezo air pump forms part of a closed or closed loop system.
Piezo air pump is positioned at or close to the base of the housing.
There are two or more piezo air pumps.
There are two or more piezo air pumps mounted in a series arrangement.
There are two or more piezo air pumps mounted in a parallel arrangement.
The piezo-air pump is a closed loop negative air-pressure system that applies negative pressure to a region surrounding a woman's breast to pump milk form that breast.
The piezo air-pump is a closed loop negative air-pressure system that drives a physically separate and remote deformable, self-sealing diaphragm that removably fits directly onto the breast shield.
The closed system is separated from a 'milk' side by a flexible diaphragm.
A deformable diaphragm inside the housing is driven by negative air pressure generated by the piezo pump.
The deformable diaphragm is a flexible generally circular diaphragm that sits over a diaphragm housing that is an integral part of a breast shield.
Deformable diaphragm is removable from the diaphragm housing for cleaning.
Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.
Nipple tunnel in the breast shield includes an opening on its lower surface that is positioned through which expressed milk flows directly into the milk container.
The piezo pump delivers in excess of 400 mBar (40 kPa) stall pressure and 1.5 litres per minute free air flow.
The piezo air pump weighs less than 10 gm, and may weigh less than 6 gm.
In operation, the breast pump system makes less then 30 dB noise at maximum power and less than 25 dB at normal power, against a 20 dB ambient noise.
In operation, the breast pump system makes approximately 24 dB noise at maximum power and 22 dB at normal power, against a 20 dB ambient noise.
A sub-system measures or infers the quantity and/or the height of the liquid in the container and shares that data with the data connectivity module.
The sub-system measures or infers the quantity and/or the height of the liquid in the container by using one or more light emitters and light detectors to detect light from the emitters that has been reflected by the liquid, and measuring the intensity of that reflected light.
Sub-system includes an accelerometer and uses a signal from the accelerometer to determine if the liquid is sufficiently still to permit the sub-system to accurately measure or infer the quantity and/or the height of the liquid in the container.

The data analysis system analyses metrics such as any of the following: amount of milk expressed over one or more sessions, rate at which milk is expressed over one or more sessions, profile of the rate at which milk is expressed over one or more sessions.

The data analysis system analyses metrics such as any of the following pump speed, length of a single pumping session, negative air pressure or vacuum level, peak negative air pressure or vacuum level, pump cycle time or frequency, changing profile of pump speed over a single pumping session time of day.

The data analysis system analyses metrics such as any of the following: amount and type of liquids consumed by the mother, state of relaxation of the mother before or during a session, state of quiet experienced by the mother before or during a session, what overall milk expression profile the mother most closely matches.

Feature 26 Elvie Uses a Piezo in Combination with a Heat Sink that Manages the Heat Produced by the Pump.

A breast pump system including:
(a) a housing;
(b) a piezo air-pump in the housing that drives a deformable diaphragm inside the housing to generate negative air pressure;
(c) a heat sink to manage the heat produced by the piezo-air pump to ensure it can be worn comfortably.

Optional:
The heat sink is configured to ensure that the maximum temperature of any parts of the breast pump system that might come into contact with the skin, especially prolonged contact for greater than 1 minute, are no more than 48° C. and preferably no more than 43° C.

The breast pump is wearable and the housing is shaped at least in part to fit inside a bra.

Heat sink is connected to an air exhaust so that air warmed by the piezo pumps vents to the atmosphere.

Heat sink warms a breast shield.

Piezo air pump forms part of a closed or closed loop system.

Piezo air pump is positioned at or close to the base of the housing.

There are two or more piezo air pumps.

There are two or more piezo air pumps, each connected to its own or a shared heat sink.

There are two or more piezo air pumps mounted in a series arrangement.

There are two or more piezo air pumps mounted in a parallel arrangement.

The piezo-air pump is a closed loop negative air-pressure system that applies negative pressure to a region surrounding a woman's breast to pump milk form that breast.

The piezo air-pump is a closed loop negative air-pressure system that drives a physically separate and remote deformable, self-sealing diaphragm that removably fits directly onto the breast shield.

The closed system is separated from a 'milk' side by a flexible diaphragm.

A deformable diaphragm inside the housing is driven by negative air pressure generated by the piezo pump.

The deformable diaphragm is a flexible generally circular diaphragm that sits over a diaphragm housing that is an integral part of a breast shield.

The deformable diaphragm is removable from the diaphragm housing for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

Nipple tunnel in the breast shield includes an opening on its lower surface that is positioned through which expressed milk flows directly into the milk container.

The piezo pump delivers in excess of 400 mBar (40 kPa) stall pressure and 1.5 litres per minute free air flow.

The piezo air pump weighs less than 10 gm, and may weigh less than 6 gm.

In operation, the breast pump system makes less then 30 dB noise at maximum power and less than 25 dB at normal power, against a 20 dB ambient noise.

In operation, the breast pump system makes approximately 24 dB noise at maximum power and 22 dB at normal power, against a 20 dB ambient noise.

Feature 27 Elvie is Wearable and Gently Massages a Mother's Breast Using Small Bladders Inflated by Air from its Negative Pressure Air-Pump A breast pump system including:
(a) a housing;
(b) an air-pump in the housing that drives a closed loop negative air-pressure system that applies negative pressure to a region surrounding a woman's breast to pump milk form that breast;
(c) in which the air pump also provides air to regularly or sequentially inflate one or more air bladders or liners that are configured to massage one or more parts of the breast.

Optional:
Air-pump is a piezo pump.
Breast pump system is wearable and the housing is shaped at least in part to fit inside a bra.
Bladders or liners are formed in a breast shield that attaches to the housing.

Feature 28 Elvie is Wearable and Gently Warms a Mother's Breast Using Small Chambers Inflated by Warm Air from its Negative Pressure Air-Pump A breast pump system including.
(a) a housing;
(b) an air-pump, such as a piezo pump, in the housing that drive a closed loop negative air-pressure system that applies negative pressure to a region surrounding a woman's breast to pump milk form that breast;
(c) in which the air pump also provides warm air to regularly or sequentially inflate one or more air chambers that are configured to apply warmth to one or more parts of the breast.

Optional:
Breast pump system is wearable and the housing is shaped at least in part to fit inside a bra.
The air chamber is a deformable diaphragm positioned on a breast shield that attaches to the housing.

C. Elvie Milk Container Feature Cluster

Feature 29 Elvie is Wearable and Includes a Re-Useable, Rigid Milk Container that Forms the Lower Part of the Pump, to Fit Inside a Bra Comfortably A wearable breast pump system configured including:
(a) a housing shaped at least in part with a curved surface to fit inside a bra and including a pumping mechanism;
(b) and a re-useable rigid or non-collapsible milk container that when connected to the housing forms an integral, lower part of the housing, with a surface shaped to continue the curved shape of the housing, so that the pump system can be held comfortably inside the bra.

Optional:

The milk container forms the base of the system.

The milk container has a flat base so that it can rest stably on a surface.

The milk container is attached to the housing with a push action.

The milk container includes a clear or transparent wall or section to show the amount of milk collected.

The milk container is sealable for storage.

The milk container obviates the need for consumable or replaceable milk pouches.

The milk container includes an aperture, spout or lid that sits directly underneath an opening in a nipple tunnel of a breast shield, and expressed milk flows under gravity through the opening in the nipple tunnel and into the milk container.

The milk container includes an aperture, spout or lid that self-seals under the negative air-pressure from the pumping mechanism against an opening in a breast shield, and milk flows under gravity through the opening into the milk container.

The milk container is made using a blow moulding construction.

The milk container has a large diameter opening to facilitate cleaning that is at least 3 cm in diameter.

The large opening is closed with a bayonet-mounted cap with an integral spout.

A flexible rubber or elastomeric valve is mounted onto the cap or spout and includes a rubber or elastomeric duck-bill valve that stays sealed when there is negative air-pressure being applied by the air pump mechanism to ensure that negative air-pressure is not applied to the milk container.

The pumping mechanism is a closed loop negative air-pressure system that applies negative pressure to a region surrounding a woman's breast to pump milk form that breast.

Feature 30 Elvie is Wearable and Includes a Milk Container that Latches to the Housing with a Simple Push to Latch Action A wearable breast pump system including:

(a) a housing shaped at least in part to fit inside a bra and including a pumping mechanism;

(b) and a milk container that is attachable to the housing with a mechanism that releasably attaches or latches when the milk container is sufficiently pressed on to the housing with a single push action.

Optional:

The milk container includes an aperture, spout or lid that self-seals under the negative air-pressure from the pumping mechanism against an opening in a breast shield, and milk flows under gravity through the opening into the milk container.

Milk container, when connected to the housing, forms an integral, lower part of the housing and that is removable from the housing with a release mechanism that can be operated with one hand.

Mechanism that releasably attaches or latches is a mechanical or magnetic mechanism.

Mechanical mechanism includes flanges on the top of the milk container, or the sealing plate that seals the opening to the milk contained, that engage with and move past a surface to occupy a latched position over that surface when the milk container is pressed against the housing to lock into the housing.

The housing includes a button that when pressed releases the milk container from the housing by flexing the surface away from the flanges so that the flanges no longer engage with and latch against the surface.

Mechanism that attaches or latches the milk container into position does so with an audible click.

The milk container forms the base of the system.

The milk container has a flat base so that it can rest stably on a surface.

The milk container is removable from the housing by releasing the latch and moving the housing off the milk container.

The milk container includes a clear or transparent wall or section to show the amount of milk collected.

The milk container is sealable for storage.

The milk container obviates the need for consumable or replaceable milk pouches.

The milk container includes an aperture that sits directly underneath an opening in a nipple tunnel of a breast shield, and expressed milk flows under gravity through the opening in the nipple tunnel and into the milk container.

The milk container is made using a blow moulding construction.

The milk container has a large diameter opening to facilitate cleaning that is at least 3 cm in diameter.

The large opening is closed with a bayonet-mounted cap with an integral spout.

A flexible rubber or elastomeric valve is mounted onto the cap or spout and includes a rubber or elastomeric duck-bill valve that stays sealed when there is negative air-pressure being applied by the air pump to ensure that negative air-pressure is not applied to the milk container.

The pumping mechanism is a closed loop negative air-pressure system that applies negative pressure to a region surrounding a woman's breast to pump milk form that breast.

Feature 31 Elvie is Wearable and Includes a Removable Milk Container with an Integral Milk Pouring Spout for Convenience A wearable breast pump system including:

(a) a housing shaped at least in part to fit inside a bra and including a pumping mechanism;

(b) and a re-useable milk container that is connected to the housing with a surface shaped to continue the curved or breast-like shape of the pump, so that the pump can be held comfortably inside a bra and where the milk container includes a pouring spout for pouring milk.

Optional:

Spout is integral to the milk container.

Spout is integral to a removable lid to the milk container.

Spout is positioned at or close to the front edge of the milk container.

Spout is removable from the container, such as by clipping off the container.

A teat is attachable to the spout.

A flexible rubber or elastomeric valve is mounted onto the cap or spout and includes a rubber or elastomeric duck-bill valve that stays sealed when there is negative air-pressure being applied by the air pump to ensure that negative air-pressure is not applied to the milk container.

The milk container forms the base of the system.

The milk container has a flat base so that it can rest stably on a surface.

The milk container is removable from the housing.

The milk container includes a clear or transparent wall or section to show the amount of milk collected.

The milk container is sealable for storage.

The milk container obviates the need for consumable or replaceable milk pouches.

The milk container includes an aperture that sits directly underneath an opening in a nipple tunnel of a breast shield, and expressed milk flows under gravity through the opening in the nipple tunnel and into the milk container through the pouring spout in the milk container.

The milk container includes an aperture, spout or lid that self-seals under the negative air-pressure from the pumping mechanism against an opening in a breast shield, and milk flows under gravity through the opening into the milk container.

The milk container is made using a blow moulding construction.

The milk container has a large diameter opening to facilitate cleaning that is at least 3 cm in diameter.

The large opening is closed with a bayonet-mounted cap with an integral spout.

The pumping mechanism is a closed loop negative air-pressure system that applies negative pressure to a region surrounding a woman's breast to pump milk form that breast.

Feature 32 Elvie is Wearable and Includes a Removable Milk Container Below the Milk Flow Path Defined by a Breast Shield for Fast and Reliable Milk Collection A wearable breast pump system including:

(a) a housing including a pumping mechanism, the housing being shaped at least in part to fit inside a bra;

(b) and a breast shield including a nipple tunnel shaped to receive a nipple, and including an opening that defines the start of a milk flow path;

(c) a re-useable milk container that when connected to the housing is positioned entirely below the opening or the milk flow path, when the breast pump is positioned or oriented for normal use.

Optional:

The milk container includes an aperture that sits directly underneath the opening in the nipple tunnel in the breast shield, and expressed milk flows under gravity through the opening in the nipple tunnel and into the milk container through the pouring spout in the milk container.

Milk flows from the opening directly into the milk container.

Milk flows from the opening directly into the milk container.

The milk container includes an aperture, spout or lid that self-seals under the negative air-pressure from the pumping mechanism against the opening in the breast shield, and milk flows under gravity through the opening into the milk container.

Milk flows from the opening directly onto a valve that is attached to the milk container, the valve closing whilst there is sufficient negative air pressure in the volume of air between the valve and the breast shield opening, and then opening to release the milk into the container when the air pressure rises sufficiently.

Milk flows from the opening directly onto a valve that is attached to a spout, that is in turn attached to the milk container.

The milk container has a large diameter opening to facilitate cleaning that is at least 3 cm in diameter.

The large opening is closed with a bayonet-mounted cap with an integral spout.

A flexible rubber or elastomeric valve is mounted onto the milk container cap or spout and includes a rubber or elastomeric duck-bill valve that stays sealed when there is negative air-pressure being applied by the air pump to ensure that negative air-pressure is not applied to the milk container, and milk flows towards and is retained by the duck bill valve whilst the valve is closed, and flows past the valve into the milk container when the negative air pressure is released and the valve opens.

The breast shield and milk container are each pressed or pushed into engagement with the housing.

The breast shield and milk container are each pressed or pushed into a latched engagement with the housing.

The two removable parts are each insertable into and removable from the housing using an action confirmed with an audible sound, such as a click.

Breast shield is a one-piece item including a generally convex surface shaped to fit over a breast and a nipple tunnel shaped to receive a nipple.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Breast shield slides into the housing using guide members.

Housing is configured to slide onto the breast shield, when the breast shield has been placed onto a breast, using guide members.

Breast shield latches into position against the housing.

Breast shield latches into position against the housing when spring plungers, such as ball bearings in the housing locate into small indents in the breast shield.

Breast shield latches into position against the housing using magnets.

Feature 33 Elvie is Wearable and Includes a Breast Shield and Removable Milk Container of Optically Clear, Dishwasher Safe Plastic for Ease of Use and Cleaning A breast pump system including:

(a) a housing including a pumping mechanism;

(b) and a breast shield defining a region shaped to receive a nipple, the region defining the start of a milk flow path;

(c) a re-useable, rigid or non-collapsible milk container that when connected to the housing is positioned to form the base of the housing, and in which the breast shield and the milk container are made substantially of an optically clear, dishwasher safe material.

Optional:

The material is a polycarbonate material, such as Tritan™.

breast pump system is wearable and the housing is shaped at least in part to fit inside a bra.

Breast shield is a one-piece item including a generally convex surface shaped to fit over a breast and a nipple tunnel shaped to receive a nipple.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Breast shield operates with a flexible diaphragm that flexes when negative air pressure is applied to it by an air pump system in the housing, and transfers that negative air-pressure to pull the breast and/or nipple against the breast shield to cause milk to be expressed.

Flexible diaphragm is removable from a diaphragm housing portion of the breast shield for cleaning.

Diaphragm housing includes an air hole that transfers negative air pressure to a nipple tunnel in the breast shield, the negative air pressure arising when the diaphragm moves away from the diaphragm housing and towards the housing, and the negative air pressure in the nipple tunnel pulling the breast and/or nipple against the breast shield to cause milk to be expressed.

The breast shield and milk container are each pressed or pushed into engagement with the housing.

The breast shield and milk container are each pressed or pushed into a latched engagement with the housing.

The breast shield and milk container are each insertable into and removable from the housing using an action confirmed with an audible sound, such as a click.

The milk container includes an aperture, spout or lid that self-seals under the negative air-pressure from the pumping mechanism against an opening in a breast shield, and milk flows under gravity through the opening into the milk container.

Breast shield is a one-piece item including a generally convex surface shaped to fit over a breast and a nipple tunnel shaped to receive a nipple.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Breast shield slides into the housing using guide members.

Housing is configured to slide onto the breast shield, when the breast shield has been placed onto a breast, using guide members.

Breast shield latches into position against the housing.

Breast shield latches into position against the housing when spring plungers, such as ball bearings in the housing locate into small indents in the breast shield.

Breast shield latches into position against the housing using magnets.

Feature 34 Elvie is Wearable and Includes Various Components that Self-Seal Under Negative Air Pressure, for Convenience of Assembly and Disassembly A wearable breast pump system including:

(a) a housing shaped at least in part to fit inside a bra and including an air pumping mechanism;

(b) a breast shield;

(c) a diaphragm that flexes in response to changes in air pressure caused by the air pumping mechanism and that seals to the breast shield;

(d) a re-useable milk container that seals to the breast shield;

and in which either or both of the diaphragm and the re-useable milk container substantially self-seal under the negative air pressure provided by the pumping mechanism.

Optional:

The milk container includes an aperture, spout or lid that self-seals under the negative air-pressure from the pumping mechanism against an opening in a breast shield, and milk flows under gravity through the opening into the milk container.

The re-useable milk container includes a 1 way valve that self-seals against a conduit from the breast shield and allows milk to pass into the container but not spill out, and in which the valve (a) closes and (b) partly or wholly self-seals against the conduit under the negative air pressure provided by the pumping mechanism.

The 1 way valve is attached to the milk container, or a lid or spout of the milk container with an interference fit and is readily removed in normal use for separate cleaning.

The diaphragm partly or wholly self-seals to the breast shield under the negative air pressure provided by the pumping mechanism.

The diaphragm partly or wholly self-seals to the housing under the negative air pressure provided by the pumping mechanism.

The diaphragm is attached to the diaphragm housing using elastomeric or rubber latches and is readily removed in normal use for separate cleaning.

The breast shield and milk container are each pressed or pushed into engagement with the housing.

The breast shield and milk container are each pressed or pushed into a latched engagement with the housing.

The breast shield and milk container are each insertable into and removable from the housing using an action confirmed with an audible sound, such as a click.

Breast shield is a one-piece item including a generally convex surface shaped to fit over a breast and a nipple tunnel shaped to receive a nipple.

Breast shield is generally symmetrical about a centre-line running from the top to the bottom of the breast shield when positioned upright for normal use.

Breast shield is configured to be rotated smoothly around a nipple inserted into the nipple tunnel to position a diaphragm housing portion of the breast shield at the top of the breast.

Breast shield slides into the housing using guide members.

Housing is configured to slide onto the breast shield, when the breast shield has been placed onto a breast, using guide members.

Breast shield latches into position against the housing.

Breast shield latches into position against the housing when spring plungers, such as ball bearings in the housing locate into small indents in the breast shield.

Breast shield latches into position against the housing using magnets.

Feature 35 Elvie is Wearable and Includes a Spout at the Front Edge of the Milk Container for Easy Pouring A wearable breast pump system configured as a single unit and including:

(a) a housing shaped at least in part to fit inside a bra and including a pumping mechanism;

(b) and a milk container that forms an integral part of the housing;

(c) a re-useable pouring spout that is positioned at or close to the front edge of the milk container.

Optional:

Milk container is a multifunctional bottle, operating as both a storage container to contain milk that is being expressed, as well as a refrigeratable and freezable storage bottle for that milk, as well as a bottle from which that milk can be drunk by a baby.

Spout is integral to a removable lid to the milk container.

Spout is removable from the container, such as by clipping off the container.

A teat is attachable to the spout.

By placing the spout at or close to the front edge of the milk container, the milk container fully empties more readily than where the spout is placed in the middle of the lid of a milk container.

The spout sits generally under an opening in the breast shield spout or nipple tunnel through which expressed milk flows.

The re-useable milk container includes a 1 way valve that self-seals against a conduit from the breast shield and allows milk to pass into the container but not spill out, and in which the valve (a) closes and (b) partly or wholly self-seals against the conduit under the negative air pressure provided by the pumping mechanism.

The milk container includes an aperture, spout or lid that self-seals under the negative air-pressure from the pumping mechanism against an opening in a breast shield, and milk flows under gravity through the opening into the milk container.

Feature 36 Elvie is Wearable and Includes a Milk Container that is Shaped with Broad Shoulders and that can be Adapted as a Drinking Bottle that Baby can Easily Hold A wearable breast pump system configured as a single unit and including:

(a) a housing shaped at least in part to fit inside a bra and including a pumping mechanism;

(b) a breast shield;

(c) a milk container that is removable from the housing and is shaped or configured to also serve as a drinking bottle that is readily held by a baby because it is wider than it is tall.

Optional:

Teat is attachable directly to the milk container.

Pouring or drinking spout is integral to the milk container.

The shoulders are at least 2 cm in width, and the neck is no more than 1 cm in height, to enable a baby to readily grip and hold the container when feeding from the milk in the container.

Spout/teat/straw resides near the edge of the container's rim.

Milk container is a multifunctional bottle, operating as both a storage container to contain milk that is being expressed, as well as a refrigertable and freezable storage bottle for that milk, as well as a bottle from which that milk can be drunk by a baby.

The re-useable milk container includes a 1 way valve that self-seals against a conduit from the breast shield and allows milk to pass into the container but not spill out, and in which the valve (a) closes and (b) partly or wholly self-seals against the conduit under the negative air pressure provided by the pumping mechanism.

The milk container includes an aperture, spout or lid that self-seals under the negative air-pressure from the pumping mechanism against an opening in a breast shield, and milk flows under gravity through the opening into the milk container.

Spout is integral to the milk container.

Spout is integral to a removable lid to the milk container.

Spout is positioned at or close to the front edge of the milk container.

Spout is removable from the container, such as by clipping off the container.

A teat is attachable to the spout.

A flexible rubber or elastomeric valve is mounted onto the cap or spout and includes a rubber or elastomeric duck-bill valve that stays sealed when there is negative air-pressure being applied by the air pump to ensure that negative air-pressure is not applied to the milk container.

The milk container forms the base of the system.

The milk container has a flat base so that it can rest stably on a surface.

The milk container is removable from the housing.

The milk container includes a clear or transparent wall or section to show the amount of milk collected.

The milk container is sealable for storage.

The milk container obviates the need for consumable or replaceable milk pouches.

The milk container includes an aperture that sits directly underneath an opening in a nipple tunnel of a breast shield, and expressed milk flows under gravity through the opening in the nipple tunnel and into the milk container through the pouring spout in the milk container.

The milk container is made using a blow moulding construction.

The milk container has a large diameter opening to facilitate cleaning that is at least 3 cm in diameter.

The large opening is closed with a bayonet-mounted cap with an integral spout.

D. Elvie IR System Feature Cluster

Feature 37 Elvie is Wearable and Includes a Light-Based System that Measures the Quantity of Milk in the Container for Fast and Reliable Feedback A system for milk volume determination, for use as part of a breast pump, or breast milk collecting device, including:

(a) a re-useable rigid or non-collapsible milk container, (b) at least one light emitter, configured to direct radiation towards the surface of the milk;

(c) at least one light detector, configured to detect reflected radiation from the surface of the milk;

wherein the light emitters and detectors operate as part of a sub-system that measures the height of, or infers the quantity of, the milk in the container.

Optional:

The wearable breast pump system includes:

(a) a housing shaped at least in part to fit inside a bra and including a pumping mechanism;

(b) and a breast shield;

(c) a re-useable rigid or non-collapsible milk container that when connected to the housing is positioned to form the base of the housing, and in which the top of the container includes an optically clear region that is aligned below one or more light emitters positioned in the base of the housing.

The sub-system measures or infers the quantity and/or the height of the liquid in the container by using one or more light emitters and light detectors to detect light from the emitters that has been reflected by the liquid, and measuring the intensity of that reflected light.

Sub-system includes an accelerometer and uses a signal from the accelerometer to determine if the liquid is sufficiently still to permit the sub-system to accurately measure or infer the quantity and/or the height of the liquid in the container.

The sub-system measures or infers the quantity and/or the height of the liquid in the container and shares that data with a data connectivity module.

Where the quantity or level exceeds a threshold, then the pumping mechanism automatically changes mode, e.g. from a stimulation mode to an expression mode.

Where the quantity or level exceeds a threshold, then the pumping mechanism automatically stops.

Milk-flow data is captured and stored.

If milk-flow falls below a threshold, then a notification is provided to the mother.

Feature 38 the Separate IR Puck for Liquid Quantity Measurement

A liquid-level measuring system for measuring the quantity of liquid in a container for a breast pump; the system including:

(a) one or more light emitters directing light at the surface of the liquid in the container, (b) one or more light receivers configured to detect light from the light emitters that has been reflected from the liquid;

(c) a sub-system that infers, measures or calculates the quantity in the liquid using measured properties of the detected light (d) a collar or other fixing system that positions the system over the container.

Optional:

The quantity of milk is measured as milk enters the container or as milk is removed from the container.

Measured property includes the reflected light intensity

Feature 39 the Separate IR Puck Combined with Liquid Tilt Angle Measurement

A liquid-level measuring system for measuring the tilt angle of liquid in a container the system including:

(a) one or more light emitters directing light at the surface of the liquid in the container, (b) one or more light receivers configured to measure properties of the light reflected from the liquid;

(c) a sub-system including an accelerometer that infers, measures or calculates the tilt angle of the liquid using measured properties of the detected light;

(d) a collar or other fixing system that positions the system over the container.

Optional:

Measured property includes the reflected light intensity

The quantity of liquid is measured as liquid enters the container or as liquid is removed from the container.

Sub-system includes an accelerometer and uses a signal from the accelerometer to determine if the liquid is sufficiently still to permit the sub-system to accurately measure or infer the quantity and/or the height of the liquid in the container.

The sub-system measures or infers the quantity and/or the height of the liquid in the container and shares that data with a data connectivity module.

Generally Applicable Optional Features

Weight of the entire unit, unfilled, is under 250 g and preferably 214 g.

Silver based bactericide is used on all parts that are not steam or heat sterilized in normal cleaning.

Housing includes a rechargeable battery.

System is self-contained.

System is a closed loop system.

Breast pump system is a self-contained, wearable device that includes an integral rechargeable battery, control electronics, and one or more air pumps operating as a closed system, driving a flexible diaphragm that in turn delivers negative air-pressure to the breast, to cause milk to be expressed.

Housing has a generally rounded or convex front surface and has a generally tear-drop shape when seen from the front.

E. Bra Clip Feature Cluster

Feature 40 Bra Adjuster

A bra adjuster for a nursing or maternity bra, the nursing or maternity bra including a bra cup with a flap that can be undone to expose the nipple, and the flap attaching to the shoulder strap using a clasp, hook or other fastener attached to the flap, and a corresponding fastener attached to the shoulder strap;

and in which the bra adjuster is attachable at one end to the fastener attached to the flap, and at its other end to the fastener attached to the shoulder strap, and hence increases the effective bra cup size sufficiently to accommodate a wearable breast pump, and is also detachable from the flap and shoulder strap.

Optional:

Bra adjuster is retained in position on the bra during normal wearing of the bra, even when the flap is attached directly to the shoulder strap, and is used to increases the effective bra cup size only when the wearable breast pump is used.

Bra adjuster is extensible or elastic.

Bra adjuster is of a fixed length.

Bra adjuster includes a clip that the user can slide onto the bra strap to secure the bra adjuster in position.

Bra adjuster is machine-washing washable.

F. Other Features that can Sit Outside the Breast Pump Context

Feature 41 Wearable Device Using More than One Piezo Pump Connected in Series or in Parallel A wearable device including multiple piezo pumps mounted together either in series or in parallel.

Optional:

The wearable device is a medical wearable device.

The piezo pumps air or any liquid etc.

The system can switch between a parallel mode and a series mode to arrive to lower or higher pressure quicker.

Feature 42 Wearable Medical Device Using a Piezo Pump and a Heat Sink Attached Together.

A wearable medical device including a piezo pump and a heat sink attached together.

Optional

The wearable device uses more than one piezo pump connected in series.

The wearable device uses more than one piezo pump connected in parallel.

Each piezo pump is connected to its own heat sink, or to a common heat sink.

The or each heat sink is configured to ensure that the maximum temperature of any parts of the breast pump system that might come into contact with the skin, especially prolonged contact for greater than 1 minute, are no more than 48° C. and preferably no more than 43° C.

The wearable device includes a thermal cut out.

Excess heat is diverted to a specific location on the device that is selected to not be in prolonged contact with the skin of the user, in normal use.

Use cases application:

Wound therapy

High degree burns

Sleep apnea

Deep vein thrombosis

Sports injury.

Wearable medical device is powered/charged via USB.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. A wearable breast pump system including:
   (a) a housing that encloses a rechargeable battery and a closed loop air pump and has a front surface that is shaped, in use, at least in part to fit inside a bra and to contact an inner surface of the bra and a rear surface that is shaped to contact, at least in part, a breast shield;
   (b) the breast shield including (i) a flange shaped to fit against a breast and (ii) a substantially transparent or optically clear, protruding nipple tunnel, shaped to receive a nipple, with a closed end section adjacent to a milk opening through which, in use, expressed milk flows under gravity; providing to the mother placing the breast shield onto her breast a clear and unobstructed view of the nipple when positioned inside the nipple tunnel, to facilitate correct nipple alignment; and where the flange and the nipple tunnel are a single, integral item, and the breast shield is insertable against, and removable from, the rear surface of the housing;
   (c) a flexible diaphragm that is seated against a diaphragm holder that is formed as a recess in the rear surface of the housing, the flexible diaphragm flexing in response to changes in air pressure caused by the closed loop air-pump to create negative air pressure in the nipple tunnel;
   (d) a rigid, re-useable milk container made of substantially transparent or optically clear material, and configured to be attachable to and removable from the housing.

2. The wearable breast pump system of claim 1 in which the milk container attaches to the housing using magnets.

3. The wearable breast pump system of claim 1 in which the milk container includes a pouring spout for pouring milk and a teat attachable to the spout.

4. The wearable breast pump system of claim 1 in which the milk container includes a flexible pouring spout that self-seals against the milk opening in the nipple tunnel through which milk flows in use.

5. The wearable breast pump system of claim 1 in which the milk container includes a flexible valve that self-seals against the milk opening in the nipple tunnel through which milk flows in use.

6. The wearable breast pump system of claim 1 in which the milk container includes a flat base so that the milk container can rest stably on a surface.

7. The wearable breast pump system of claim 1 in which the breast shield presents in use a single continuous surface to the nipple and breast.

8. The wearable breast pump system of claim 1 in which the breast shield is configured to attach to the housing with a single, sliding push action and to latch against the housing using magnets.

9. The wearable breast pump system of claim 1 in which the housing is configured to slide onto the breast shield, when the breast shield has been placed onto a breast, using guide members.

10. The wearable breast pump system of claim 1 in which the nipple tunnel includes visual guide lines that define the correct spacing of the nipple from the side walls of the nipple tunnel.

11. The wearable breast pump system of claim 1 in which the breast pump system includes only two parts that are directly removable from the housing in normal use or normal dis-assembly: the breast shield and the rigid milk container.

12. The wearable breast pump system of claim 1 in which the breast shield presents in use a single continuous surface to the breast and nipple and covers at least some of the milk container that in use faces the breast.

13. The wearable breast pump system of claim 1 in which the flexible diaphragm self-seals against the diaphragm housing.

14. The wearable breast pump system of claim 1 in which the air-pump is fitted in the housing and forms part of a closed loop system that drives the flexible diaphragm to generate negative air pressure, that diaphragm not being mounted on any side or surface of the breast shield flange but instead being mounted on the diaphragm holder, and that holder is itself distanced from, or positioned away from, the side or surface of the breast shield flange.

15. The wearable breast pump system of claim 1 in which the breast shield is a one-piece item that includes (a) the nipple tunnel and (b) the flange to rest against the breast, and the diaphragm holder is spaced apart from the breast shield flange and positioned so that the diaphragm does not at least partially surround the nipple tunnel.

16. The wearable breast pump system of claim 1 in which the diaphragm is arranged on the holder, and the holder is separated from, or positioned a distance from, or away from, the milk opening and is not on any side of the milk opening.

17. The wearable breast pump system of claim 1 in which the diaphragm is a generally circular flexible membrane.

18. The wearable breast pump system of claim 1 in which the air pump is a piezo air-pump system.

19. The wearable breast pump system of claim 18 in which the piezo air-pump system comprises two series or parallel connected piezo air-pumps.

20. The wearable breast pump system of claim 18 in which the piezo air-pump system produces no more than 30 dB at maximum power.

21. The wearable breast pump system of claim 18 in which the piezo air-pump system is a lightweight air pump that enables the total mass of the breast pump system, unfilled with milk, to be less than 250 gm.

22. The wearable breast pump system of claim 1 in which the housing includes a visual and/or haptic indicator that indicates whether milk is flowing or not flowing into the milk container and in which the haptic and/or visual indicator automatically indicates if the pumping mechanism is operating correctly to pump milk, based on whether the quantity and/or the height of the liquid in the container above its base is increasing above a threshold rate of increase.

23. The wearable breast pump system of claim 1 in which the housing includes a sensor that measures or determines the movement and/or tilt angle of the housing to detect spillage risk conditions during a pumping session and automatically affects or adjusts the operation of the system depending on the output of the sensor if a spillage risk condition is detected.

24. The wearable breast pump system of claim 1 the breast pump system including an air pressure sensor configured to measure the negative air pressure delivered by the closed-loop air pump and a measurement sub-system that measures or infers milk flow or milk volume.

25. The wearable breast pump system of claim 1 in which the housing includes a control interface that the user can select to indicate or record if milk is being expressed from the left or the right breast.

26. The wearable breast pump system of claim 1 in which the housing includes at least one light emitter, configured to direct radiation towards the surface of the milk; and at least one light detector, configured to detect reflected radiation from the surface of the milk; wherein the at least one light emitter and the least one light detector operate as part of a sub-system that measures the height of, or infers the quantity of, the milk in the container.

27. The wearable breast pump system of claim 1 in which the flange and the nipple tunnel are a single, integral item with no joining stubs.

28. The wearable breast pump system of claim 1 in which the diaphragm is a generally flat, circular flexible membrane.

* * * * *